(12) United States Patent
Coppola et al.

(10) Patent No.: US 12,208,171 B2
(45) Date of Patent: Jan. 28, 2025

(54) ULTRAVIOLET DISINFECTION AND SANITIZING SYSTEMS AND METHODS FOR ELECTRONIC GAMING DEVICES AND OTHER GAMING EQUIPMENT

(71) Applicant: Aristocrat Technologies, Inc., Las Vegas, NV (US)

(72) Inventors: Roberto Coppola, Las Vegas, NV (US); Rajendrasinh Jadeja, Las Vegas, NV (US); Frank Rodriguez, Las Vegas, NV (US); Nimish Purohit, Las Vegas, NV (US); Sandra Apple, Jersey City, NJ (US); Bruce Urban, Las Vegas, NV (US); Alfred Thomas, Las Vegas, NV (US); Scott Hendrickson, Las Vegas, NV (US); Stephen Shaffer, Jr., Las Vegas, NV (US); Xiaoqiang Gong, Las Vegas, NV (US); Joseph Kaminkow, Las Vegas, NV (US); Christopher Cleveland, Las Vegas, NV (US); Ariel Turgel, San Francisco, CA (US); Daniel Harden, Palo Alto, CA (US); Akifusa Nakazawa, Mountain View, CA (US); Benjamin Martin, San Francisco, CA (US)

(73) Assignee: Aristocrat Technologies, Inc., Las Vegas, NV (US)

( * ) Notice: Subject to any disclaimer, the term of this patent is extended or adjusted under 35 U.S.C. 154(b) by 368 days.

(21) Appl. No.: 17/243,279

(22) Filed: Apr. 28, 2021

(65) Prior Publication Data

US 2021/0338864 A1 Nov. 4, 2021

Related U.S. Application Data

(60) Provisional application No. 63/026,557, filed on May 18, 2020, provisional application No. 63/018,500, filed on Apr. 30, 2020.

(51) Int. Cl.
*A61L 2/10* (2006.01)
*A61L 2/24* (2006.01)
(Continued)

(52) U.S. Cl.
CPC ................... *A61L 2/10* (2013.01); *A61L 2/24* (2013.01); *A61L 2/26* (2013.01); *G07F 17/3216* (2013.01);
(Continued)

(58) Field of Classification Search
CPC ..... A61L 2/10; A61L 2/24; A61L 2/26; A61L 2202/11; A61L 2202/14; A61L 2202/15; A61L 2202/16; G07F 17/3216
See application file for complete search history.

(56) References Cited

U.S. PATENT DOCUMENTS

D305,704 S   1/1990  Jones
4,986,330 A  1/1991  McGonagle
(Continued)

FOREIGN PATENT DOCUMENTS

AU   2008309026 A1 *  5/2010  ........... G06F 3/0436
BR   102020006852 A2 * 10/2021
(Continued)

OTHER PUBLICATIONS

Office Action (Notice of Allowance and Fees Due (PTOL-85)) dated Sep. 9, 2021 for U.S. Appl. No. 16/947,987 (pp. 1-8).
(Continued)

*Primary Examiner* — Steven J Hylinski
(74) *Attorney, Agent, or Firm* — Blank Rome LLP

(57) ABSTRACT

Electronic gaming devices and other gaming equipment include, or are retrofitted with, ultraviolet ("UV") light sources to disinfect surfaces as well as hardware features (Continued)

and software features to manage UV disinfection cycles and report results of UV disinfection cycles.

15 Claims, 37 Drawing Sheets

(51) Int. Cl.
*A61L 2/26* (2006.01)
*G07F 17/32* (2006.01)
(52) U.S. Cl.
CPC ........ *A61L 2202/11* (2013.01); *A61L 2202/14* (2013.01); *A61L 2202/15* (2013.01); *A61L 2202/16* (2013.01)

(56) References Cited

U.S. PATENT DOCUMENTS

| | | | |
|---|---|---|---|
| 5,944,432 A * | 8/1999 | Richardson | H01H 13/70 312/208.3 |
| D427,783 S | 7/2000 | Luedke | |
| 6,230,658 B1 | 5/2001 | Rudolph | |
| 6,278,122 B1 * | 8/2001 | Gagnon | A61L 2/10 250/455.11 |
| 6,394,907 B1 | 5/2002 | Rowe | |
| 6,510,572 B2 | 1/2003 | Horowitz | |
| 6,585,598 B2 | 7/2003 | Nguyen | |
| 6,739,975 B2 | 5/2004 | Nguyen | |
| 6,835,134 B2 | 12/2004 | Poole | |
| 6,846,238 B2 | 1/2005 | Wells | |
| 6,866,586 B2 | 3/2005 | Oberberger | |
| 6,925,307 B1 | 8/2005 | Mamdani | |
| 7,114,718 B2 | 10/2006 | Grauzer | |
| 7,169,053 B2 | 1/2007 | Moik | |
| 7,240,036 B1 | 7/2007 | Mamdani | |
| 7,285,046 B2 | 10/2007 | Papulov | |
| 7,370,012 B2 | 5/2008 | Karns | |
| 7,390,263 B1 | 6/2008 | Acres | |
| 7,419,428 B2 | 9/2008 | Rowe | |
| 7,559,462 B2 | 7/2009 | Brosnan | |
| 7,749,079 B2 | 7/2010 | Chamberlain | |
| 7,771,277 B2 | 8/2010 | Chamberlain | |
| 7,819,742 B2 | 10/2010 | Chamberlain | |
| 7,918,728 B2 | 4/2011 | Nguyen | |
| D641,560 S | 7/2011 | Thompson | |
| 7,997,978 B2 | 8/2011 | Kaminkow | |
| 8,057,303 B2 | 11/2011 | Rasmussen | |
| 8,110,819 B2 * | 2/2012 | Boyarsky | A61L 2/10 250/455.11 |
| D660,022 S | 5/2012 | Thompson | |
| 8,226,255 B2 | 7/2012 | Fan | |
| 8,333,653 B2 | 12/2012 | Nyman | |
| 8,382,582 B2 | 2/2013 | Sammon | |
| 8,393,955 B2 | 3/2013 | Arezina | |
| 8,449,378 B2 | 5/2013 | Michaelson | |
| 8,463,711 B2 | 6/2013 | Cunningham, II | |
| 8,469,800 B2 | 6/2013 | Lemay | |
| 8,523,657 B2 | 9/2013 | Michaelson | |
| 8,602,874 B2 | 12/2013 | Rowe | |
| 8,613,659 B2 | 12/2013 | Nelson | |
| D702,068 S | 4/2014 | Mitten | |
| 8,714,655 B2 | 5/2014 | Cahall | |
| 8,870,647 B2 | 10/2014 | Huizinga | |
| 8,875,639 B2 | 11/2014 | Summerville | |
| 8,956,222 B2 | 2/2015 | Lemay | |
| 8,961,298 B2 | 2/2015 | Czyzewski | |
| 8,992,306 B2 | 3/2015 | Iddings | |
| D726,424 S | 4/2015 | Nguyen | |
| 9,058,716 B2 | 6/2015 | Rajaraman | |
| 9,153,095 B2 | 10/2015 | Adiraju | |
| 9,159,189 B2 | 10/2015 | Froy, Jr. | |
| 9,167,383 B1 | 10/2015 | Barrand | |
| 9,226,578 B2 | 1/2016 | Battey | |
| 9,235,953 B2 | 1/2016 | Earley | |
| 9,245,414 B2 | 1/2016 | Radisich | |
| 9,269,231 B2 | 2/2016 | Curtin | |
| 9,311,769 B2 | 4/2016 | Lemay | |
| 9,317,995 B2 | 4/2016 | Nyman | |
| 9,324,209 B2 | 4/2016 | Cunningham, II | |
| 9,367,835 B2 | 6/2016 | Nelson | |
| 9,418,519 B2 | 8/2016 | Walker | |
| 9,437,073 B2 | 9/2016 | Lestrange | |
| 9,454,872 B2 | 9/2016 | Muir | |
| 9,483,901 B2 | 11/2016 | Nguyen | |
| 9,501,899 B2 | 11/2016 | David | |
| D774,339 S | 12/2016 | Parshad | |
| 9,530,277 B2 | 12/2016 | Nelson | |
| D777,459 S | 1/2017 | Parshad | |
| 9,576,425 B2 | 2/2017 | Nguyen | |
| 9,580,031 B2 | 2/2017 | Kalis | |
| 9,613,491 B2 | 4/2017 | Roth | |
| 9,615,347 B1 | 4/2017 | Kerr | |
| 9,629,064 B2 | 4/2017 | Graves | |
| 9,659,444 B2 | 5/2017 | Norris | |
| 9,666,027 B2 | 5/2017 | Curtin | |
| D796,216 S | 9/2017 | Rockwell | |
| 9,756,607 B1 | 9/2017 | Deluca | |
| 9,786,123 B2 | 10/2017 | Huizinga | |
| 9,852,578 B2 | 12/2017 | Nelson | |
| D807,652 S | 1/2018 | Kawamoto | |
| 9,875,499 B2 | 1/2018 | Washington | |
| 9,875,607 B2 | 1/2018 | Nelson | |
| 9,881,444 B2 | 1/2018 | Nelson | |
| 9,928,502 B2 | 3/2018 | Curtin | |
| 9,928,689 B2 | 3/2018 | Walker | |
| 9,941,753 B2 | 4/2018 | Asanuma | |
| 9,961,507 B1 | 5/2018 | Mendelson | |
| 9,974,873 B2 | 5/2018 | Cole | |
| 9,974,875 B2 * | 5/2018 | Davis | A61L 2/10 |
| 9,999,699 B2 | 6/2018 | Sinai | |
| 10,009,868 B1 | 6/2018 | Reyes | |
| 10,013,850 B2 | 7/2018 | Nelson | |
| 10,032,334 B2 | 7/2018 | Cuddy | |
| 10,097,018 B2 | 10/2018 | Park | |
| 10,121,129 B2 | 11/2018 | Kalgi | |
| 10,121,318 B2 | 11/2018 | Lemay | |
| 10,121,319 B2 | 11/2018 | Radisich | |
| 10,131,432 B2 | 11/2018 | Simeon | |
| 10,134,223 B2 | 11/2018 | Mandava | |
| 10,134,234 B2 | 11/2018 | Lestrange | |
| 10,140,810 B1 | 11/2018 | Boyle | |
| 10,157,518 B2 | 12/2018 | Johnson | |
| 10,158,243 B2 | 12/2018 | Kim | |
| 10,192,400 B2 | 1/2019 | Price | |
| 10,192,401 B2 | 1/2019 | Nelson | |
| 10,198,906 B2 | 2/2019 | Walker | |
| 10,217,317 B2 | 2/2019 | Nelson | |
| 10,242,525 B1 | 3/2019 | Knust | |
| 10,242,530 B2 | 3/2019 | Arnone | |
| D848,159 S | 5/2019 | Hiyoshi | |
| D848,160 S | 5/2019 | Hiyoshi | |
| 10,282,939 B2 | 5/2019 | Yamaguchi | |
| 10,297,105 B2 | 5/2019 | Lemay | |
| 10,339,755 B2 | 7/2019 | Snow | |
| 10,360,761 B2 | 7/2019 | Higgins | |
| 10,360,763 B2 | 7/2019 | Higgins | |
| 10,373,430 B2 | 8/2019 | Higgins | |
| 10,380,843 B2 | 8/2019 | Higgins | |
| 10,417,867 B2 | 9/2019 | Nelson | |
| 10,453,297 B2 | 10/2019 | Lemay | |
| 10,456,488 B2 * | 10/2019 | Bilenko | A61L 2/10 |
| 10,460,560 B2 | 10/2019 | Cunningham, II | |
| 10,460,563 B2 | 10/2019 | Miri | |
| D870,473 S | 12/2019 | Hamilton | |
| 10,529,179 B2 | 1/2020 | Weiss | |
| 10,546,463 B2 | 1/2020 | Higgins | |
| D874,164 S | 2/2020 | Hamilton | |
| 10,573,129 B2 | 2/2020 | Higgins | |
| 10,621,826 B2 | 4/2020 | Higgins | |
| 10,643,426 B2 | 5/2020 | Higgins | |
| 10,699,527 B2 | 6/2020 | Higgins | |
| 10,706,683 B2 | 7/2020 | Higgins | |
| 10,720,016 B2 | 7/2020 | Nelson | |
| 10,726,668 B2 | 7/2020 | Nelson | |

(56) References Cited

U.S. PATENT DOCUMENTS

| | | |
|---|---|---|
| 10,755,520 B2 | 8/2020 | Moore |
| 10,769,885 B2 | 9/2020 | Hoehne |
| 10,783,416 B2 | 9/2020 | Shigeta |
| 11,011,020 B2 | 5/2021 | Springer |
| 11,024,088 B2 | 6/2021 | Heinen |
| 11,087,587 B2 | 8/2021 | Palmisano |
| 11,094,161 B2 | 8/2021 | Cleveland |
| 11,132,862 B2 | 9/2021 | Cleveland |
| 11,227,466 B2 | 1/2022 | Rousseau |
| D944,015 S | 2/2022 | Greenwood |
| 11,238,699 B2 | 2/2022 | Wingate |
| 11,276,271 B2 | 3/2022 | Taylor |
| 2002/0131445 A1 | 9/2002 | Skubic |
| 2005/0194827 A1 | 9/2005 | Dowty |
| 2006/0188389 A1* | 8/2006 | Levy .................. A61L 2/10 422/186.3 |
| 2006/0199648 A1 | 9/2006 | Mitchell |
| 2007/0090335 A1 | 4/2007 | Legrand |
| 2007/0117604 A1 | 5/2007 | Hill |
| 2008/0045342 A1 | 2/2008 | Crowder |
| 2008/0067417 A1* | 3/2008 | Lane .................. A61L 2/24 250/455.11 |
| 2008/0134601 A1 | 6/2008 | Cruz |
| 2008/0178774 A1 | 7/2008 | Saccani |
| 2008/0305855 A1 | 12/2008 | Czyzewski |
| 2009/0191933 A1 | 7/2009 | French |
| 2009/0218512 A1* | 9/2009 | Ranta .................. A61L 2/24 250/455.11 |
| 2009/0252646 A1 | 10/2009 | Holden |
| 2009/0317436 A1* | 12/2009 | Wilson ................ A61L 2/088 977/773 |
| 2010/0004051 A1 | 1/2010 | Walker |
| 2010/0104471 A1* | 4/2010 | Harmon .............. A61L 2/10 422/186.3 |
| 2010/0312625 A1 | 12/2010 | Miller |
| 2011/0173574 A1* | 7/2011 | Clavin ................ G06F 3/017 715/863 |
| 2011/0215261 A1* | 9/2011 | Lyslo .................. A61L 2/10 250/492.1 |
| 2011/0227391 A1 | 9/2011 | Cahall |
| 2011/0256019 A1* | 10/2011 | Gruen .................. A61L 2/10 345/173 |
| 2011/0306400 A1 | 12/2011 | Nguyen |
| 2012/0127083 A1* | 5/2012 | Kushler .............. G06F 3/04886 345/169 |
| 2012/0190455 A1 | 7/2012 | Briggs |
| 2012/0252564 A1 | 10/2012 | Moore |
| 2013/0023339 A1 | 1/2013 | Davis |
| 2013/0084991 A1 | 4/2013 | Lemay |
| 2013/0165232 A1 | 6/2013 | Nelson |
| 2013/0252713 A1 | 9/2013 | Nelson |
| 2013/0303263 A1 | 11/2013 | Lemay |
| 2014/0015478 A1 | 1/2014 | Von Novak |
| 2014/0021798 A1 | 1/2014 | Kesler |
| 2014/0031107 A1 | 1/2014 | Walker |
| 2014/0061509 A1* | 3/2014 | Shur .................. A23L 3/003 250/492.1 |
| 2014/0203770 A1 | 7/2014 | Salter |
| 2014/0228109 A1 | 8/2014 | Azuma |
| 2015/0044098 A1 | 2/2015 | Smart |
| 2015/0086968 A1 | 3/2015 | Kolavo |
| 2015/0090903 A1* | 4/2015 | Cole .................. A61L 2/24 250/492.1 |
| 2015/0228153 A1 | 8/2015 | Hedrick |
| 2015/0243133 A1 | 8/2015 | Nicholas |
| 2015/0254924 A1 | 9/2015 | Pececnik |
| 2016/0000951 A1 | 1/2016 | Kreiner |
| 2016/0027244 A1 | 1/2016 | Adiraju |
| 2016/0027249 A1 | 1/2016 | Nelson |
| 2016/0029155 A1 | 1/2016 | Kerr |
| 2016/0073218 A1 | 3/2016 | Shui |
| 2016/0092954 A1 | 3/2016 | Bassett |
| 2016/0098891 A1 | 4/2016 | Eby |
| 2016/0125319 A1 | 5/2016 | Morgan |
| 2016/0133089 A1 | 5/2016 | Roemer |
| 2016/0180656 A1 | 6/2016 | Loose |
| 2016/0183036 A1 | 6/2016 | Tung |
| 2016/0218545 A1 | 7/2016 | Schroeder |
| 2016/0234123 A1 | 8/2016 | Alisawi |
| 2016/0247354 A1 | 8/2016 | Arnone |
| 2016/0283989 A1 | 9/2016 | Esquilla, Jr. |
| 2016/0333578 A1 | 11/2016 | Ng |
| 2016/0349929 A1 | 12/2016 | Clemons |
| 2017/0026788 A1 | 1/2017 | Kostka |
| 2017/0076540 A1 | 3/2017 | Saffari |
| 2017/0076546 A1 | 3/2017 | Walker |
| 2017/0084086 A1 | 3/2017 | Pio |
| 2017/0092054 A1 | 3/2017 | Petersen |
| 2017/0092060 A1 | 3/2017 | Toohey |
| 2017/0092061 A1 | 3/2017 | Nelson |
| 2017/0109770 A1 | 4/2017 | Kusens |
| 2017/0111770 A1 | 4/2017 | Kusens |
| 2017/0169657 A1 | 6/2017 | Keilwert |
| 2017/0213632 A1 | 7/2017 | Ozana |
| 2017/0278347 A1 | 9/2017 | Kukita |
| 2017/0279495 A1 | 9/2017 | Kim |
| 2017/0289154 A1 | 10/2017 | Krieger |
| 2017/0346919 A1 | 11/2017 | He |
| 2018/0005484 A1 | 1/2018 | Michel |
| 2018/0033244 A1 | 2/2018 | Northrup |
| 2018/0061179 A1 | 3/2018 | Miri |
| 2018/0075690 A1 | 3/2018 | Moore |
| 2018/0108213 A1 | 4/2018 | Sanford |
| 2018/0194471 A1 | 7/2018 | Merrick |
| 2018/0357850 A1 | 12/2018 | Moore |
| 2019/0066441 A1 | 2/2019 | Lestrange |
| 2019/0073873 A1 | 3/2019 | Lemay |
| 2019/0088076 A1 | 3/2019 | Rajendran |
| 2019/0096175 A1 | 3/2019 | Higgins |
| 2019/0096180 A1 | 3/2019 | Petersen |
| 2019/0102985 A1 | 4/2019 | Higgins |
| 2019/0139356 A1 | 5/2019 | Moya Garcia |
| 2019/0151752 A1 | 5/2019 | Kim |
| 2019/0164384 A1 | 5/2019 | Soukup |
| 2019/0172300 A1 | 6/2019 | Phillips |
| 2019/0188951 A1 | 6/2019 | Nelson |
| 2019/0188961 A1 | 6/2019 | Higgins |
| 2019/0188962 A1 | 6/2019 | Higgins |
| 2019/0188963 A1 | 6/2019 | Higgins |
| 2019/0197526 A1 | 6/2019 | Higgins |
| 2019/0197822 A1 | 6/2019 | Shepherd |
| 2019/0197830 A1 | 6/2019 | Petersen |
| 2019/0205866 A1 | 7/2019 | Higgins |
| 2019/0244476 A1 | 8/2019 | Miltenberger |
| 2019/0272704 A1 | 9/2019 | Lemay |
| 2019/0325701 A1 | 10/2019 | Higgins |
| 2020/0005595 A1 | 1/2020 | Nelson |
| 2020/0043284 A1 | 2/2020 | Lemay |
| 2020/0058190 A1 | 2/2020 | Cunningham, II |
| 2020/0111319 A1 | 4/2020 | Palmisano |
| 2020/0134973 A1 | 4/2020 | Higgins |
| 2020/0152005 A1 | 5/2020 | Higgins |
| 2020/0226881 A1 | 7/2020 | Warner |
| 2020/0302740 A1 | 9/2020 | Cleveland |
| 2020/0302746 A1 | 9/2020 | Cleveland |
| 2021/0019987 A1 | 1/2021 | Cohen |
| 2021/0241575 A1 | 8/2021 | Shepherd |
| 2021/0295636 A1 | 9/2021 | Cleveland |
| 2021/0316022 A1* | 10/2021 | Ciesiun ............. A61L 2/10 |
| 2021/0386201 A1 | 12/2021 | Wilson |
| 2022/0019950 A1 | 1/2022 | Sabri |
| 2022/0031883 A1* | 2/2022 | Baarman .......... A23L 3/28 |
| 2022/0092908 A1 | 3/2022 | Cleveland |
| 2022/0148380 A1 | 5/2022 | Wingate |
| 2022/0319272 A1 | 10/2022 | Shepherd |

FOREIGN PATENT DOCUMENTS

| | | | |
|---|---|---|---|
| CA | 2716403 A1 * | 9/2009 | ............ G06F 3/005 |
| EP | 0979604 A1 | 2/2000 | |
| EP | 3280643 B1 | 4/2020 | |
| GB | 2273088 A | 6/1994 | |
| GB | 2421217 A * | 6/2006 | ............... A61L 2/10 |

(56) References Cited

FOREIGN PATENT DOCUMENTS

| GB | 2421220 | A | * | 6/2006 | | A61L 2/10 |
|---|---|---|---|---|---|---|
| GB | 2422807 | A | * | 8/2006 | | A61L 2/10 |
| GB | 4010756 | | | 4/2009 | | |
| KR | 200353613 | Y1 | * | 6/2004 | | |
| KR | 20090059283 | A | | 6/2009 | | |
| WO | 1999059451 | A1 | | 11/1999 | | |
| WO | 2017196732 | A1 | | 11/2017 | | |

OTHER PUBLICATIONS

Office Action (Non-Final Rejection) dated Nov. 10, 2021 for U.S. Appl. No. 16/585,838 (pp. 1-13).
Office Action (Notice of Allowance and Fees Due (PTOL-85)) dated Nov. 22, 2021 for U.S. Appl. No. 17/220,778 (pp. 1-8).
Office Action (Non-Final Rejection) dated Mar. 8, 2022 for U.S. Appl. No. 17/262,178 (pp. 1-9).
Office Action (Notice of Allowance and Fees Due (PTOL-85)) dated Mar. 4, 2022 for U.S. Appl. No. 16/585,838 (pp. 1-7).
Office Action (Notice of Allowance and Fees Due (PTOL-85)) dated May 18, 2022 for U.S. Appl. No. 17/262,178 (pp. 1-7).
Office Action (Notice of Allowance and Fees Due (PTOL-85)) dated Sep. 20, 2023 for U.S. Appl. No. 17/491,348 (pp. 1-5).
Office Action (Notice of Allowance and Fees Due (PTOL-85)) dated Oct. 2, 2023 for U.S. Appl. No. 17/347,321 (pp. 1-6).
Office Action (Notice of Allowance and Fees Due (PTOL-85)) dated Nov. 22, 2023 for U.S. Appl. No. 17/941,493 (pp. 1-8).
Office Action (Notice of Allowance and Fees Due (PTOL-85)) dated Nov. 27, 2023 for U.S. Appl. No. 18/061,979 (pp. 1-8).
Office Action (Notice of Allowance and Fees Due (PTOL-85)) dated May 18, 2023 for U.S. Appl. No. 17/368,393 (pp. 1-5).
Office Action (Final Rejection) dated May 26, 2023 for U.S. Appl. No. 17/347,321 (pp. 1-26).
Office Action (Notice of Allowance and Fees Due (PTOL-85)) dated Jun. 8, 2023 for U.S. Appl. No. 17/219,634 (pp. 1-7).
Office Action (Notice of Allowance and Fees Due (PTOL-85)) dated Jun. 28, 2023 for U.S. Appl. No. 17/674,672 (pp. 1-8).
Office Action (Non-Final Rejection) dated Jul. 25, 2023 for U.S. Appl. No. 18/061,979 (pp. 1-6).
Office Action (Notice of Allowance and Fees Due (PTOL-85)) dated Aug. 22, 2023 for U.S. Appl. No. 17/647,568 (pp. 1-8).
Australian Examination Report No. 1 for App. No. AU2022204879, dated Sep. 7, 2023, (1-3 pages).
Notice of Allowance dated Jun. 24, 2022 for U.S. Appl. No. 29/734,939 (pp. 1-10).
"Shields for Casino Slots" Apr. 28, 2020, ReviewJournal, visited Jun. 7, 2022: https://www.reviewjournal.com/business/(casinos-gaming/las-vegas-firm-creates-safety-shields-for-use-at-casino-slots-tables-2016807/ (Year:2020).
"SuzoHapp" Jan. 14, 2020, Ggrasia, site visited Jun. 7, 2022: https://www.ggrasia.com/ suzohapp-offers-acrylic-dividers-for-gaming-venues/ (Year:2020).
"Protective Separators" Oct. 22, 2020, Needs Info Including URL Starting With veb.archive.org/ (Year: 2020).
Stabile, Angelica, "Las Vegas startup creates coronavirus self-cleaning slot machine dividers" May 5, 2020, Fox Business, site visited Jun. 9, 2022: https://www.foxbusiness.com/technology/las-vegas-company-coronavirus-slot-machine-dividers (Year:2020).
Office Action (Notice of Allowance and Fees Due (PTOL-85)) dated Aug. 16, 2022 for U.S. Appl. No. 17/211,521 (pp. 1-8).
Australian Examination Report No. 1 issued in App. No. AU2021202860, dated Jul. 19, 2022, 3 pages.
Office Action (Notice of Allowance and Fees Due (PTOL-85)) dated Sep. 23, 2022 for U.S. Appl. No. 17/262,178 (pp. 1-7).
Office Action (Non-Final Rejection) dated Dec. 6, 2022 for U.S. Appl. No. 17/352,049 (pp. 1-8).
Office Action (Non-Final Rejection) dated Dec. 30, 2022 for U.S. Appl. No. 17/351,920 (pp. 1-8).
Office Action (Non-Final Rejection) dated Jan. 17, 2023 for U.S. Appl. No. 17/347,321 (pp. 1-22).
Office Action (Non-Final Rejection) dated Jan. 23, 2023 for U.S. Appl. No. 17/368,393 (pp. 1-6).
Office Action (Notice of Allowance and Fees Due (PTOL-85)) dated Jan. 20, 2023 for U.S. Appl. No. 17/362,486 (pp. 1-8).
Office Action (Notice of Allowance and Fees Due (PTOL-85)) dated Jan. 23, 2023 for U.S. Appl. No. 17/362,530 (pp. 1-9).
Office Action (Notice of Allowance and Fees Due (PTOL-85)) dated Jan. 30, 2023 for U.S. Appl. No. 17/362,486 (pp. 1-2).
Office Action (Notice of Allowance and Fees Due (PTOL-85)) dated Feb. 1, 2023 for U.S. Appl. No. 17/362,530 (pp. 1-2).
Office Action (Non-Final Rejection) dated Feb. 9, 2023 for U.S. Appl. No. 17/674,672 (pp. 1-6).
Office Action (Notice of Allowance and Fees Due (PTOL-85)) dated Feb. 21, 2023 for U.S. Appl. No. 17/351,920 (pages.
Office Action (Notice of Allowance and Fees Due (PTOL-85)) dated Mar. 13, 2023 for U.S. Appl. No. 17/343,344 (pp. 1-5).
Office Action (Final Rejection) dated Mar. 17, 2023 for U.S. Appl. No. 17/219,634 (pp. 1-15).
Office Action (Notice of Allowance and Fees Due (PTOL-85)) dated Mar. 27, 2023 for U.S. Appl. No. 17/352,049 (pp. 1-5).
Office Action (Non-Final Rejection) dated Apr. 7, 2023 for U.S. Appl. No. 17/647,568 (pp. 1-6).
Office Action (Non-Final Rejection) dated Apr. 25, 2023 for U.S. Appl. No. 17/491,348 (pp. 1-12).
Office Action dated Sep. 25, 2020 for U.S. Appl. No. 16/264,875 (pp. 1-12).
AU Examination Report for AU Application No. 2018204598, dated Mar. 20, 2019. 5 pages.
Office Action dated Apr. 29, 2020 for U.S. Appl. No. 16/264,875 (pp. 1-8).
Notice of Allowance dated Jan. 7, 2021 for U.S. Appl. No. 16/264,875 (pp. 1-7).
Australian Examination Report No. 1 for App. No. AU2020204407, dated Mar. 23, 2021, 4 pages.
Office Action dated Nov. 2, 2020 for U.S. Appl. No. 16/586,168 (pp. 1-7).
Notice of Allowance dated Dec. 2, 2020 for U.S. Appl. No. 16/586,246 (pp. 1-10).
Office Action dated Dec. 2, 2020 for U.S. Appl. No. 16/586,356 (pp. 1-7).
Notice of Allowance dated Feb. 11, 2021 for U.S. Appl. No. 16/586,127 (pp. 1-15).
Notice of Allowance dated Feb. 12, 2021 for U.S. Appl. No. 16/586,168 (pp. 1-5).
International Search Report and Written Opinion for App. No. PCT/US19/53823, dated Jan. 3, 2020, 10 pages.
Corrected Notice of Allowability dated Apr. 14, 2021 for U.S. Appl. No. 16/586,127 (pp. 1-2).
Notice of Allowance dated Apr. 13, 2021 for U.S. Appl. No. 16/586,356 (pp. 1-5).
Notice of Allowance dated Apr. 29, 2021 for U.S. Appl. No. 16/586,168 (pp. 1-5).
Eddystone format, https://developers.google.com/beacons/eddystone, printed Feb. 3, 2021, 9 pages.
RadBeacon Serial Port Interface, v3.2.3, 56 pages.
Notice of Allowance dated May 26, 2021 for U.S. Appl. No. 16/586,246 (pp. 1-5).
Office Action (Non-Final Rejection) dated Nov. 8, 2022 for U.S. Appl. No. 17/343,344 (pp. 1-7).
Office Action (Notice of Allowance and Fees Due (PTOL-85) dated Nov. 16, 2022 for U.S. Appl. No. 17/211,521 (pp. 1-8).
Office Action (Notice of Allowance and Fees Due (PTOL-85)) dated Feb. 8, 2024 for U.S. Appl. No. 17/819,523 (pp. 1-7).
Office Action (Notice of Allowance and Fees Due (PTOL-85)) dated Feb. 15, 2024 for U.S. Appl. No. 18/061,979 (pp. 1-8).

\* cited by examiner

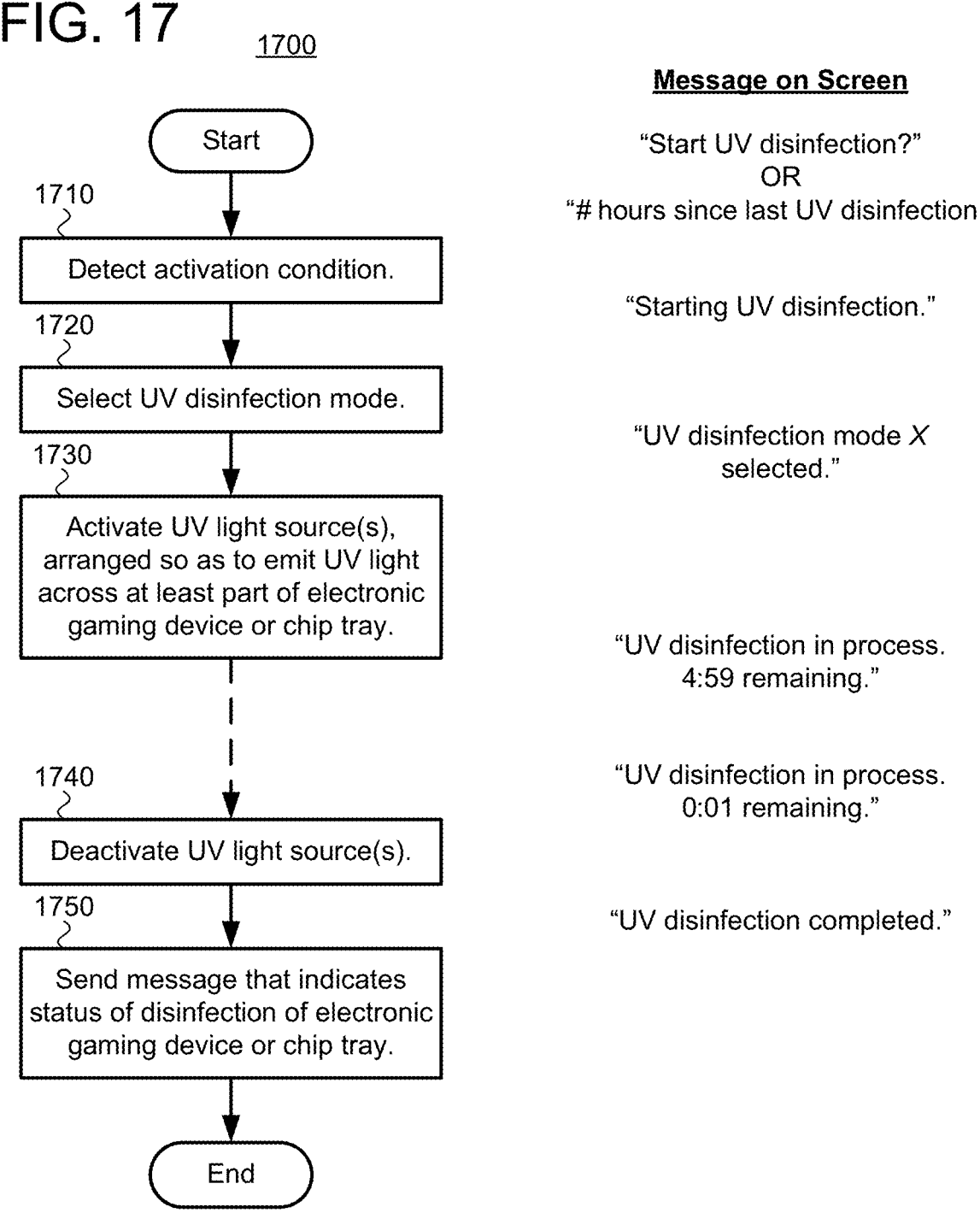

ULTRAVIOLET DISINFECTION AND SANITIZING SYSTEMS AND METHODS FOR ELECTRONIC GAMING DEVICES AND OTHER GAMING EQUIPMENT

CROSS-REFERENCE TO RELATED APPLICATIONS

This application claims the benefit of U.S. Provisional Patent Application Ser. No. 63/018,500, filed on 30 Apr. 2020, by Coppola, et al. and entitled ULTRAVIOLET DISINFECTION OF ELECTRONIC GAMING DEVICES AND OTHER GAMING EQUIPMENT, the entire disclosure of which is incorporated by reference herein.

This application further claims the benefit of U.S. Provisional Patent Application Ser. No. 63/026,557, filed on 18 May 2020, by Urban, et al. and entitled SANITIZING SYSTEMS AND METHODS FOR GAMING MACHINES AND ENVIRONMENTS, the entire disclosure of which is incorporated by reference herein.

FIELD

Electronic gaming devices and other gaming equipment include, or are retrofitted with, ultraviolet ("UV") light sources to disinfect surfaces as well as hardware features and software features to manage UV disinfection cycles and report results of UV disinfection cycles.

BACKGROUND

Electronic gaming machines ("EGMs") or gaming devices may have surfaces and areas where players contact that should be sanitized. Bacterial (e.g., *Streptococcus, Pseudomonas*, MRSA), fungal (e.g., *Aspergillus*) and viral (e.g., SARS-CoV-2, smallpox, influenza, mumps, measles, chickenpox, Ebola, HIV, and rubella) pathogens may pose potential health risks due to rapid transmission among casino patrons, where suitable protective measures are not employed. Sanitizing such devices may minimize the spread, or the risk of spread, of disease. Some diseases are infectious, and their transmission in casinos around gaming machines may be a concern, both to the person and the public. While casinos may have building filtration that may help reduce some risks, treatment of EGM surfaces may have central role in minimizing transmission of disease in casinos. To date, there is room for improvement in effective and efficient technology to suitably sanitize EGM surfaces.

EGMs provide a variety of wagering games such as slot games, video poker games, video blackjack games, roulette games, video bingo games, keno games and other types of games that are frequently offered at casinos and other locations. Play on EGMs typically involves a player establishing a credit balance by inputting money, or another form of monetary credit, and placing a monetary wager (from the credit balance) on one or more outcomes of an instance (or single play) of a primary or base game. In some cases, a player may qualify for a special mode of the base game, a secondary game, or a bonus round of the base game by attaining a certain winning combination or triggering event in, or related to, the base game, or after the player is randomly awarded the special mode, secondary game, or bonus round. In the special mode, secondary game, or bonus round, the player is given an opportunity to win extra game credits, game tokens or other forms of payout. In the case of "game credits" that are awarded during play, the game credits are typically added to a credit meter total on the EGM and can be provided to the player upon completion of a gaming session or when the player wants to "cash out."

"Slot" type games are often displayed to the player in the form of various symbols arrayed in a row-by-column grid or matrix. Specific matching combinations of symbols along predetermined paths (or paylines) through the matrix indicate the outcome of the game. The display typically highlights winning combinations/outcomes for identification by the player. Matching combinations and their corresponding awards are usually shown in a "pay-table" which is available to the player for reference. Often, the player may vary his/her wager to include differing numbers of paylines and/or the amount bet on each line. By varying the wager, the player may sometimes alter the frequency or number of winning combinations, frequency or number of secondary games, and/or the amount awarded.

Typical games use a random number generator ("RNG") to randomly determine the outcome of each game. The game is designed to return a certain percentage of the amount wagered back to the player over the course of many plays or instances of the game, which is generally referred to as return to player ("RTP"). The RTP and randomness of the RNG ensure the fairness of the games and are highly regulated. Upon initiation of play, the RNG randomly determines a game outcome and symbols are then selected which correspond to that outcome. Notably, some games may include an element of skill on the part of the player and are therefore not entirely random.

An EGM is often placed in a high-traffic area of a casino or other location, with many people using, touching, or otherwise interacting with the EGM every day, and many other people passing near the EGM every day. A person using the EGM typically touches surfaces of the EGM such as a button deck (including buttons and surrounding areas) and touchscreen display.

The surfaces of the EGM can harbor pathogens such as bacteria and viruses from previous users of the EGM. Cleaning personnel can remove some of these pathogens by spraying and wiping down frequently-touched surfaces, but such disinfection activities can be labor-intensive and time-consuming. Also, it can be challenging to provide disinfection "on demand" to a player requesting service or an EGM needing service, and it can be inconvenient for the player to personally disinfect the EGM. Spraying and wiping down frequently-touched surfaces of the EGM can leave residue on the surfaces, which detracts from the gaming experience. Also, liquid from spraying and wiping down surfaces of the EGM can seep through gaps on or around the surfaces, which may corrode, tarnish, "gum up," or otherwise harm electronic components and mechanical components underneath. Finally, some pathogens may be resistant to disinfection that uses spraying and wiping with standard treatments.

SUMMARY

In summary, the detailed description presents innovations in electronic gaming devices and other gaming equipment that include ultraviolet ("UV") light sources to disinfect surfaces as well as hardware features and software features to manage UV disinfection cycles and report results of UV disinfection cycles. The detailed description also presents innovations in electronic gaming devices and other gaming equipment that are retrofitted with UV light sources to disinfect surfaces. In some implementations, these innovations can effectively remove pathogens such as bacteria and viruses from surfaces of an electronic gaming device or other gaming equipment, without leaving residue on the surfaces that may detract from the gaming experience, and without the risk of liquid seeping through gaps on or around the surfaces to harm components underneath. The innovations can be used in combination with conventional disinfection operations (such as spraying and wiping down surfaces) or used separately. Either way, the innovations can provide cost-effective and timely UV disinfection. For example, in some implementations, UV light sources at the edges of high-touch surfaces such as a button deck or touchscreen display effectively provide UV disinfection in a relatively unobtrusive way. The UV light sources can be activated on demand or during idle times between persons using an electronic gaming device, to provide a quick UV disinfection. Or, the UV light sources can be activated during off-hours for a more thorough UV disinfection, e.g., over a longer duration, with higher-intensity UV light, and/or with shorter wavelength UV light. By controlling activation of the UV light sources, UV disinfection can be performed safely, limiting exposure to UV radiation that might cause skin damage or retinal damage, and effectively, without leaving residue on surfaces or otherwise detracting from the gaming experience.

The innovations described herein include, but are not limited to, the innovations defined by the claims at the end of the present application.

The innovations can be implemented as part of a method, as part of an electronic gaming device such as an electronic gaming device or electronic gaming server configured to perform the method, or as part of non-transitory computer-readable media storing computer-executable instructions for causing one or more processors in a computer system to perform the method. The various innovations can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures and illustrates a number of examples. Examples may also be capable of other and different applications, and some details may be modified in various respects all without departing from the spirit and scope of the disclosed innovations.

BRIEF DESCRIPTION OF THE DRAWINGS

FIG. 17 illustrates an example technique for managing UV disinfection of an electronic gaming device or other gaming equipment.

DETAILED DESCRIPTION

Figure 1:
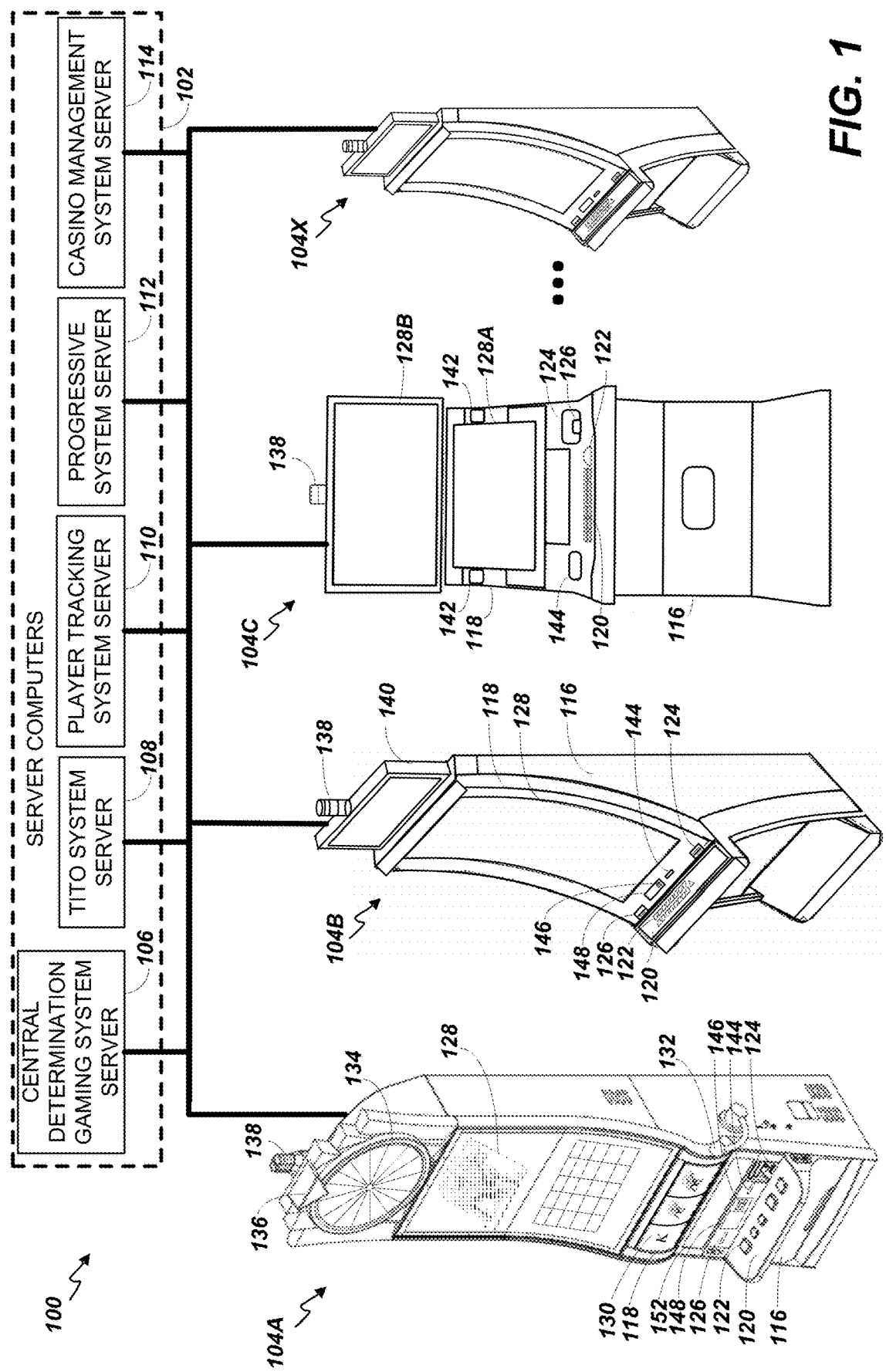
FIG. 1 is an exemplary diagram showing several electronic gaming devices networked with various gaming related servers.

Innovations in electronic gaming devices and other gaming equipment that include contactless cleaning and/or operations (via automatically controlled systems, contactless control techniques, etc.), which may employ configurable arrays of ultraviolet ("UV") light sources to provide non-contact disinfecting of various surfaces of the gaming environment. These innovations therefore provide timely and/or on-demand disinfecting of surfaces and/or objects, in many cases without the need for staff personnel.

These innovations may further include hardware features and software features to manage UV disinfection cycles and report results of UV disinfection cycles, which are described herein. Innovations in electronic gaming devices and other gaming equipment that are retrofitted with UV light sources to disinfect surfaces are also described herein. In some implementations, these innovations can effectively remove pathogens such as bacteria and viruses from surfaces of an electronic gaming device or other gaming equipment. For example, in some implementations, UV light sources at the edges of high-touch surfaces such as a button deck or touchscreen display effectively provide UV disinfection in a relatively unobtrusive way. UV disinfection can effectively disinfect surfaces without leaving residue on the surfaces and without the risk of liquid seeping through gaps on or around the surfaces to harm components underneath.

The UV light sources can be activated on demand or during idle times between persons using an electronic gaming device, to provide a quick UV disinfection. Or, the UV light sources can be activated during a forced-idle time (e.g., imposed by a system server to lock users out of electronic gaming devices near an in-use electronic gaming device and thereby promote "social distancing" between users), to provide a quick UV disinfection. Or, the UV light sources can be activated during off-hours for a more thorough UV disinfection, e.g., over a longer duration, with higher-intensity UV light, and/or with shorter wavelength UV light.

By controlling activation of the UV light sources, UV disinfection can be performed safely, limiting exposure to UV radiation that might cause skin damage or retinal damage. Further, by controlling activation of the UV light sources, UV disinfection can be performed effectively, without leaving residue on surfaces or otherwise detracting from the gaming experience.

The innovations can be used in combination with conventional disinfection operations (such as spraying and wiping down surfaces) or used separately. Either way, the innovations can provide cost-effective and timely UV disinfection.

Various other features of disinfection technologies, sterilization technologies, and contactless interaction technologies for electronic gaming devices are also described herein.

In the examples described herein, identical reference numbers in different figures indicate an identical component, module, or operation. More generally, various alternatives to the examples described herein are possible. For example, some of the methods described herein can be altered by changing the ordering of the method acts described, by splitting, repeating, or omitting certain method acts, etc. The various aspects of the disclosed technology can be used in combination or separately. Some of the innovations described herein address one or more of the problems noted in the background. Typically, a given technique/tool does not solve all such problems. It is to be understood that other examples may be utilized and that structural, logical, software, hardware, and electrical changes may be made without departing from the scope of the disclosure. The following description is, therefore, not to be taken in a limited sense.

I. Example Electronic Gaming Servers and Electronic Gaming Devices.

FIG. 1 illustrates several different models of electronic gaming devices which may be networked to various gaming related servers. Shown is a system 100 in a gaming environment including one or more server computers 102 (e.g., slot servers of a casino) that are in communication, via a communications network, with one or more gaming devices 104A-104X (electronic gaming machines ("EGMs"), slots, video poker, bingo machines, etc.) that can implement one or more aspects of the present disclosure. The gaming devices 104A-104X may alternatively be portable and/or remote gaming devices such as, but not limited to, a smart phone, a tablet, a laptop, or a game console. Gaming devices 104A-104X utilize specialized software and/or hardware to form non-generic, particular machines or apparatuses that comply with regulatory requirements regarding devices used for wagering or games of chance that provide monetary awards.

Communication between the gaming devices 104A-104X and the server computers 102, and among the gaming devices 104A-104X, may be direct or indirect using one or more communication protocols. As an example, gaming devices 104A-104X and the server computers 102 can communicate over one or more communication networks, such as over the Internet through a website maintained by a computer on a remote server or over an online data network including commercial online service providers, Internet service providers, private networks (e.g., local area networks and enterprise networks), and the like (e.g., wide area networks). The communication networks could allow gaming devices 104A-104X to communicate with one another and/or the server computers 102 using a variety of communication-based technologies, such as radio frequency (RF) (e.g., wireless fidelity (WiFi®) and Bluetooth®), cable TV, satellite links and the like.

In some implementation, server computers 102 may not be necessary and/or preferred. For example, in one or more implementations, a stand-alone gaming device such as gaming device 104A, gaming device 104B or any of the other gaming devices 104C-104X can implement one or more aspects of the present disclosure. However, it is typical to find multiple electronic gaming devices connected to networks implemented with one or more of the different server computers 102 described herein.

The server computers 102 may include a central determination gaming system server 106, a ticket-in-ticket-out (TITO) system server 108, a player tracking system server 110, a progressive system server 112, and/or a casino management system server 114. Gaming devices 104A-104X may include features to enable operation of any or all servers for use by the player and/or operator (e.g., the casino, resort, gaming establishment, tavern, pub, etc.). For example, game outcomes may be generated on a central determination gaming system server 106 and then transmitted over the network to any of a group of remote terminals or remote gaming devices 104A-104X that utilize the game outcomes and display the results to the players.

Gaming device 104A is often of a cabinet construction which may be aligned in rows or banks of similar devices for placement and operation on a casino floor. The gaming device 104A often includes a main door which provides access to the interior of the cabinet. Gaming device 104A typically includes a button area or button deck 120 accessible by a player that is configured with input switches or buttons 122, an access channel for a bill validator 124, and/or an access channel for a ticket-out printer 126.

In FIG. 1, gaming device 104A is shown as a Relm XL™ model gaming device manufactured by Aristocrat® Technologies, Inc. As shown, gaming device 104A is a reel machine having a gaming display area 118 comprising a number (typically 3 or 5) of mechanical reels 130 with various symbols displayed on them. The mechanical reels 130 are independently spun and stopped to show a set of symbols within the gaming display area 118 which may be used to determine an outcome to the game.

In many configurations, the gaming device 104A may have a main display 128 (e.g., video display monitor) mounted to, or above, the gaming display area 118. The main display 128 can be a high-resolution liquid crystal display (LCD), plasma, light emitting diode (LED), or organic light emitting diode (OLED) panel which may be flat or curved as shown, a cathode ray tube, or other conventional electronically controlled video monitor. The main display 128 can be a touchscreen display or non-touchscreen display.

In some implementations, the bill validator 124 may also function as a "ticket-in" reader that allows the player to use a casino issued credit ticket to load credits onto the gaming device 104A (e.g., in a cashless ticket ("TITO") system). In such cashless implementations, the gaming device 104A may also include a "ticket-out" printer 126 for outputting a credit ticket when a "cash out" button is pressed. Cashless TITO systems are used to generate and track unique barcodes or other indicators printed on tickets to allow players to avoid the use of bills and coins by loading credits using a ticket reader and cashing out credits using a ticket-out printer 126 on the gaming device 104A. The gaming device 104A can have hardware meters for purposes including ensuring regulatory compliance and monitoring the player credit balance. In addition, there can be additional meters that record the total amount of money wagered on the gaming device, total amount of money deposited, total amount of money withdrawn, total amount of winnings on gaming device 104A.

In some implementations, a player tracking card reader 144, a transceiver for wireless communication with a mobile device (e.g., a player's smartphone), a keypad 146, and/or an illuminated display 148 for reading, receiving, entering, and/or displaying player tracking information is provided in gaming device 104A. The illuminated display 148 can be a touchscreen display or non-touchscreen display. In such implementations, a game controller within the gaming device 104A can communicate with the player tracking system server 110 to send and receive player tracking information.

Gaming device 104A may also include a bonus topper wheel 134. When bonus play is triggered (e.g., by a player achieving a particular outcome or set of outcomes in the primary game), bonus topper wheel 134 is operative to spin and stop with indicator arrow 136 indicating the outcome of the bonus game. Bonus topper wheel 134 is typically used to play a bonus game, but it could also be incorporated into play of the base or primary game.

A candle 138 may be mounted on the top of gaming device 104A and may be activated by a player (e.g., using a switch or one of buttons 122) to indicate to operations staff that gaming device 104A has experienced a malfunction or the player requires service. The candle 138 is also often used to indicate a jackpot has been won and to alert staff that a hand payout of an award may be needed.

There may also be one or more information panels 152 which may be a back-lit, silkscreened glass panel with lettering to indicate general game information including, for example, a game denomination (e.g., $0.25 or $1), pay lines, pay tables, and/or various game related graphics. In some implementations, the information panel(s) 152 may be implemented as an additional video display.

Gaming devices 104A have traditionally also included a handle 132 typically mounted to the side of main cabinet 116 which may be used to initiate game play.

Figure 2A:
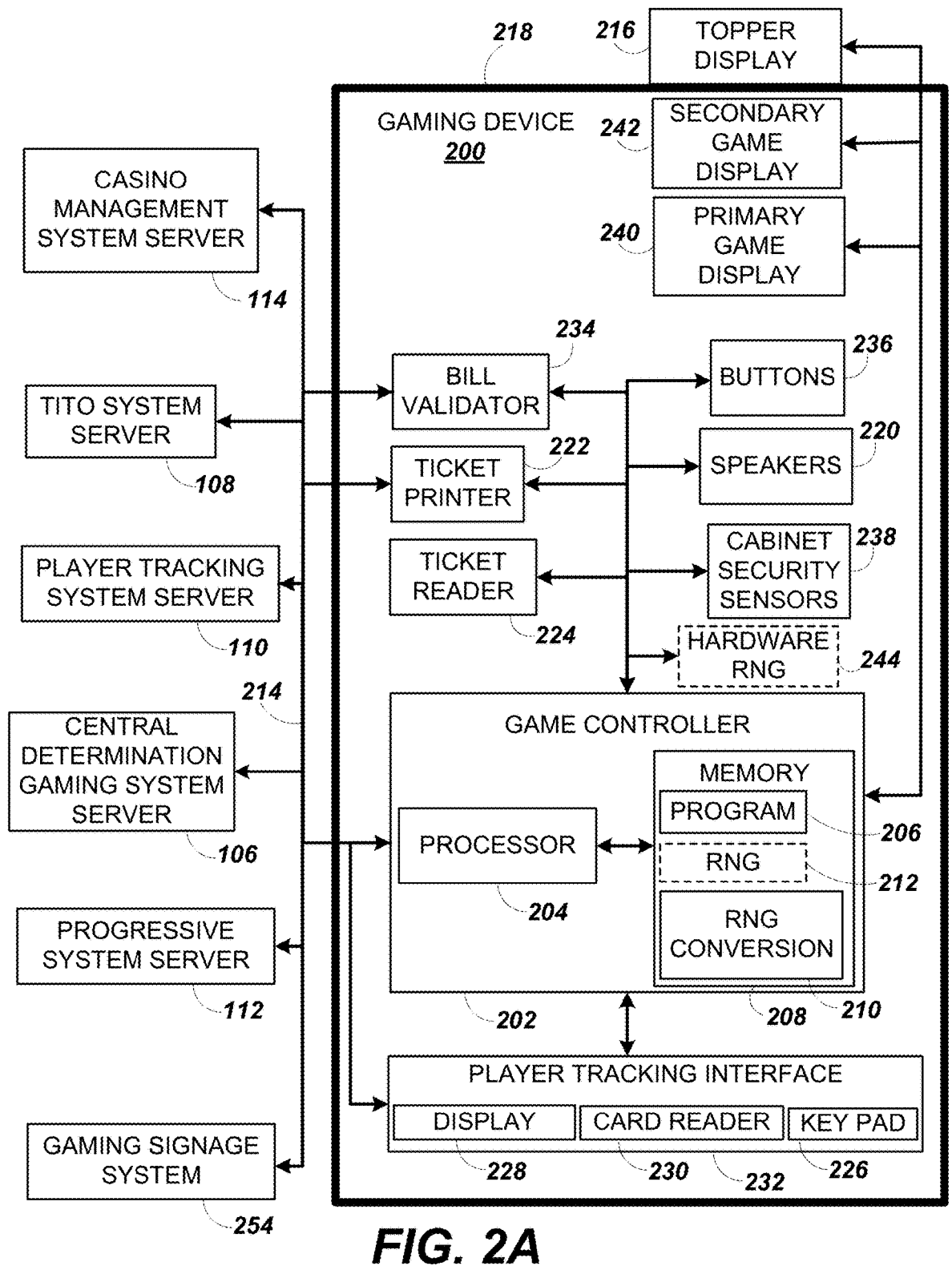
FIG. 2A is a block diagram showing various functional elements of an exemplary electronic gaming device.

Many or all the above described components can be controlled by circuitry (e.g., a game controller) housed inside the main cabinet 116 of the gaming device 104A, the details of which are shown in FIG. 2A.

An alternative example gaming device 104B illustrated in FIG. 1 is the Arc™ model gaming device manufactured by Aristocrat® Technologies, Inc. Note that where possible, reference numerals identifying similar features of the gaming device 104A implementation are also identified in the gaming device 104B implementation using the same reference numbers. Gaming device 104B does not include physical reels and instead shows game play functions on main display 128. An optional topper screen 140 may be used as a secondary game display for bonus play, to show game features or attraction activities while a game is not in play, or any other information or media desired by the game designer or operator. In some implementations, the optional topper screen 140 may also or alternatively be used to display progressive jackpot prizes available to a player during play of gaming device 104B.

Example gaming device 104B includes a main cabinet 116 including a main door which opens to provide access to the interior of the gaming device 104B. The main or service door is typically used by service personnel to refill the ticket-out printer 126 and collect bills and tickets inserted into the bill validator 124. The main or service door may also be accessed to reset the machine, verify and/or upgrade the software, and for general maintenance operations.

Another example gaming device 104C shown is the Helix™ model gaming device manufactured by Aristocrat® Technologies, Inc. Gaming device 104C includes a main display 128A that is in a landscape orientation. Although not illustrated by the front view provided, the main display 128A may have a curvature radius from top to bottom, or alternatively from side to side. In some implementations, main display 128A is a flat panel display. The main display 128A can be a touchscreen display or non-touchscreen display. Main display 128A is typically used for primary game play while secondary display 128B is typically used for bonus game play, to show game features or attraction activities while the game is not in play or any other information or media desired by the game designer or operator. The secondary display 128B can be a touchscreen display or non-touchscreen display. In some implementations, example gaming device 104C may also include speakers 142 to output various audio such as game sound, background music, etc.

Many different types of games, including mechanical slot games, video slot games, video poker, video blackjack, video pachinko, keno, bingo, and lottery, may be provided with or implemented within the depicted gaming devices 104A-104C and other similar gaming devices. Each gaming device may also be operable to provide many different games. Games may be differentiated according to themes, sounds, graphics, type of game (e.g., slot game vs. card game vs. game with aspects of skill), denomination, number of paylines, maximum jackpot, progressive or non-progressive, bonus games, and may be deployed for operation in Class 2 or Class 3, etc.

FIG. 2A is a block diagram depicting exemplary internal electronic components of a gaming device 200 connected to various external systems. All or parts of the gaming device 200 shown could be used to implement any one of the example gaming devices 104A-X depicted in FIG. 1. As shown in FIG. 2A, gaming device 200 includes a topper display 216 or another form of a top box (e.g., a topper wheel, a topper screen, etc.) that sits above cabinet 218. Cabinet 218 or topper display 216 may also house a number of other components which may be used to add features to a game being played on gaming device 200, including speakers 220, a ticket printer 222 which prints bar-coded tickets or other media or mechanisms for storing or indicating a player's credit value, a ticket reader 224 which reads bar-coded tickets or other media or mechanisms for storing or indicating a player's credit value, and a player tracking interface 232. Player tracking interface 232 may include a keypad 226 for entering information, a player tracking display 228 for displaying information (e.g., an illuminated or video display, which may be a touchscreen display), a card reader 230 for receiving data and/or communicating information to and from media or a device such as a smart phone enabling player tracking. FIG. 2 also depicts utilizing a ticket printer 222 to print tickets for a TITO system server 108. Gaming device 200 may further include a bill validator 234, player-input buttons 236 for player input, cabinet security sensors 238 to detect unauthorized opening of the cabinet 218, a primary game display 240, and a secondary game display 242, each coupled to and operable under the control of game controller 202. The primary game display 240 and/or the secondary game display 242 can be a touchscreen display or non-touchscreen display.

The games available for play on the gaming device 200 are controlled by a game controller 202 that includes one or more processors 204. Processor 204 represents a general-purpose processor, a specialized processor intended to perform certain functional tasks, or a combination thereof. As an example, processor 204 can be a central processing unit (CPU) that has one or more multi-core processing units and memory mediums (e.g., cache memory) that function as buffers and/or temporary storage for data. Alternatively, processor 204 can be a specialized processor, such as an application specific integrated circuit (ASIC), graphics processing unit (GPU), field-programmable gate array (FPGA), digital signal processor (DSP), or another type of hardware accelerator. In another example, processor 204 is a system on chip (SoC) that combines and integrates one or more general-purpose processors and/or one or more specialized processors. Although FIG. 2A illustrates that game controller 202 includes a single processor 204, game controller 202 is not limited to this representation and instead can include multiple processors 204 (e.g., two or more processors).

FIG. 2A illustrates that processor 204 is operatively coupled to memory 208. Memory 208 is defined herein as including volatile and nonvolatile memory and other types of non-transitory data storage components. Volatile memory is memory that do not retain data values upon loss of power. Nonvolatile memory is memory that do retain data upon a loss of power. Examples of memory 208 include random access memory (RAM), read-only memory (ROM), hard disk drives, solid-state drives, universal serial bus (USB) flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, examples of RAM include static random access memory (SRAM), dynamic random access memory (DRAM), magnetic random access memory (MRAM), and other such devices. Examples of ROM include a programmable read-only memory (PROM), an erasable programmable read-only memory (EPROM), an electrically erasable programmable read-only memory (EEPROM), or other like memory device. Even though FIG. 2A illustrates that game controller 202 includes a single memory 208, game controller 202 could include multiple memories 208 for storing program instructions and/or data.

Memory 208 can store one or more game programs 206 that provide program instructions and/or data for carrying out various implementations (e.g., game mechanics) described herein. Stated another way, game program 206 represents an executable program stored in any portion or component of memory 208. In one or more implementations, game program 206 is embodied in the form of source code that includes human-readable statements written in a programming language or machine code that contains numerical instructions recognizable by a suitable execution system, such as a processor 204 in a game controller or other system. Examples of executable programs include: (1) a compiled program that can be translated into machine code in a format that can be loaded into a random access portion of memory 208 and run by processor 204; (2) source code that may be expressed in proper format such as object code that is capable of being loaded into a random access portion of memory 208 and executed by processor 204; and (3) source code that may be interpreted by another executable program to generate instructions in a random access portion of memory 208 to be executed by processor 204.

Alternatively, game programs 206 can be set up to generate one or more game instances based on instructions and/or data that gaming device 200 exchanges with one or more remote gaming devices, such as a central determination gaming system server 106 (not shown in FIG. 2A but shown in FIG. 1). For purpose of this disclosure, the term "game instance" refers to a play or a round of a game that gaming device 200 presents (e.g., via a user interface (UI)) to a player. The game instance is communicated to gaming device 200 via the network 214 and then displayed on gaming device 200. For example, gaming device 200 may execute game program 206 as video streaming software that allows the game to be displayed on gaming device 200. When a game is stored on gaming device 200, it may be loaded from memory 208 (e.g., from a read only memory (ROM)) or from the central determination gaming system server 106 to memory 208.

Gaming devices, such as gaming device 200, are highly regulated to ensure fairness and, in many cases, gaming device 200 is operable to award monetary awards (e.g., typically dispensed in the form of a redeemable voucher). Therefore, to satisfy security and regulatory requirements in a gaming environment, hardware and software architectures are implemented in gaming devices 200 that differ significantly from those of general-purpose computers. Adapting general purpose computers to function as gaming devices 200 is not simple or straightforward because of: (1) the regulatory requirements for gaming devices 200, (2) the harsh environment in which gaming devices 200 operate, (3) security requirements, (4) fault tolerance requirements, and (5) the requirement for additional special purpose componentry enabling functionality of an electronic gaming device. These differences require substantial engineering effort with respect to game design implementation, game mechanics, hardware components, and software.

One regulatory requirement for games running on gaming device 200 generally involves complying with a certain level of randomness. Typically, gaming jurisdictions mandate that gaming devices 200 satisfy a minimum level of randomness without specifying how a gaming device 200 should achieve this level of randomness. To comply, FIG. 2A illustrates that gaming device 200 could include an RNG 212 that utilizes hardware and/or software to generate RNG outcomes that lack any pattern. The RNG operations are often specialized and non-generic in order to comply with regulatory and gaming requirements. For example, in a slot game, game program 206 can initiate multiple RNG calls to RNG 212 to generate RNG outcomes, where each RNG call and RNG outcome corresponds to an outcome for a reel. In another example, gaming device 200 can be a Class II gaming device where RNG 212 generates RNG outcomes for creating Bingo cards. In one or more implementations, RNG 212 could be one of a set of RNGs operating on gaming device 200. More generally, an output of the RNG 212 can be the basis on which game outcomes are determined by the game controller 202. Game developers could vary the degree of true randomness for each RNG (e.g., pseudorandom) and utilize specific RNGs depending on game requirements. The output of the RNG 212 can include a random number or pseudorandom number (either is generally referred to as a "random number").

In FIG. 2A, RNG 212 and hardware RNG 244 are shown in dashed lines to illustrate that RNG 212, hardware RNG 244, or both can be included in gaming device 200. In one implementation, instead of including RNG 212, gaming device 200 could include a hardware RNG 244 that generates RNG outcomes. Analogous to RNG 212, hardware RNG 244 performs specialized and non-generic operations in order to comply with regulatory and gaming requirements. For example, because of regulation requirements, hardware RNG 244 could be a random number generator that securely produces random numbers for cryptography use. The gaming device 200 then uses the secure random numbers to generate game outcomes for one or more game features. In another implementation, the gaming device 200 could include both hardware RNG 244 and RNG 212. RNG 212 may utilize the RNG outcomes from hardware RNG 244 as one of many sources of entropy for generating secure random numbers for the game features.

Another regulatory requirement for running games on gaming device 200 includes ensuring a certain level of RTP. Similar to the randomness requirement discussed above, numerous gaming jurisdictions also mandate that gaming device 200 provides a minimum level of RTP (e.g., RTP of at least 75%). A game can use one or more lookup tables (also called weighted tables) as part of a technical solution that satisfies regulatory requirements for randomness and RTP. In particular, a lookup table can integrate game features (e.g., trigger events for special modes or bonus games; newly introduced game elements such as extra reels, new symbols, or new cards; stop positions for dynamic game elements such as spinning reels, spinning wheels, or shifting reels; or card selections from a deck) with random numbers generated by one or more RNGs, so as to achieve a given level of volatility for a target level of RTP. (In general, volatility refers to the frequency or probability of an event such as a special mode, payout, etc. For example, for a target level of RTP, a higher-volatility game may have a lower payout most of the time with an occasional bonus having a very high payout, while a lower-volatility game has a steadier payout with more frequent bonuses of smaller amounts.) Configuring a lookup table can involve engineering decisions with respect to how RNG outcomes are mapped to game outcomes for a given game feature, while still satisfying regulatory requirements for RTP. Configuring a lookup table can also involve engineering decisions about whether different game features are combined in a given entry of the lookup table or split between different entries (for the respective game features), while still satisfying regulatory requirements for RTP and allowing for varying levels of game volatility.

FIG. 2A illustrates that gaming device 200 includes an RNG conversion engine 210 that translates the RNG outcome from RNG 212 to a game outcome presented to a player. To meet a designated RTP, a game developer can set up the RNG conversion engine 210 to utilize one or more lookup tables to translate the RNG outcome to a symbol element, stop position on a reel strip layout, and/or randomly chosen aspect of a game feature. As an example, the lookup tables can regulate a prize payout amount for each RNG outcome and how often the gaming device 200 pays out the prize payout amounts. The RNG conversion engine 210 could utilize one lookup table to map the RNG outcome to a game outcome displayed to a player and a second lookup table as a pay table for determining the prize payout amount for each game outcome. The mapping between the RNG outcome to the game outcome controls the frequency in hitting certain prize payout amounts.

FIG. 2A also depicts that gaming device 200 is connected over network 214 to player tracking system server 110. Player tracking system server 110 may be, for example, an OASIS® system manufactured by Aristocrat® Technologies, Inc. Player tracking system server 110 is used to track play (e.g. amount wagered, games played, time of play and/or other quantitative or qualitative measures) for individual players so that an operator may reward players in a loyalty program. The player may use the player tracking interface 232 to access his/her account information, activate free play, and/or request various information. Player tracking or loyalty programs seek to reward players for their play and help build brand loyalty to the gaming establishment. The rewards typically correspond to the player's level of patronage (e.g., to the player's playing frequency and/or total amount of game plays at a given casino). Player tracking rewards may be complimentary and/or discounted meals, lodging, entertainment and/or additional play. Player tracking information may be combined with other information that is now readily obtainable by a casino management system.

When a player wishes to play the gaming device 200, he/she can insert cash or a ticket voucher through a coin acceptor (not shown) or bill validator 234 to establish a credit balance on the gaming device. The credit balance is used by the player to place wagers on instances of the game and to receive credit awards based on the outcome of winning instances. The credit balance is decreased by the amount of each wager and increased upon a win. The player can add additional credits to the balance at any time. The player may also optionally insert a loyalty club card into the card reader 230. During the game, the player views with one or more UIs, the game outcome on one or more of the primary game display 240 and secondary game display 242. Other game and prize information may also be displayed.

For each game instance, a player may make selections, which may affect play of the game. For example, the player may vary the total amount wagered by selecting the amount bet per line and the number of lines played. In many games, the player is asked to initiate or select options during course of game play (such as spinning a wheel to begin a bonus round or select various items during a feature game). The player may make these selections using the player-input buttons 236, the primary game display 240 which may be a touch screen, or using some other device which enables a player to input information into the gaming device 200.

During certain game events, the gaming device 200 may display visual and auditory effects that can be perceived by the player. These effects add to the excitement of a game, which makes a player more likely to enjoy the playing experience. Auditory effects include various sounds that are projected by the speakers 220. Visual effects include flashing lights, strobing lights or other patterns displayed from lights on the gaming device 200 or from lights behind the information panel 152 (FIG. 1).

When the player is done, he/she cashes out the credit balance (typically by pressing a cash out button to receive a ticket from the ticket printer 222). The ticket may be "cashed-in" for money or inserted into another machine to establish a credit balance for play.

Additionally, or alternatively, gaming devices 104A-104X and 200 can include or be coupled to one or more wireless transmitters, receivers, and/or transceivers (not shown in FIGS. 1 and 2A) that communicate (e.g., Bluetooth® or other near-field communication technology) with one or more mobile devices to perform a variety of wireless operations in a casino environment. Examples of wireless operations in a casino environment include detecting the presence of mobile devices, performing credit, points, comps, or other marketing or hard currency transfers, establishing wagering sessions, and/or providing a personalized casino-based experience using a mobile application. In one implementation, to perform these wireless operations, a wireless transmitter or transceiver initiates a secure wireless connection between a gaming device 104A-104X and 200 and a mobile device. After establishing a secure wireless connection between the gaming device 104A-104X and 200 and the mobile device, the wireless transmitter or transceiver does not send and/or receive application data to and/or from the mobile device. Rather, the mobile device communicates with gaming devices 104A-104X and 200 using another wireless connection (e.g., WiFi® or cellular network). In another implementation, a wireless transceiver establishes a secure connection to directly communicate with the mobile device. The mobile device and gaming device 104A-104X and 200 sends and receives data utilizing the wireless transceiver instead of utilizing an external network. For example, the mobile device would perform digital wallet transactions by directly communicating with the wireless transceiver. In one or more implementations, a wireless transmitter could broadcast data received by one or more mobile devices without establishing a pairing connection with the mobile devices.

Although FIGS. 1 and 2A illustrate specific implementations of a gaming device (e.g., gaming devices 104A-104X and 200), the disclosure is not limited to those implementations shown in FIGS. 1 and 2. For example, not all gaming devices suitable for implementing implementations of the present disclosure necessarily include top wheels, top boxes, information panels, cashless ticket systems, and/or player tracking systems. Further, some suitable gaming devices have only a single game display that includes only a mechanical set of reels and/or a video display, while others are designed for bar counters or tabletops and have displays that face upwards Gaming devices 104A-104X and 200 may also include other processors that are not separately shown. Using FIG. 2A as an example, gaming device 200 could include display controllers (not shown in FIG. 2A) configured to receive video input signals or instructions to display images on game displays 240 and 242. Alternatively, such display controllers may be integrated into the game controller 202. The use and discussion of FIGS. 1 and 2 are examples to facilitate ease of description and explanation.

Figure 2B:
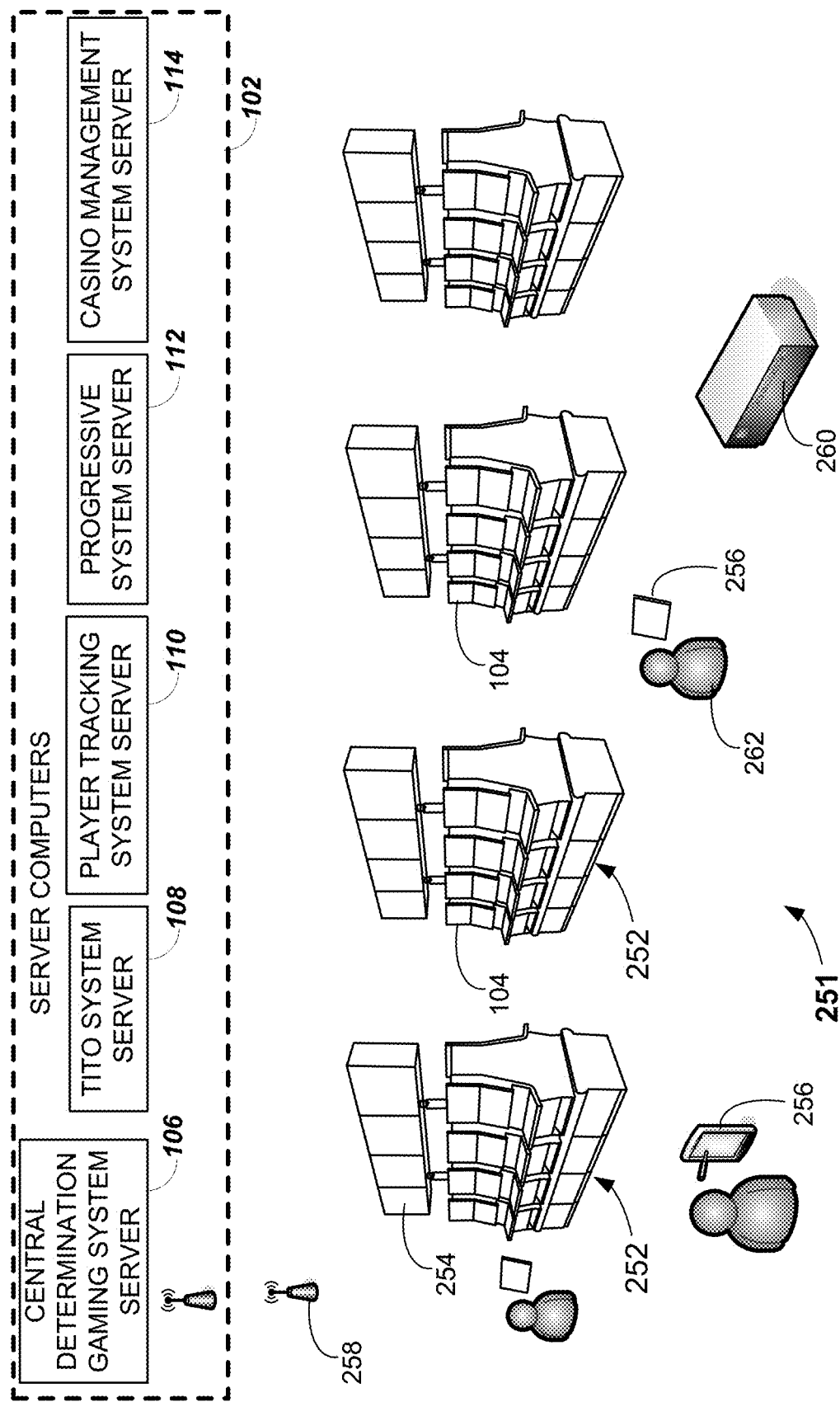
FIG. 2B depicts a casino gaming environment according to one example.

FIG. 2B depicts a casino gaming environment according to one example. In this example, the casino 251 includes banks 252 of electronic gaming devices 104. In this example, each bank 252 of electronic gaming devices 104 includes a corresponding gaming signage system 254 (also shown in FIG. 2A). According to this implementation, the casino 251 also includes mobile gaming devices 256, which are also configured to present wagering games in this example. The mobile gaming devices 256 may, for example, include tablet devices, cellular phones, smart phones and/or other handheld devices. In this example, the mobile gaming devices 256 are configured for communication with one or more other devices in the casino 251, including but not limited to one or more of the server computers 102, via wireless access points 258.

According to some examples, the mobile gaming devices 256 may be configured for stand-alone determination of game outcomes. However, in some alternative implementations the mobile gaming devices 256 may be configured to receive game outcomes from another device, such as the central determination gaming system server 106, one of the electronic gaming devices 104, etc.

Some mobile gaming devices 256 may be configured to accept monetary credits from a credit or debit card, via a wireless interface (e.g., via a wireless payment app), via tickets, via a patron casino account, etc. However, some mobile gaming devices 256 may not be configured to accept monetary credits via a credit or debit card. Some mobile gaming devices 256 may include a ticket reader and/or a ticket printer whereas some mobile gaming devices 256 may not, depending on the particular implementation.

In some implementations, the casino 251 may include one or more kiosks 260 that are configured to facilitate monetary transactions involving the mobile gaming devices 256, which may include cash out and/or cash in transactions. The kiosks 260 may be configured for wired and/or wireless communication with the mobile gaming devices 256. The kiosks 260 may be configured to accept monetary credits from casino patrons 262 and/or to dispense monetary credits to casino patrons 262 via cash, a credit or debit card, via a wireless interface (e.g., via a wireless payment app), via tickets, etc. According to some examples, the kiosks 260 may be configured to accept monetary credits from a casino patron and to provide a corresponding amount of monetary credits to a mobile gaming device 256 for wagering purposes, e.g., via a wireless link such as a near-field communications link. In some such examples, when a casino patron 262 is ready to cash out, the casino patron 262 may select a cash out option provided by a mobile gaming device 256, which may include a real button or a virtual button (e.g., a button provided via a graphical user interface) in some instances. In some such examples, the mobile gaming device 256 may send a "cash out" signal to a kiosk 260 via a wireless link in response to receiving a "cash out" indication from a casino patron. The kiosk 260 may provide monetary credits to the casino patron 262 corresponding to the "cash out" signal, which may be in the form of cash, a credit ticket, a credit transmitted to a financial account corresponding to the casino patron, etc.

In some implementations, a cash-in process and/or a cash-out process may be facilitated by the TITO system server 108. For example, the TITO system server 108 may control, or at least authorize, ticket-in and ticket-out transactions that involve a mobile gaming device 256 and/or a kiosk 260.

Some mobile gaming devices 256 may be configured for receiving and/or transmitting player loyalty information. For example, some mobile gaming devices 256 may be configured for wireless communication with the player tracking system server 110. Some mobile gaming devices 256 may be configured for receiving and/or transmitting player loyalty information via wireless communication with a patron's player loyalty card, a patron's smartphone, etc.

According to some implementations, a mobile gaming device 256 may be configured to provide safeguards that prevent the mobile gaming device 256 from being used by an unauthorized person. For example, some mobile gaming devices 256 may include one or more biometric sensors and may be configured to receive input via the biometric sensor(s) to verify the identity of an authorized patron. Some mobile gaming devices 256 may be configured to function only within a predetermined or configurable area, such as a casino gaming area.

Figure 3:
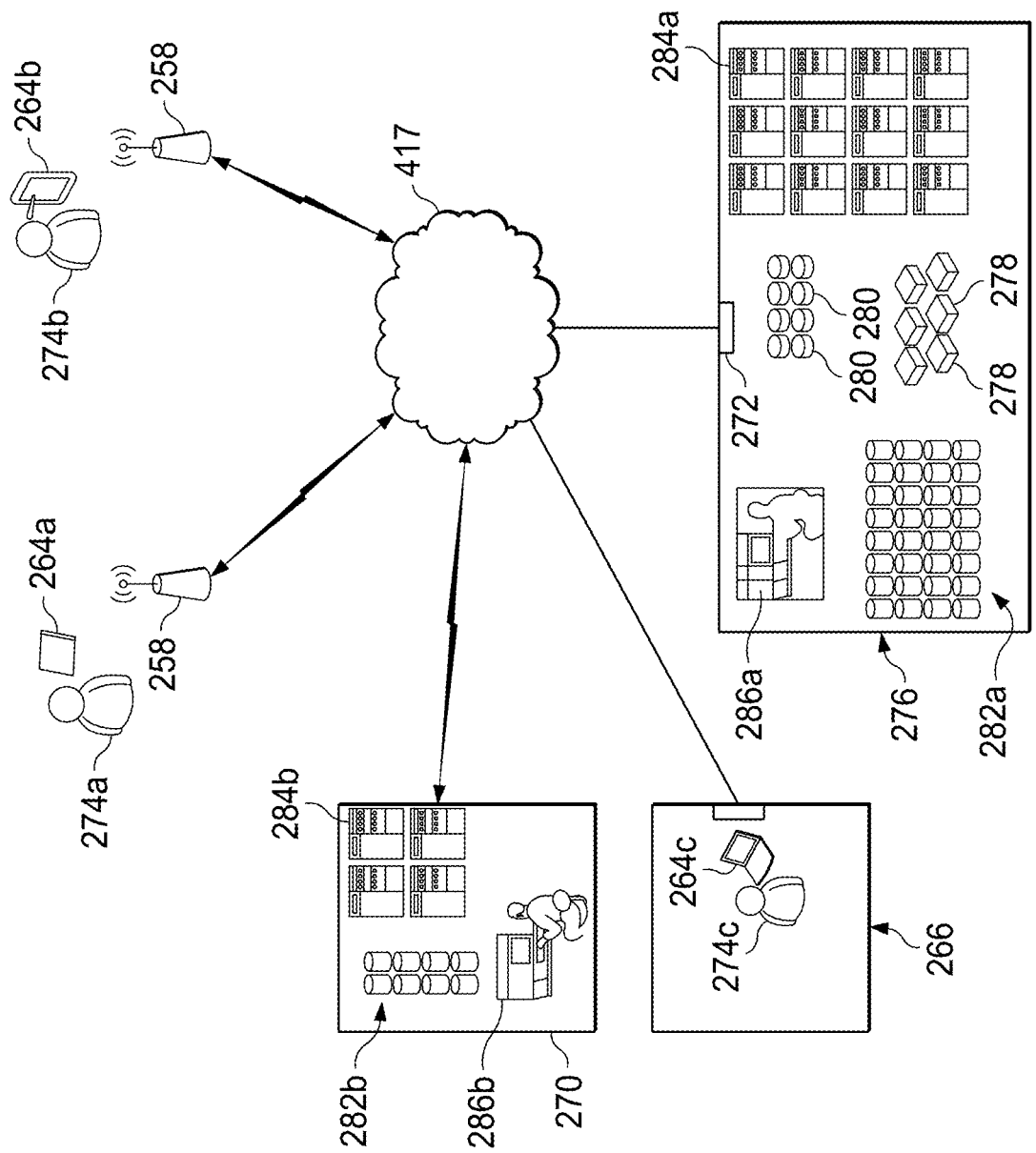
FIG. 3 is a diagram that shows examples of components of a system for providing online gaming according to some aspects of the present disclosure.

FIG. 3 is a diagram that shows examples of components of a system for providing online gaming according to some aspects of the present disclosure. As with other figures presented in this disclosure, the numbers, types and arrangements of gaming devices shown in FIG. 3 are merely shown by way of example. In this example, various gaming devices, including but not limited to end user devices (EUDs) 264a, 264b and 264c are capable of communication via one or more networks 417. The networks 417 may, for example, include one or more cellular telephone networks, the Internet, etc. In this example, the EUDs 264a and 264b are mobile devices: according to this example the EUD 264a is a tablet device and the EUD 264b is a smart phone. In this implementation, the EUD 264c is a laptop computer that is located within a residence 266 at the time depicted in FIG. 3. Accordingly, in this example the hardware of EUDs is not specifically configured for online gaming, although each EUD is configured with software for online gaming. For example, each EUD may be configured with a web browser. Other implementations may include other types of EUD, some of which may be specifically configured for online gaming.

In this example, a gaming data center 276 includes various devices that are configured to provide online wagering games via the networks 417. The gaming data center 276 is capable of communication with the networks 417 via the gateway 272. In this example, switches 278 and routers 280 are configured to provide network connectivity for devices of the gaming data center 276, including storage devices 282a, servers 284a and one or more workstations 570a. The servers 284a may, for example, be configured to provide access to a library of games for online game play. In some examples, code for executing at least some of the games may initially be stored on one or more of the storage devices 282a. The code may be subsequently loaded onto a server 284a after selection by a player via an EUD and communication of that selection from the EUD via the networks 417. The server 284a onto which code for the selected game has been loaded may provide the game according to selections made by a player and indicated via the player's EUD. In other examples, code for executing at least some of the games may initially be stored on one or more of the servers 284a. Although only one gaming data center 276 is shown in FIG. 3, some implementations may include multiple gaming data centers 276.

In this example, a financial institution data center 270 is also configured for communication via the networks 417. Here, the financial institution data center 270 includes servers 284b, storage devices 282b, and one or more workstations 286b. According to this example, the financial institution data center 270 is configured to maintain financial accounts, such as checking accounts, savings accounts, loan accounts, etc. In some implementations one or more of the authorized users 274a-274c may maintain at least one financial account with the financial institution that is serviced via the financial institution data center 270.

According to some implementations, the gaming data center 276 may be configured to provide online wagering games in which money may be won or lost. According to some such implementations, one or more of the servers 284a may be configured to monitor player credit balances, which may be expressed in game credits, in currency units, or in any other appropriate manner. In some implementations, the server(s) 284a may be configured to obtain financial credits from and/or provide financial credits to one or more financial institutions, according to a player's "cash in" selections, wagering game results and a player's "cash out" instructions. According to some such implementations, the server(s) 284a may be configured to electronically credit or debit the account of a player that is maintained by a financial institution, e.g., an account that is maintained via the financial institution data center 270. The server(s) 284a may, in some examples, be configured to maintain an audit record of such transactions.

In some alternative implementations, the gaming data center 276 may be configured to provide online wagering games for which credits may not be exchanged for cash or the equivalent. In some such examples, players may purchase game credits for online game play, but may not "cash out" for monetary credit after a gaming session. Moreover, although the financial institution data center 270 and the gaming data center 276 include their own servers and storage devices in this example, in some examples the financial institution data center 270 and/or the gaming data center 276 may use offsite "cloud-based" servers and/or storage devices. In some alternative examples, the financial institution data center 270 and/or the gaming data center 276 may rely entirely on cloud-based servers.

One or more types of devices in the gaming data center 276 (or elsewhere) may be capable of executing middleware, e.g., for data management and/or device communication. Authentication information, player tracking information, etc., including but not limited to information obtained by EUDs 264 and/or other information regarding authorized users of EUDs 264 (including but not limited to the authorized users 274a-274c), may be stored on storage devices 282 and/or servers 284. Other game-related information and/or software, such as information and/or software relating to leaderboards, players currently playing a game, game themes, game-related promotions, game competitions, etc., also may be stored on storage devices 282 and/or servers 284. In some implementations, some such game-related software may be available as "apps" and may be downloadable (e.g., from the gaming data center 276) by authorized users.

In some examples, authorized users and/or entities (such as representatives of gaming regulatory authorities) may obtain gaming-related information via the gaming data center 276. One or more other devices (such EUDs 264 or devices of the gaming data center 276) may act as intermediaries for such data feeds. Such devices may, for example, be capable of applying data filtering algorithms, executing data summary and/or analysis software, etc. In some implementations, data filtering, summary and/or analysis software may be available as "apps" and downloadable by authorized users.

II. Introduction.

The effectiveness of UV light as a germicide depends on many factors, including duration of exposure, distance from the UV light source, intensity of the UV light, wavelength of the UV light, and the type of pathogen. For example, the average time to disinfect typical bacterial pathogens from surfaces is between 30 and 280 seconds, from a distance of at most 5 feet from a UV-C light source. As another example, the average time to disinfect some viral pathogens from surfaces is between 300 and 600 seconds, from a distance of at most 3 feet from a UV-C light source. The effectiveness of UV disinfection can increase with pre-cleaning of surfaces.

UV-C refers to a wavelength range of UV light that has been found to be especially effective for germicidal applications. Exposure to UV-C light causes photochemical reactions in DNA and RNA of microbes, resulting in inactivation of the microbes and failure to reproduce. UV-A light and UV-B light, in comparison, cause oxidation of proteins and lipids of microbes, resulting in cell death, and blue (visible) light inhibits bacterial growth by prompting generation of reactive oxygen species, which are toxic to bacterial cells.

III. Example UV Light Sources.

This section describes some of the types of UV light sources that can be used in innovations described herein.

Example implementations described herein use UV light sources that primarily emit UV-C light, but can also emit UV-B light, and even UV-A light and blue light. Alternatively, the UV light sources can primarily emit UV-A light and/or UV-B light. Thus, in the innovations described herein, a UV light source, when activated, can predominately emit UV-C light (within a range of approximately 100 nanometers to approximately 280 nanometers), UV-B light (within a range of approximately 280 nanometers to approximately 315 nanometers), or UV-A light (within a range of approximately 315 nanometers to approximately 400 nanometers). In particular, in some example implementations, a UV light source, when activated, predominately emits UV-C light, within a range of approximately 240 nanometers to approximately 280 nanometers.

UV-C light is typically more effective than other types of UV light for UV disinfection. While UV-C is "safer" than UV-B light for humans in some respects, exposure to UV-C light still poses risks to humans. For example, excessive exposure to UV-C light can cause skin damage or retinal damage. To address this concern, innovations described herein can control activation of UV light sources to reduce risks to humans nearby and/or orient UV light sources so as to avoid, or at least reduce, direct emission of UV light to users' eyes, skin, etc.

In the innovations described herein, a UV light source can be implemented with various types of light sources. In some example implementations, a UV light source is a UV light-emitting diode ("LED"). Alternatively, a UV light source can be a UV lamp (e.g., a Xenon flash lamp or mercury vapor lamp). Alternatively, another type of UV light source can be used in the innovations described herein.

UV light sources can be arranged in one or more light strips, with each of the light strips including multiple UV light sources. For example, an array of UV LEDs can be arranged in a UV LED strip (also called a UV light strip). A UV light strip can be embedded in a recessed cavity, in an electronic gaming device, cover assembly, chip tray, or other equipment, which is adapted to fit the UV light strip. Alternatively, a UV light source can be installed in a socket, which is in turn embedded in a recessed cavity in an electronic gaming device, cover assembly, chip tray, or other equipment. Or, a UV light strip or other UV light source can be affixed to an electronic gaming device, cover assembly, chip tray, or other equipment in some other way, e.g., fastening it to a surface.

A UV light source can be oriented in various ways relative to a surface to be disinfected. A "front-firing" (or "top-firing" or "rear-firing"; collectively referred to as front-firing herein) UV light source is oriented so that it faces the surface to be disinfected. The front-firing UV light source directly emits UV light towards the surface to be disinfected, with at least some of the UV light being emitted in rays perpendicular or nearly perpendicular to much of the surface. A front-firing UV light source is typically placed at some distance from the surface to be disinfected, in order to have a wider scope of coverage across the surface, while still being close enough to the surface to be effective for UV disinfection. In contrast, a "side-firing" UV light source is oriented so that it faces across the surface to be disinfected. The side-firing UV light source emits UV light across the surface, with at least some of the UV light being emitted in rays parallel or nearly parallel to some of the surface. (Even for a side-firing UV light source, however, some of the UV light may approach the surface along perpendicular or nearly perpendicular rays, depending on distance to the intersected spot on the surface.) A side-firing UV light source is typically placed along an edge of the surface to be disinfected. Regardless of placement and orientation, UV light can be reflected at various angles towards a surface to be disinfected.

A reflective shield such as a visor, cone, etc. can be placed around a UV light source to guide UV light to targeted surfaces. The reflective shield can follow the contour of the UV light source or a group of UV light sources (e.g., in a light strip or array), and have an opening towards the surface to be disinfected.

Further, a reflective shield such as a visor can be positioned, between a UV light source and user position, to block at least some of the UV light emitted by UV light source, when activated, and potentially reflect the UV light back to the surface to be disinfected. The reflective shield can be static—staying in place whether or not UV disinfection is in process. Or, the reflective shield can be dynamic—moving into place or otherwise become active when UV disinfection is in process. For example, the reflective shield can slide into place over a button deck or touchscreen display when UV disinfection is in process, and then slide back to a recessed area when UV disinfection is completed. Or, as another example, the reflective shield can switch between modes (e.g., with different characteristics in terms of transmissivity of UV light) depending on whether UV disinfection is in process.

IV. Examples of Controlling Activation of UV Light Sources.

This section describes example approaches to controlling activation of one or more UV light sources for UV disinfection. UV light source(s) can be activated in response to different activation conditions. In some implementations, UV light source(s) can change characteristics of UV disinfection (e.g., duration of exposure, intensity of UV light).

In general, UV light source(s) are configured to be activated in response to an activation condition or multiple activation conditions in combination. Different activation conditions can be used, depending on implementation. A given implementation can recognize different activation conditions, which may trigger different UV disinfection modes. Different activation conditions can be used in combination, depending on implementation.

For example, an activation condition can be inactivity of a user. The inactivity of the user can be indicated by expiration of an activity timer (elapsed time after a user ends a gaming session/"cashes out") or indicated in some other way (e.g., lack of response to a prompt to the user from the electronic gaming device). According to this activation condition, if user inactivity is detected, the UV light source(s) may be activated (so long as other applicable activation conditions are satisfied).

As another example, an activation condition can be recognition of empty space in a threshold region in the vicinity of the electronic gaming device or other equipment. The empty space can be indicated by feedback from a camera, by a heat sensor, or in some other way. According to this activation condition, if empty space is detected, the UV light source(s) may be activated (so long as other applicable activation conditions are satisfied).

Or, as another example, an activation condition can be actuation of a button on the electronic gaming device or other equipment, expressly requesting the start of UV disinfection. The button can be a physical button or virtual button on a button deck or touchscreen display. According to this activation condition, if the button is actuated, the UV light source(s) may be activated (so long as other applicable activation conditions are satisfied).

Or, as another example, an activation condition can be the current time reaching a defined start time for a UV disinfection cycle. The defined start time can be an administrator-settable time at which an electronic gaming device is offline or out of service, or another administrator-settable time. According to this activation condition, if the defined start time is reached, the UV light source(s) may be activated (so long as other applicable activation conditions are satisfied).

Or, as another example, an activation condition can be receipt of a UV-disinfection-start prompt from a system server for a UV disinfection cycle. The UV-disinfection-start prompt can be issued by the system server as part of a site-wide UV disinfection process. According to this activation condition, if a UV-disinfection-start prompt is received, the UV light source(s) may be activated (so long as other applicable activation conditions are satisfied).

A system server can issue UV-disinfection-start prompts to all electronic gaming devices at a site, to a specific bank of electronic gaming devices, or to selected (less than all) electronic gaming devices at a site or in a bank of electronic gaming devices. For example, a system server can issue UV-disinfection-start prompts to electronic gaming devices that are idle (not currently in use), or a system server can issue UV-disinfection-start prompts to electronic gaming devices that have been forced into an idle state/disabled by the system server. In some example implementations, when an electronic gaming device is in use, a system server can attempt to impose "social distancing" between users by forcing adjacent electronic gaming devices (that is, electronic gaming devices next to or nearby the in-use electronic gaming device) into a forced-idle/disabled state, which locks out users. The system server can then issue UV-disinfection-start prompts to the forced-idle/disabled electronic gaming devices, triggering activation of UV light source(s) at the respective forced-idle/disabled electronic gaming devices (so long as other applicable activation conditions are satisfied). Or, the prompts sent to put electronic gaming devices into a forced-idle/disabled state can automatically trigger activation of UV light source(s) at the respective forced-idle/disabled electronic gaming devices (so long as other applicable activation conditions are satisfied). (In this case, the prompt sent by the system server to put an electronic gaming device into a forced-idle/disabled state is also a UV-disinfection-start prompt.) In this way, the system server can take advantage of the forced lock-out of the adjacent electronic gaming devices to perform UV disinfection on the adjacent electronic gaming devices. Thus, for example, a system server can force electronic gaming devices in a pattern (such as every other device) into a lock-out state and trigger UV disinfection cycles on the locked-out electronic gaming devices.

Or, as another example, an activation condition can be the closing of a lid or cover. The lid or cover can enclose a button deck, a chip tray, or other equipment, at which point UV disinfection may proceed within the enclosure. According to this activation condition, if the lid or cover is closed, the UV light source(s) may be activated (so long as other applicable activation conditions are satisfied).

Or, as another example, an activation condition can be detection of a warning condition for a user. The warning condition can be a high temperature or other symptom of illness. According to this activation condition, if the warning condition is detected, the UV light source(s) may be activated (so long as other applicable activation conditions are satisfied).

Or, as another example, an activation condition can be detection of pathogens. A hyperspectral camera or other sensor can detect the pathogens, triggering UV disinfection. According to this activation condition, if pathogens are detected, the UV light source(s) may be activated (so long as other applicable activation conditions are satisfied).

In addition to controlling whether or not UV light source(s) are activated, activation conditions can regulate how UV disinfection is performed. UV disinfection processes can vary in terms of duration (e.g., 30 seconds, 10 minutes, 30 minutes), intensity of UV light (e.g., low intensity versus high intensity), wavelength of UV light (e.g., UV-C versus UV-B), scope of coverage (e.g., wide versus narrow; complete versus targeted), and/or other factors. Alternatively, the UV light source(s) can be activated at all times, but potentially vary according such factors.

Depending on implementation, the UV light source(s) can be stationary. For example, the UV light source(s) can be fixed in position and orientation. Alternatively, the UV light source(s) can be active, being configured to move along at least one dimension when activated. For example, a UV light source can be controllably focused on part of an electronic gaming device or other gaming equipment, according to a defined pattern.

Depending on implementation, the UV light source(s) can emit UV light at an intensity that is at least roughly constant. Or, the UV light source(s) can emit UV light at an intensity that is variable. For example, the intensity of the UV light can vary depending on UV disinfection mode and/or depending on activation condition. Or, as another example, the intensity of the UV light can vary depending on orientation away from a user position. In this way, the intensity of the UV light can be highest at an orientation directly away from the user position, and the intensity of the UV light can decrease at orientations closer to the user position. Or, as another example, the intensity of the UV light can vary depending on orientation towards one or more touch points on a button deck, touchscreen display, etc. In this way, the intensity of the UV light can be highest at an orientation directly towards the touch point(s), and the intensity of the UV light can decrease at orientations further from the touch point(s).

Depending on implementation, the UV light source(s) can emit UV light at a wavelength that is at least roughly constant. Or, the UV light source(s) can emit UV light at a wavelength that is variable. For example, the wavelength of the UV light can vary depending on UV disinfection mode and/or a target pathogen.

V. Example Electronic Gaming Devices with Side-Firing UV Light Sources at Edge(s) of Button Deck.

This section describes example electronic gaming devices that include one or more UV light sources at the edges of button decks of the electronic gaming devices. Typically, the button deck of an electronic gaming device includes many touch points such as physical buttons, touchscreen buttons, and surfaces on which a user rests his or her hands. In some example implementations, side-firing UV light sources at one or more edges of a button deck can disinfect the touch points and other surfaces of the button deck.

Figure 4:
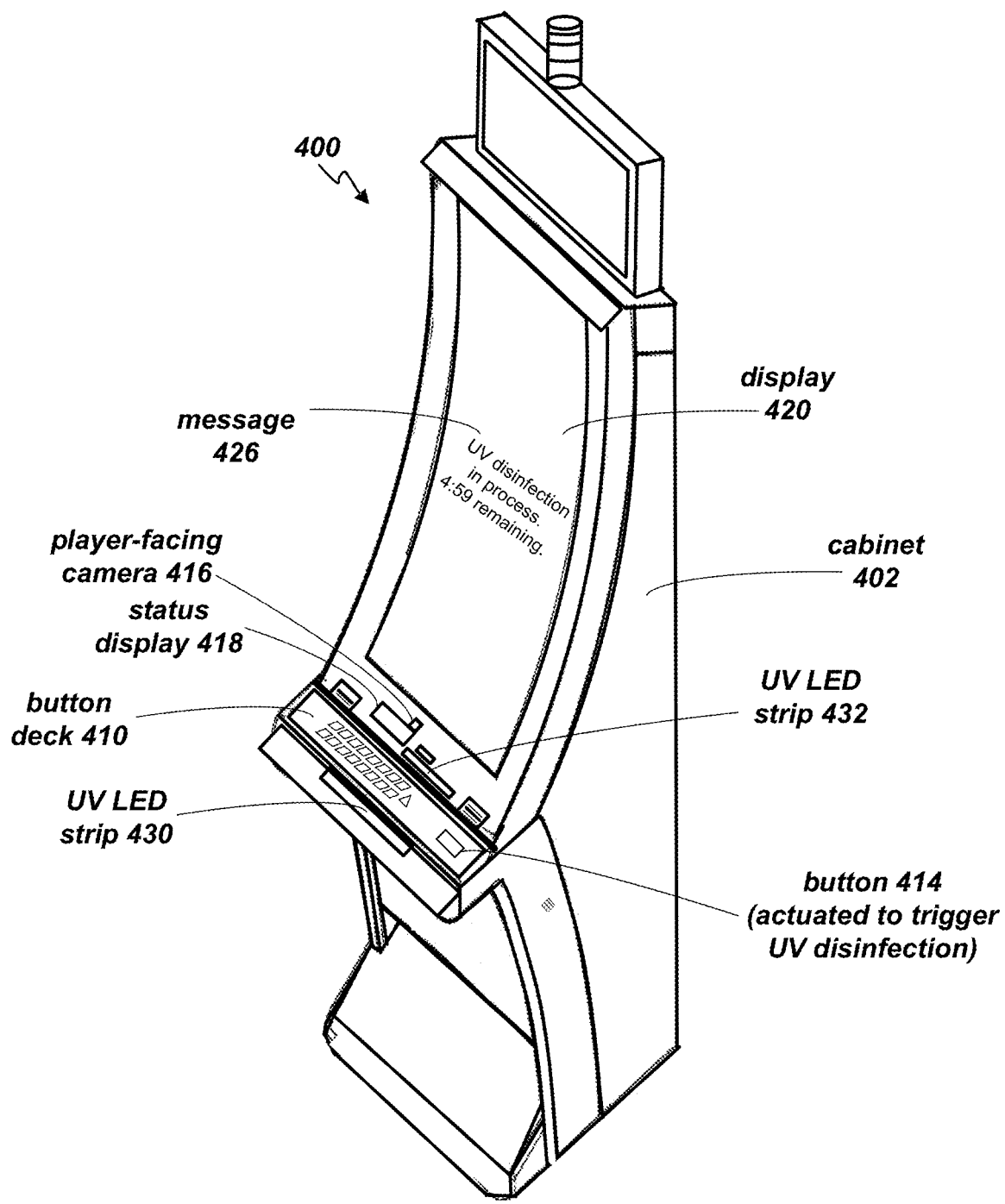
FIG. 4 illustrates an example electronic gaming device that includes UV light sources at edges of a button deck, as well as other hardware and software features to manage UV disinfection.

FIG. 4 shows an example electronic gaming device 400 that includes UV light sources at edges of a button deck, as well as other hardware and software features to manage UV disinfection. The electronic gaming device 400 includes a cabinet 402, a button deck 410, and a display 420, which may be a touchscreen display or non-touchscreen display. The electronic gaming device 400 also includes a processor, memory, and other components described with reference to FIG. 1. Alternatively, the electronic gaming device 400 can have any of the other form factors described in section I for an electronic gaming device. Depending on implementation, the electronic gaming device 400 can also include components described in section X for UV disinfection.

The electronic gaming device 400 includes one or more UV light sources, which are arranged along at least one edge of the button deck 410 so as to, when activated, emit UV light across at least part of the button deck 410. In FIG. 4, the electronic gaming device 400 includes two UV LED strips 430, 432, which are arranged along opposite edges of the button deck 410.

UV light source(s) can be arranged at an edge of a button deck that is closest to a user position, so as to, when activated, emit UV light away from the user position. In FIG. 4, the first UV LED strip 430 is arranged along the edge of the button deck 410 closest to the user position. When activated, the UV LED strip 430 generally emits UV light away from the user position, which can reduce exposure to UV light.

UV light source(s) can also be arranged at an edge of a button deck that is farthest from a user position, so as to, when activated, emit UV light away towards the user position. In FIG. 4, the second UV LED strip 432 is arranged along the edge of the button deck 410 farthest from the user position. When activated, the UV LED strip 432 generally emits UV light away towards the user position. To address safety concerns, the UV LED strip 432 (and also the UV LED strip 430) can be controlled to emit UV light at a lower intensity or only when the user is not present.

More generally, UV light source(s) can be arranged along one edge of a button deck, two opposite edges of the button deck, all but one edge of the button deck, or all edges of the button deck. The button deck can include one or more physical buttons (e.g., each including a button housing, a spring, and a switch). The button deck can also, or alternatively, include one or more virtual buttons (e.g., touchscreen buttons on a touchscreen display). The UV light source(s) can be implemented and controlled using any of the approaches described in sections III and IV.

An electronic gaming device can include a reflective shield such as a visor, cone, etc. around the respective UV light source(s) to guide UV light to targeted surfaces. An electronic gaming device can include a reflective shield such as a visor or armrest positioned to block at least some of the UV light emitted by UV light source(s), when activated.

UV light source(s) can be embedded in the electronic gaming device 400 or attached to the electronic gaming device 400 using any of the approaches described above. In FIG. 4, the UV LED strips 430, 432 are embedded in the cabinet 402 along edges of the button deck 410.

The button deck 410 of the electronic gaming device 400 includes a button 414, which can be actuated to trigger UV disinfection "on demand" or to request manual UV disinfection of the electronic gaming device 400 (e.g., by sending a notification from the electronic gaming device 400 to floor staff or housekeeping staff to manually clean the button deck 410). The response associated with button 414 depends on implementation. Although FIG. 4 shows the button 414 on the button deck 410, the button 414 can alternatively be placed on a player tracking system interface or other location on the electronic gaming device 400. Although FIG. 4 shows a single button 414, the electronic gaming device 400 can include multiple buttons to request or control UV disinfection (e.g., a first button trigger UV disinfection on demand, and a second button to request manual UV disinfection of the electronic gaming device 400). Or, a single button can be associated with multiple responses, e.g., triggering a short, automatic UV disinfection cycle using the UV LED strips 430, 432, and sending a notification from the electronic gaming device 400 to floor staff or housekeeping staff to manually clean the button deck 410 when the electronic gaming device is not in use). A button or light can also indicate UV disinfection status of an electronic gaming device (e.g., by flashing or staying lit).

An electronic gaming device can include one or more displays configured to show status information for UV disinfection. The status information can be a notification that UV disinfection has completed as part of an attract mode (e.g., "this button deck is clean—are you sure about other machines"). Or, the status information can be a notification that UV disinfection is ongoing (e.g., a timer counting down until a UV disinfection cycle is finished). In FIG. 4, the electronic gaming device 400 includes two displays configured to shows status information. A status display 418, which is on or near a player tracking system interface, indicates status information for UV disinfection. The status display 418 can be a touchscreen display or non-touchscreen display. A player-facing camera 416, as described in section X, can provide feedback to the electronic gaming device 400. On the display 420, a message 426 also indicates status information for UV disinfection, which can the same or different than the status information on the status display 418.

Figure 5:
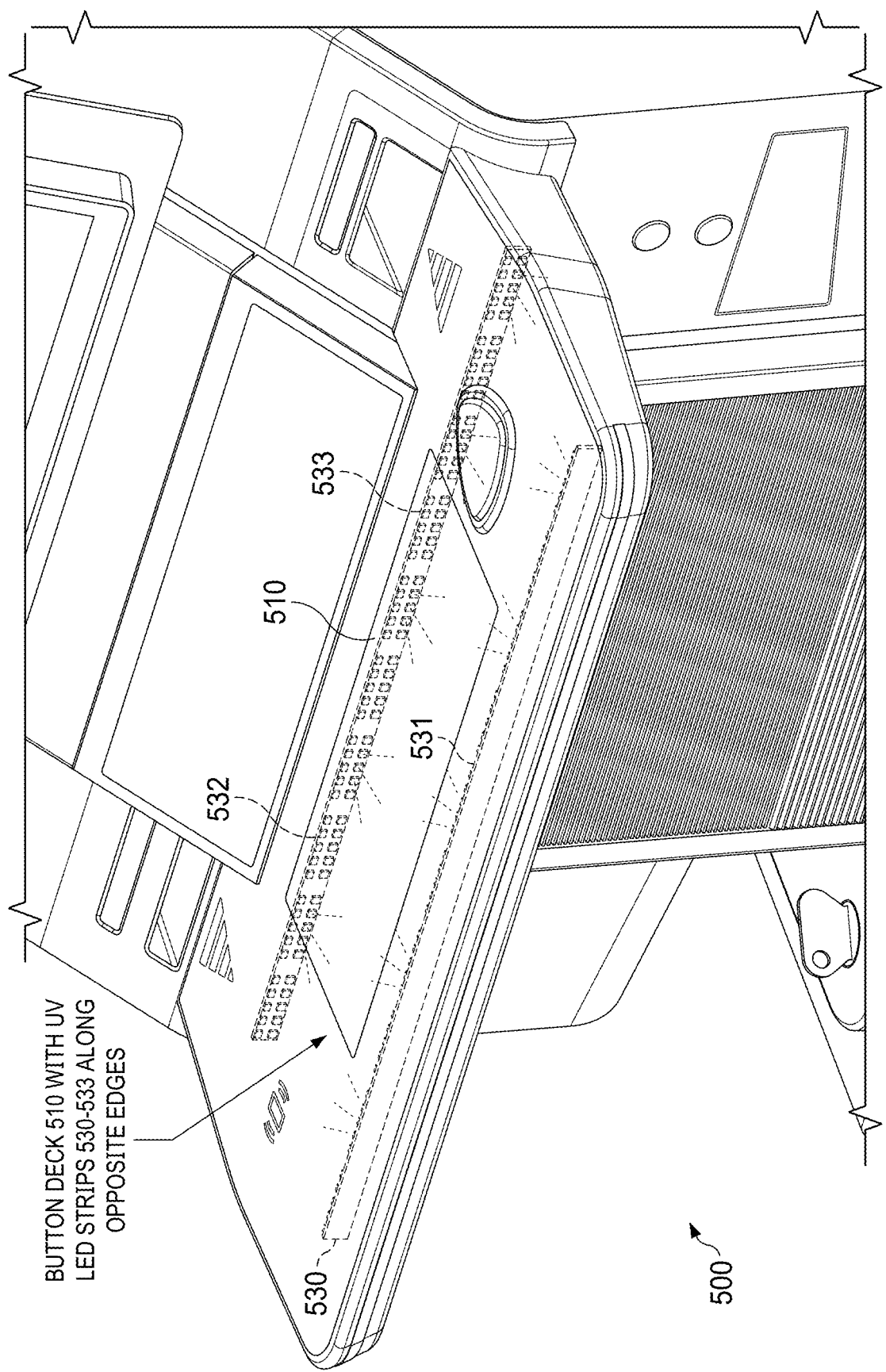
FIG. 5 illustrates an example button deck of an electronic gaming device, with UV light sources along opposite edges of the button deck.

FIG. 5 shows an example button deck 510 of an electronic gaming device 500, with UV light sources along opposite edges of the button deck 510. The button deck 510 includes UV LED strips 530-533 along opposite edges of the button deck 510. Two UV LED strips 530, 531 are embedded in the cabinet of the electronic gaming device 500 along the edge of the button deck 510 that is closest to the user position. The two UV LED strips 530, 531 are side-firing LED strips configured to emit UV light away from the user position. Two other UV LED strips 532, 533 are embedded in the cabinet of the electronic gaming device 500 along the edge of the button deck 510 that is farthest from the user position. The two UV LED strips 532, 533 are side-firing LED strips configured to emit UV light away towards the user position.

The electronic gaming device 400 can include one or more additional UV light sources arranged along at least one edge of the display 420 so as to, when activated, emit UV light across at least part of the electronic gaming device 400. For example, in addition to UV light source(s) arranged along edge(s) of the button deck 410, the electronic gaming device 400 can include additional UV light source(s) arranged along an opposite edge of the display 420. Such examples are described with reference to FIGS. 10A-10C.

VI. Example Electronic Gaming Devices with Side-Firing UV Light Sources at Edge(s) of Display.

This section describes example electronic gaming devices that include one or more UV light sources at the edges of displays of the electronic gaming devices. The display of an electronic gaming device can include touch points such as touchscreen buttons, surfaces on which a user places his or her hands, and surfaces on which a user breathes or coughs. In some example implementations, side-firing UV light sources at one or more edges of a display can disinfect the touch points and other surfaces of the display.

Figure 6:
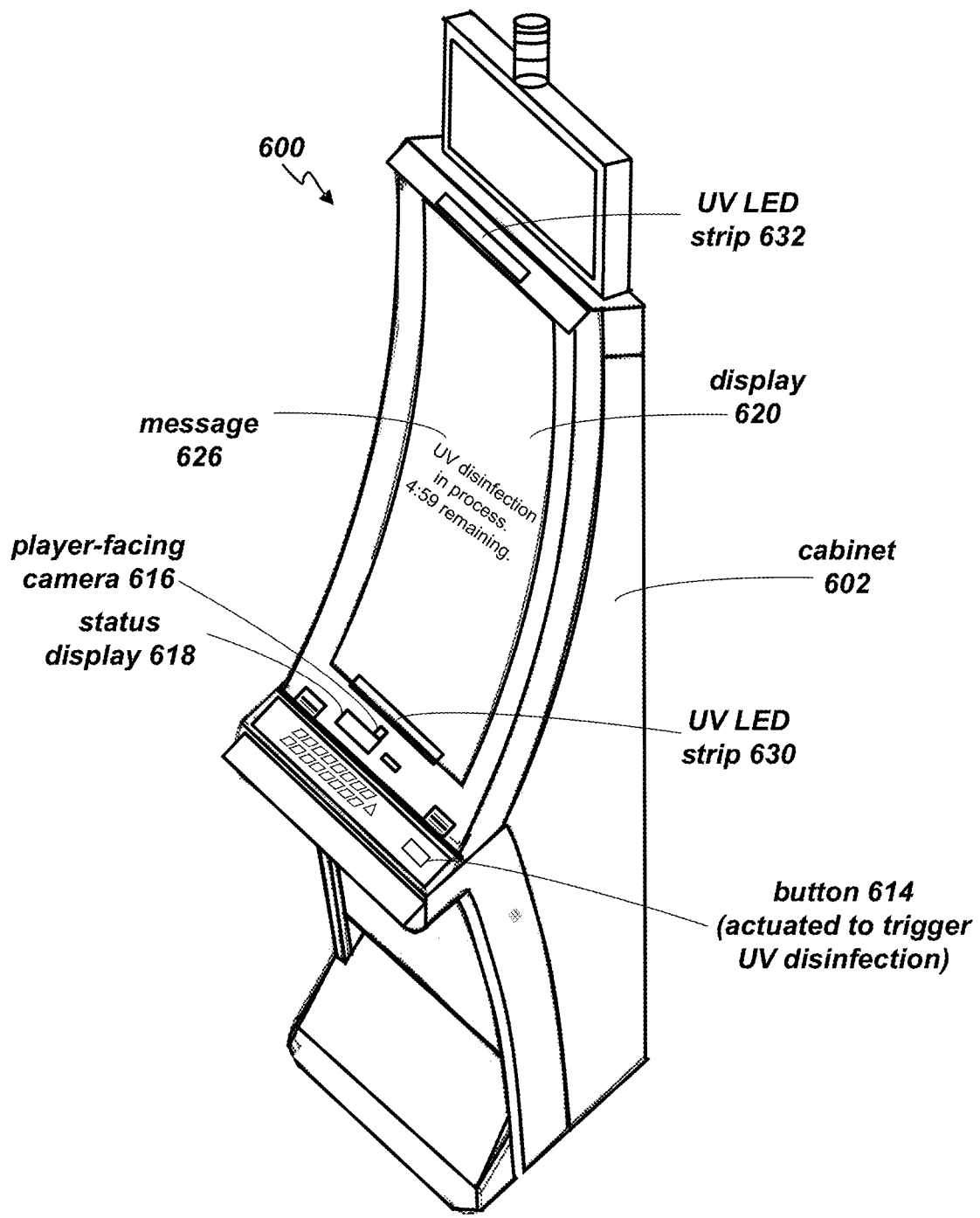
FIG. 6 illustrates an example electronic gaming device that includes UV light sources at edges of a display, as well as other hardware and software features to manage UV disinfection.

FIG. 6 shows an example electronic gaming device 600 that includes UV light sources at edges of a display, as well as other hardware and software features to manage UV disinfection. The electronic gaming device 600 includes a cabinet 602, a button deck 610, and a display 620, which may be a touchscreen display or non-touchscreen display. The electronic gaming device 600 includes a processor, memory, and other components described with reference to FIG. 1. The electronic gaming device 600 is based on the electronic gaming device 104B shown in FIG. 1. Alternatively, the electronic gaming device 600 can have any of the other form factors described in section I for an electronic gaming device. Depending on implementation, the electronic gaming device 600 can also include components described in section X for UV disinfection.

The electronic gaming device 600 includes one or more UV light sources, which are arranged along at least one edge of the display 620 so as to, when activated, emit UV light across at least part of the display 620. In FIG. 6, the electronic gaming device 600 includes two UV LED strips 630, 632, which are arranged along opposite edges of the display 620.

UV light source(s) can be arranged at an edge of a display that is closest to a user position, so as to, when activated, emit UV light away from the user position. In FIG. 6, the first UV LED strip 630 is arranged along the edge of the display 620 closest to the user position. When activated, the UV LED strip 630 generally emits UV light away from the user position, which can reduce exposure to UV light.

UV light source(s) can also be arranged at an edge of a display that is farthest from a user position, so as to, when activated, emit UV light away towards the user position. In FIG. 6, the second UV LED strip 632 is arranged along the edge of the display 620 farthest from the user position. When activated, the UV LED strip 632 generally emits UV light away towards the user position. To address safety concerns, the UV LED strip 632 (and also the UV LED strip 630) can be controlled to emit UV light at a lower intensity or only when the user is not present.

More generally, UV light source(s) can be arranged along one edge of a display, two opposite edges of the display, all but one edge of the display, or all edges of the display. The display can be any type of video display (e.g., LCD, CRT), and it can be the only video display on an electronic gaming device or one of multiple video displays on the electronic gaming device (e.g., a main video display or secondary video display). The display can be a touchscreen display. The display can be a curved display or a straight display. Alternatively, the display can include one or more mechanical reels. The UV light source(s) can be implemented and controlled using any of the approaches described in sections III and IV.

An electronic gaming device can include a reflective shield such as a visor, cone, etc. around the respective UV light source(s) to guide UV light to targeted surfaces. An electronic gaming device can include a reflective shield such as a visor positioned to block at least some of the UV light emitted by UV light source(s), when activated.

UV light source(s) can be embedded in the electronic gaming device 600 or attached to the electronic gaming device 600 using any of the approaches described above. In FIG. 6, the UV LED strips 630, 632 are embedded in the cabinet 602 along edges of the display 620. Alternatively, the UV LED strips can be embedded in the display 620 along edges of the display 620, e.g., as part of a monitor assembly, or otherwise attached to the display 620 or cabinet 602.

The electronic gaming device 600 includes a button 614, player-facing camera 616, status display 618, and message 626 on display 620. The player-facing camera 616, as described in section X, can provide feedback to the electronic gaming device 600. The button 614, status display 618, and message 626 can be implemented and used, alone or with other buttons and/or status displays, as described with reference to corresponding features of the electronic gaming device 400 of FIG. 4.

Figure 7A:
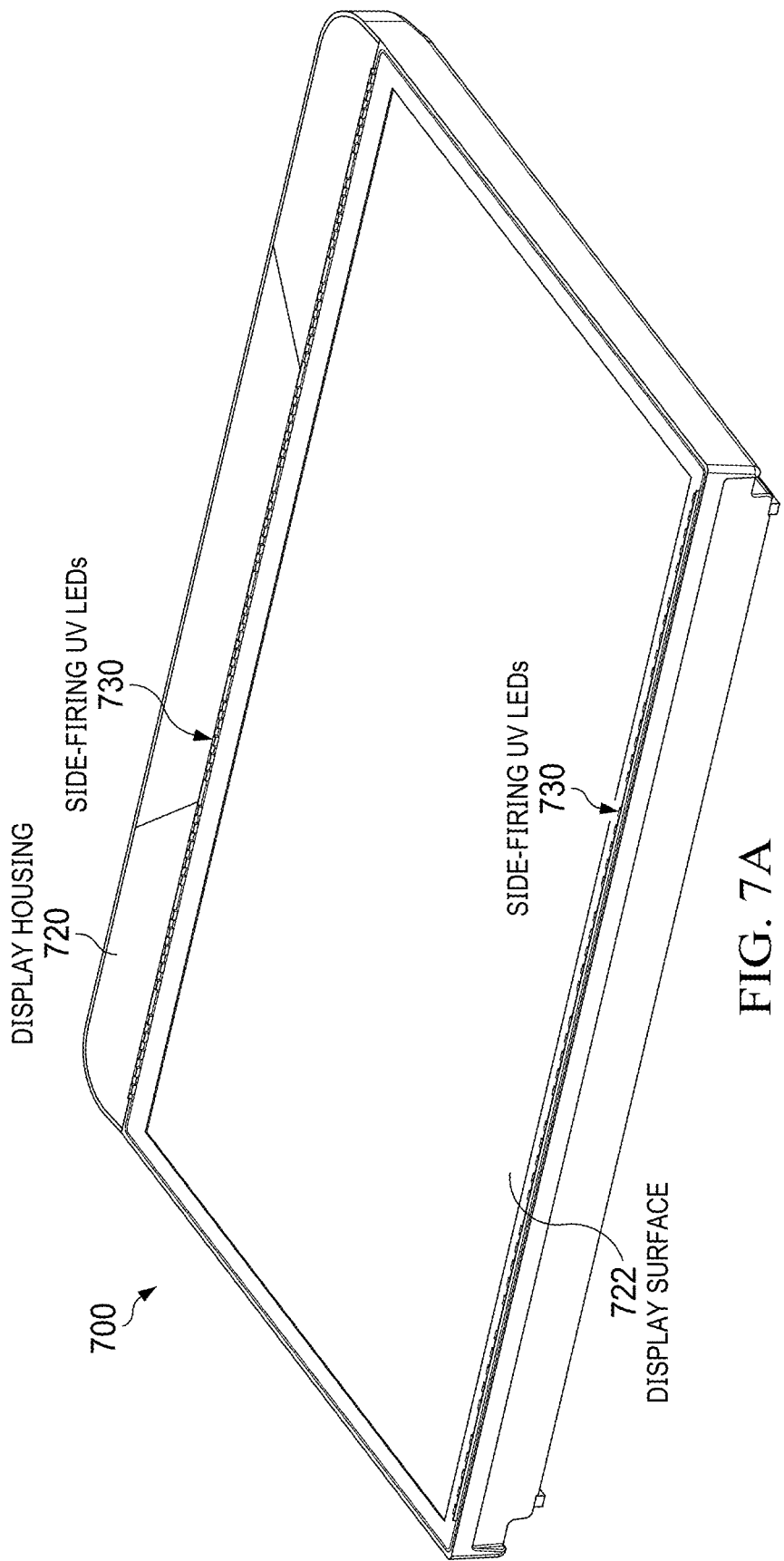
FIGS. 7A-7C, 8A, and 8B illustrate features of example electronic gaming device displays with UV light sources along opposite edges.
Figure 7B:
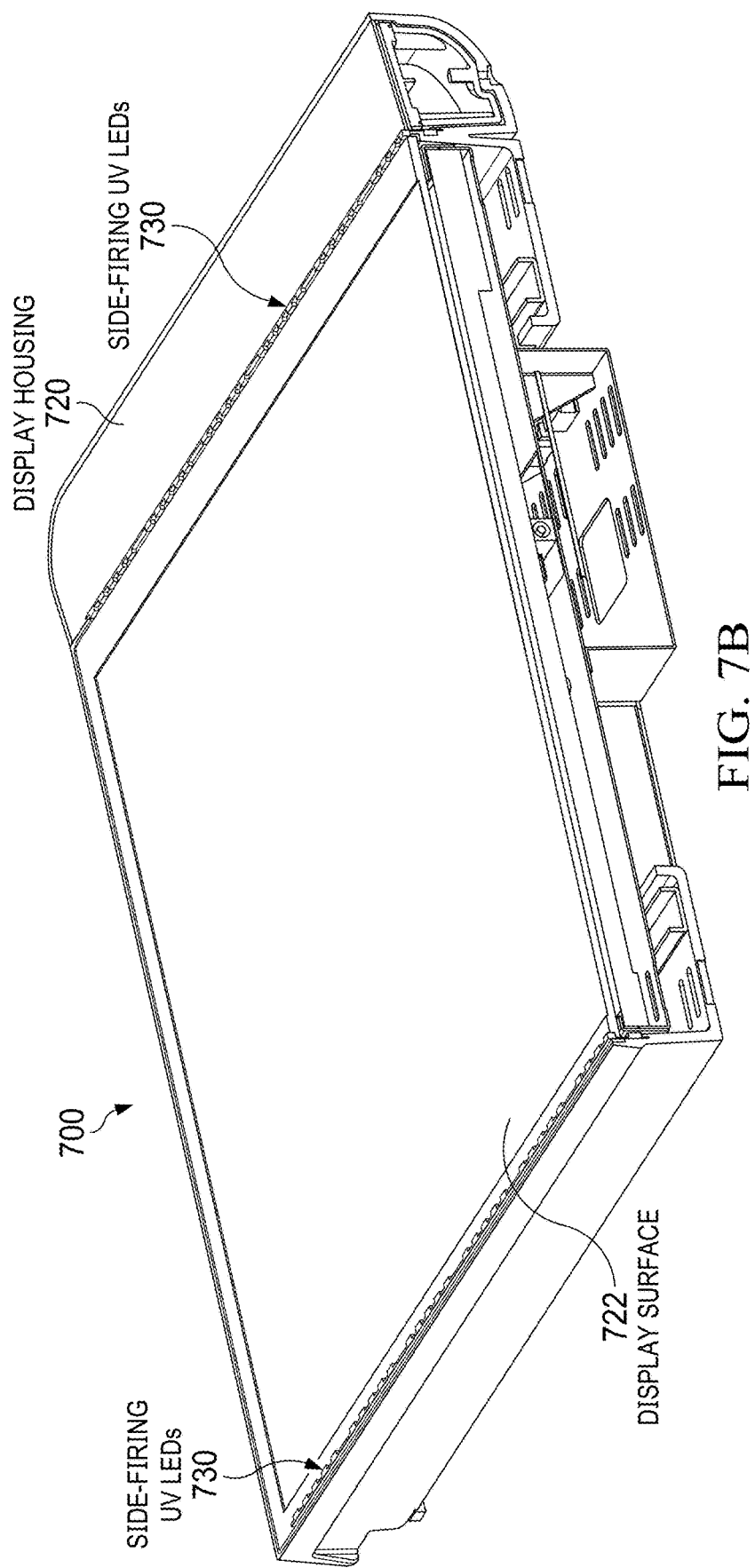
Figure 7C:
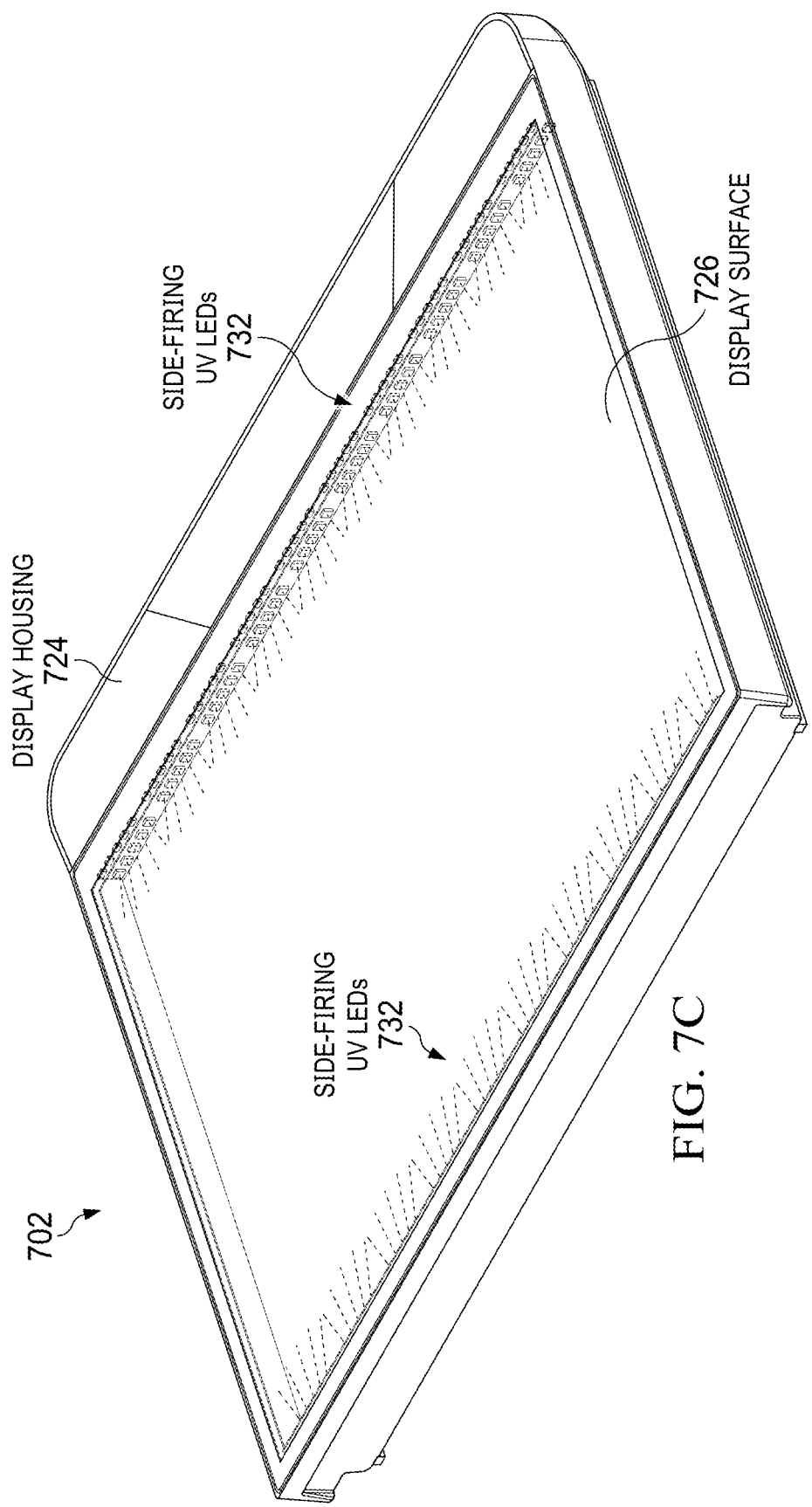
Figure 8A:
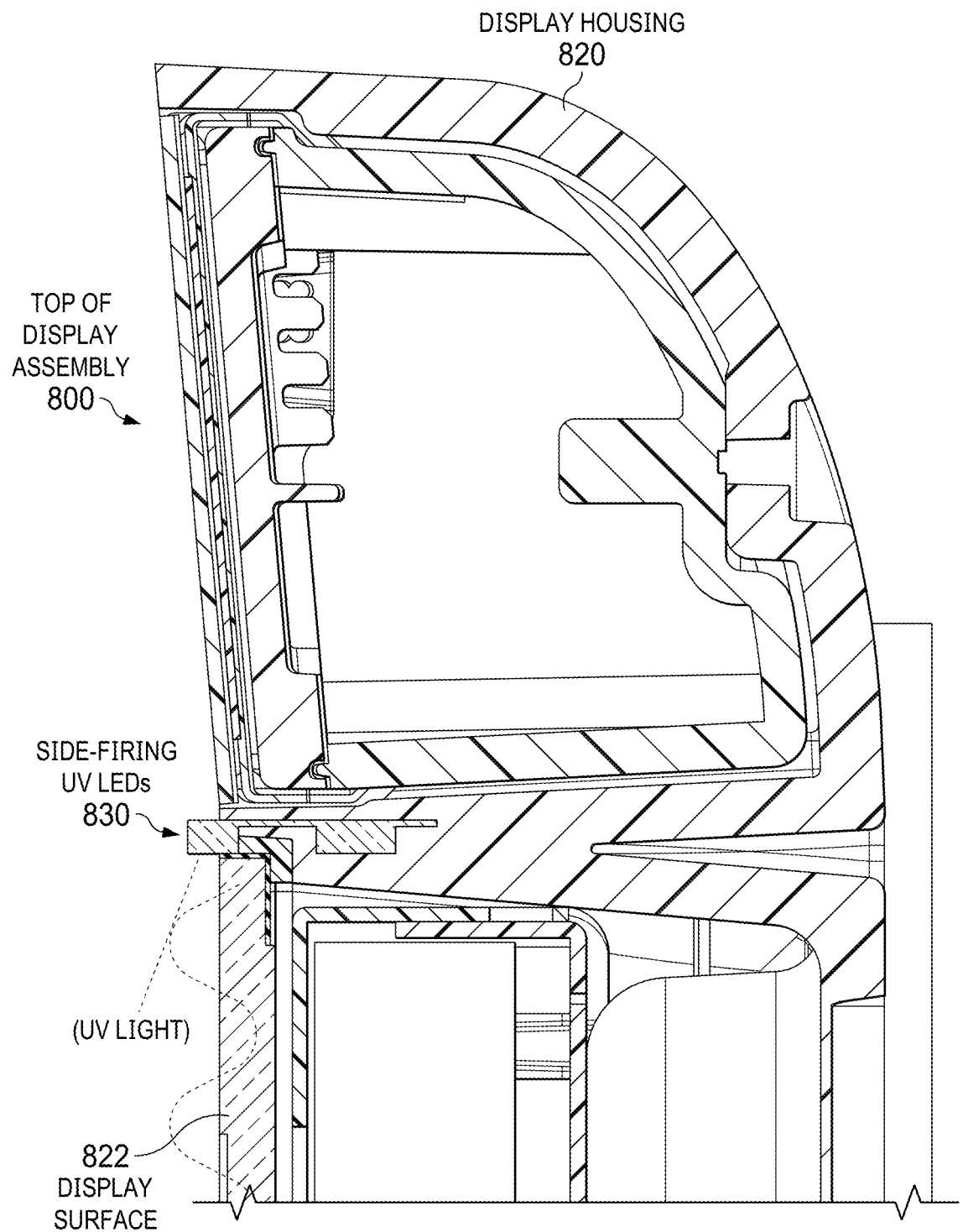
Figure 8B:
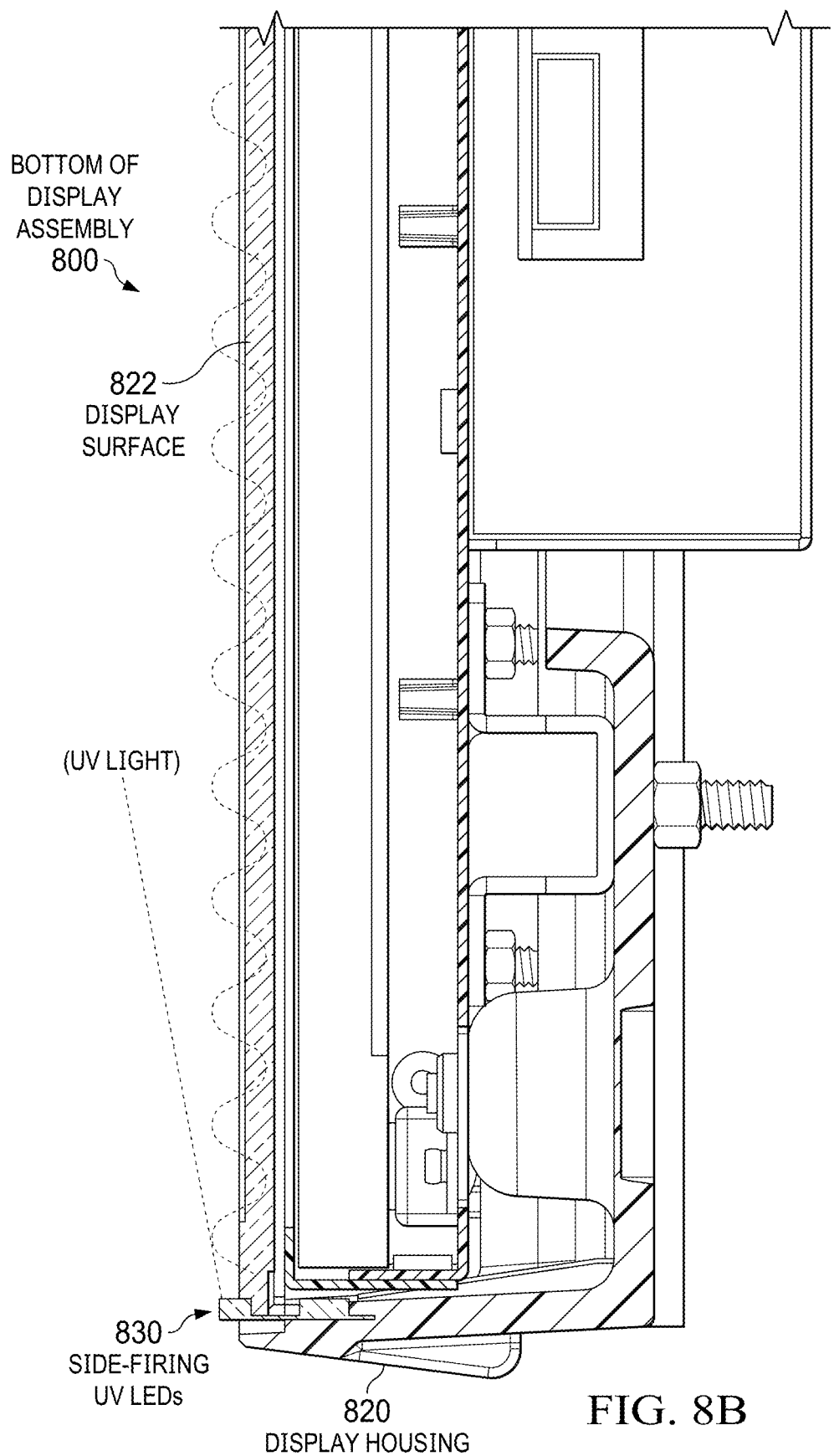

FIGS. 7A-7C, 8A, and 8B illustrate features of example displays with UV light sources along opposite edges of the displays. In FIGS. 7A and 7B, a display assembly 700 includes a display housing 720, display surface 722, and side-firing UV LEDs 730 along opposite edges of the display assembly 700. In FIG. 7C, a display assembly 702 includes a display housing 724, display surface 726, and side-firing UV LEDs 732 along opposite edges of the display assembly 702. In FIGS. 8A and 8B, a display assembly 800 includes a display housing 820, display surface 822, and side-firing UV LEDs 830 along opposite edges of the display assembly 800. Each of the display assemblies 700, 702, 800 is adapted to fit into a corresponding receptacle of an electronic gaming device. For the sake of simplicity, other components of the respective display assemblies 700, 702, 800 are not addressed herein.

Multiple side-firing UV LEDs 730, 732, 830 are embedded in the display housing 720, 724, 820 along the edge of the display surface 722, 726, 822 that will be closest to the user position, with the UV LEDs configured to emit UV light away from the user position to disinfect the display surface 722, 726, 822. Other UV LEDs 730, 732, 830 are embedded in the display housing 720, 724, 820 along the edge of the display surface 722 that will be farthest from the user position, with the other UV LEDs 730, 732, 830 configured to emit UV light away towards the user position to disinfect the display surface 722, 726, 822.

More generally, an apparatus (such as a display assembly, player tracking system assembly, or other assembly), which is adapted to fit into a corresponding receptacle of an electronic gaming device, includes a housing and one or more UV light sources. The UV light source(s) are arranged along at least one edge of the housing so as to, when activated, emit UV light across at least part of the electronic gaming device. The UV light source(s) can be embedded in the housing along the edge(s) or otherwise attached to the housing. The UV light source(s) can be arranged along one edge of the housing, two opposite edges of the housing, all but one edge of the housing or all edges of the housing. The UV light source(s) can be implemented and controlled using any of the approaches described in sections III and IV. The assembly can include other components (e.g., display components, player tracking system components) for the assembly.

VII. Example Electronic Gaming Devices with Side-Firing UV Light Sources at Edge(s) of Display and at Edge(s) of Button Deck.

This section describes example electronic gaming devices that include one or more UV light sources at the edges of button decks and one or more UV light sources at the edges of displays of the electronic gaming devices. In some example implementations, side-firing UV light sources at edges of a button deck and display can effectively disinfect touch points and other surfaces of an electronic gaming device. This section describes example electronic gaming devices in specific form factors. Alternatively, the configurations of UV light sources shown can be implemented in electronic gaming devices having other form factors.

Figure 9:
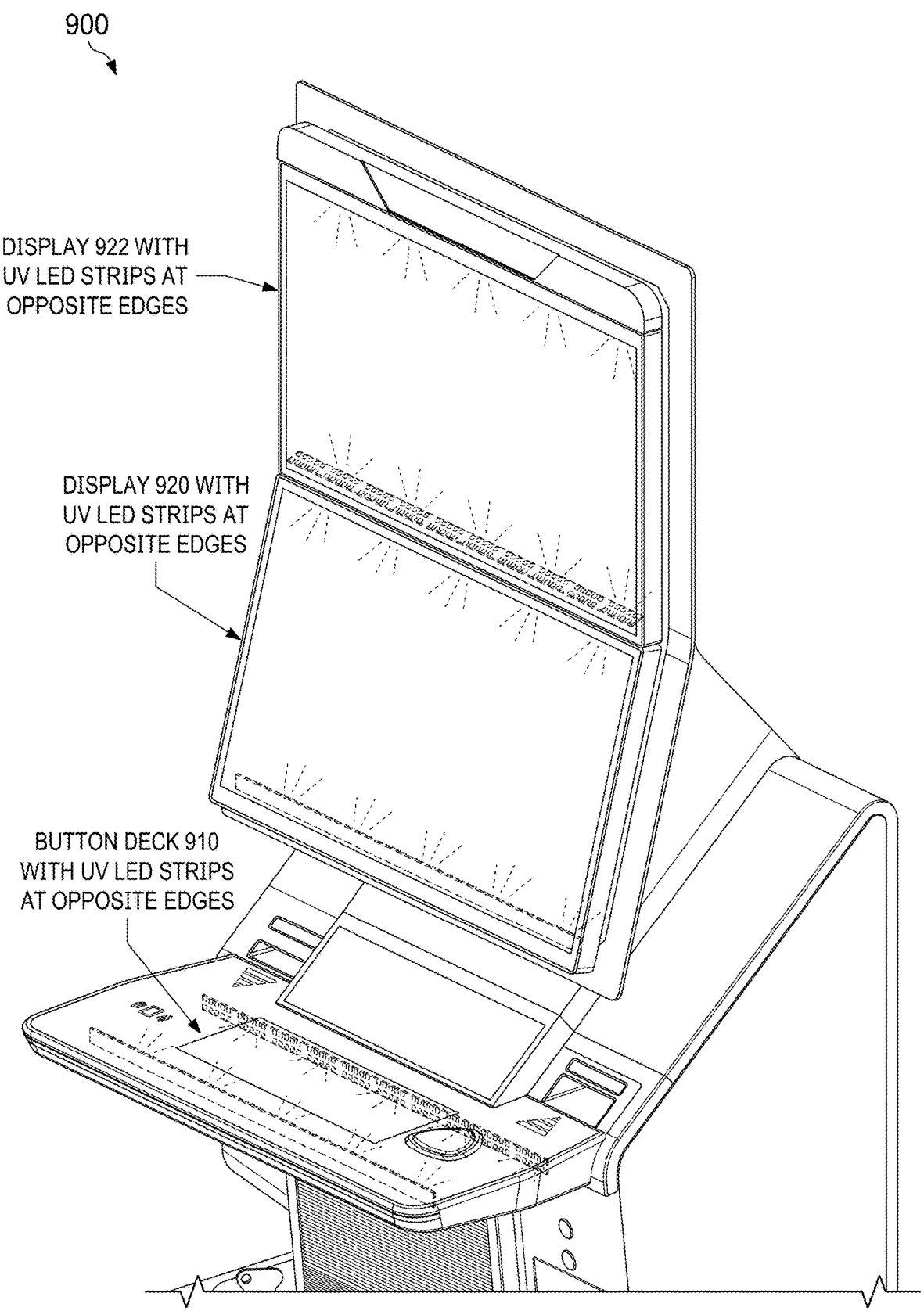
FIG. 9 illustrates an example electronic gaming device that includes UV light sources at edges of a display and at edges of a button deck.

FIG. 9 shows an example electronic gaming device 900 that includes UV light sources at edges of a display and at edges of a button deck. In FIG. 9, the electronic gaming device 900 includes a button deck 910 with UV LED strips at opposite edges, which can be implemented using approaches described in section V. The electronic gaming device 900 includes two displays 920, 922 with UV LED strips at opposite edges, which can be implemented using approaches described in section VI. In FIG. 9, the UV light sources are side-firing LED strips, which are embedded in the cabinet or display assemblies.

Figure 10A:
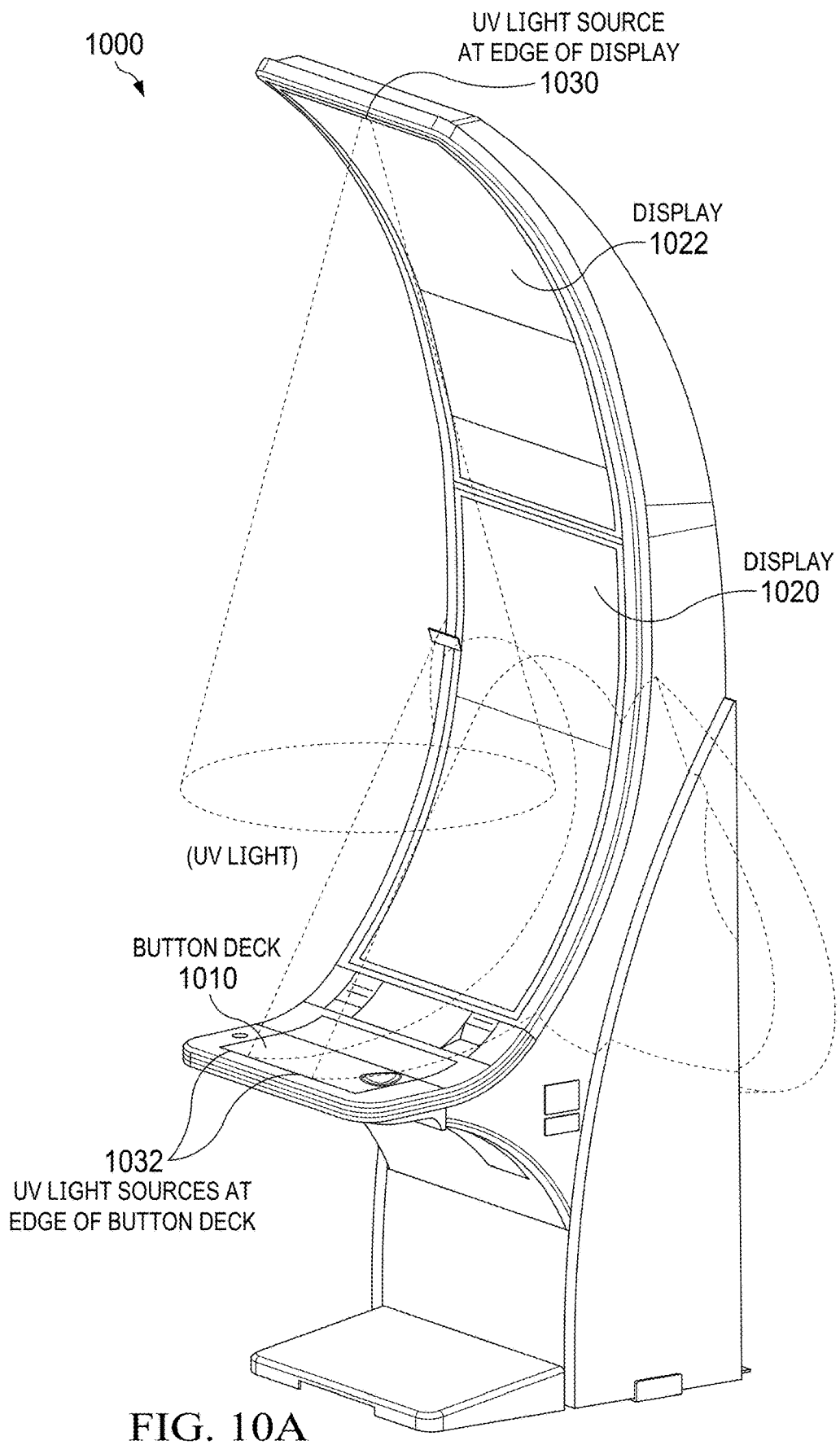
FIGS. 10A-10C illustrate features of an example standalone electronic gaming device having integrated UV light sources adjacent a display and adjacent a button deck.
Figure 10B:
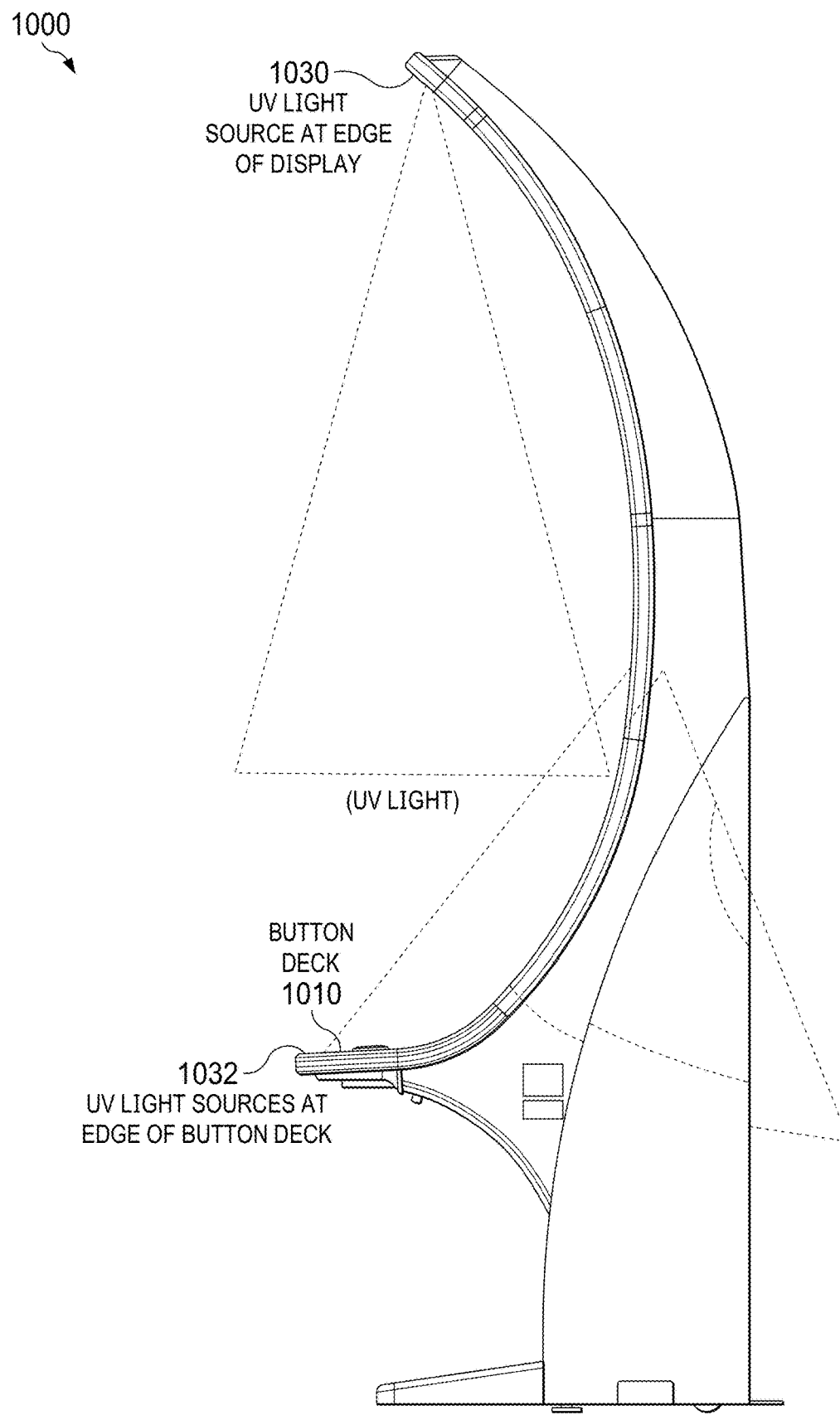
Figure 10C:
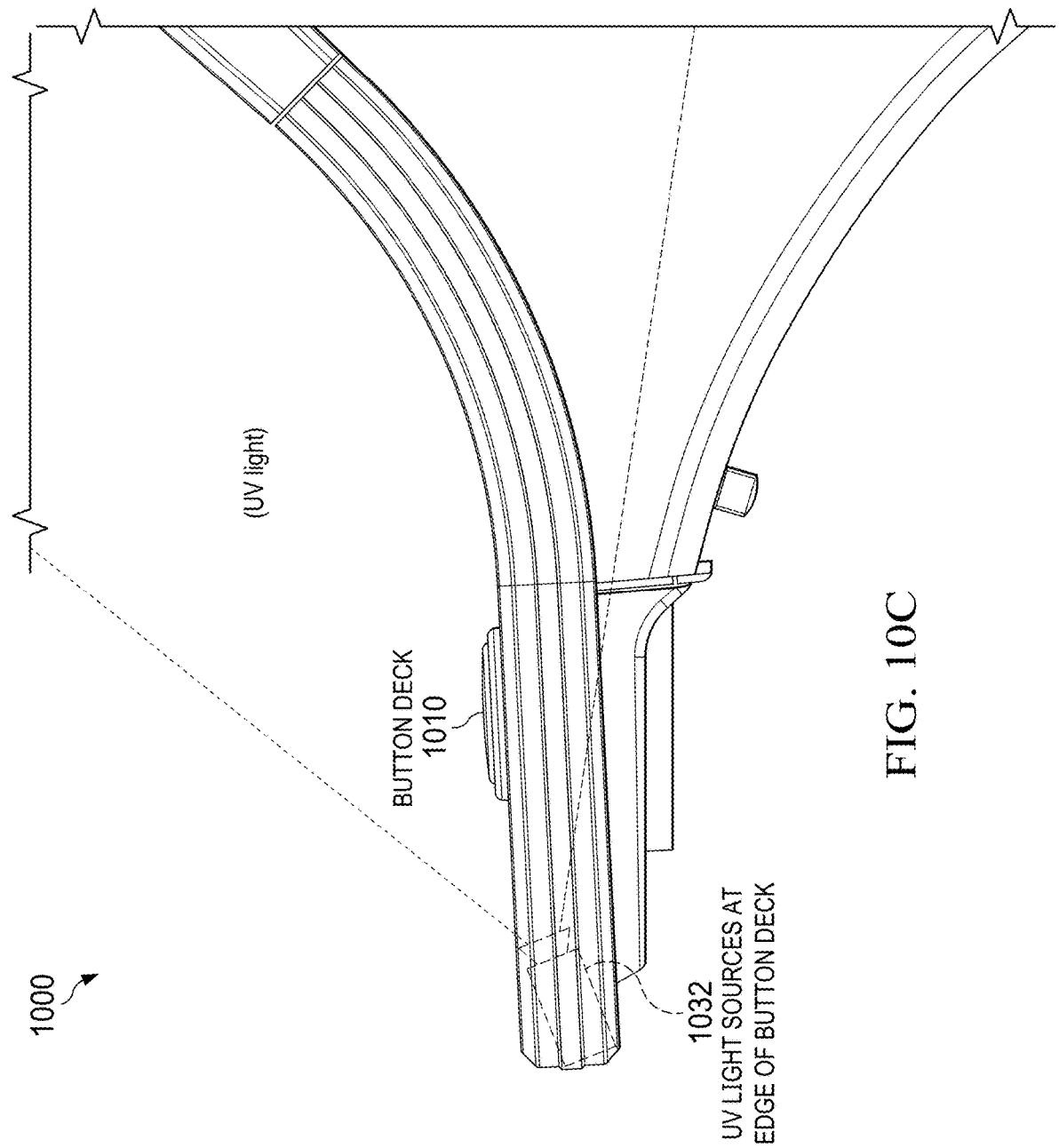

FIGS. 10A-10C illustrate features of an example stand-alone electronic gaming device 1000 having integrated UV light sources adjacent a display and adjacent a button deck. The electronic gaming device 1000 includes a button deck 1010 and two displays 1020, 1022, which can be implemented as described in earlier sections. A UV light source 1030 at the edge of the upper display 1022 is configured to, when activated, emit UV light in a downward direction to disinfect the two displays 1020, 1022 and the button deck 1010. Two UV light sources 1032 at the edge of the button deck 1010 are configured to, when activated, emit UV light over the button deck 1010, disinfecting the button deck 1010 and the lower display 1020. The UV light sources 1030, 1032 can be implemented and controlled using any of the approaches described in sections III and IV.

Figure 11A:
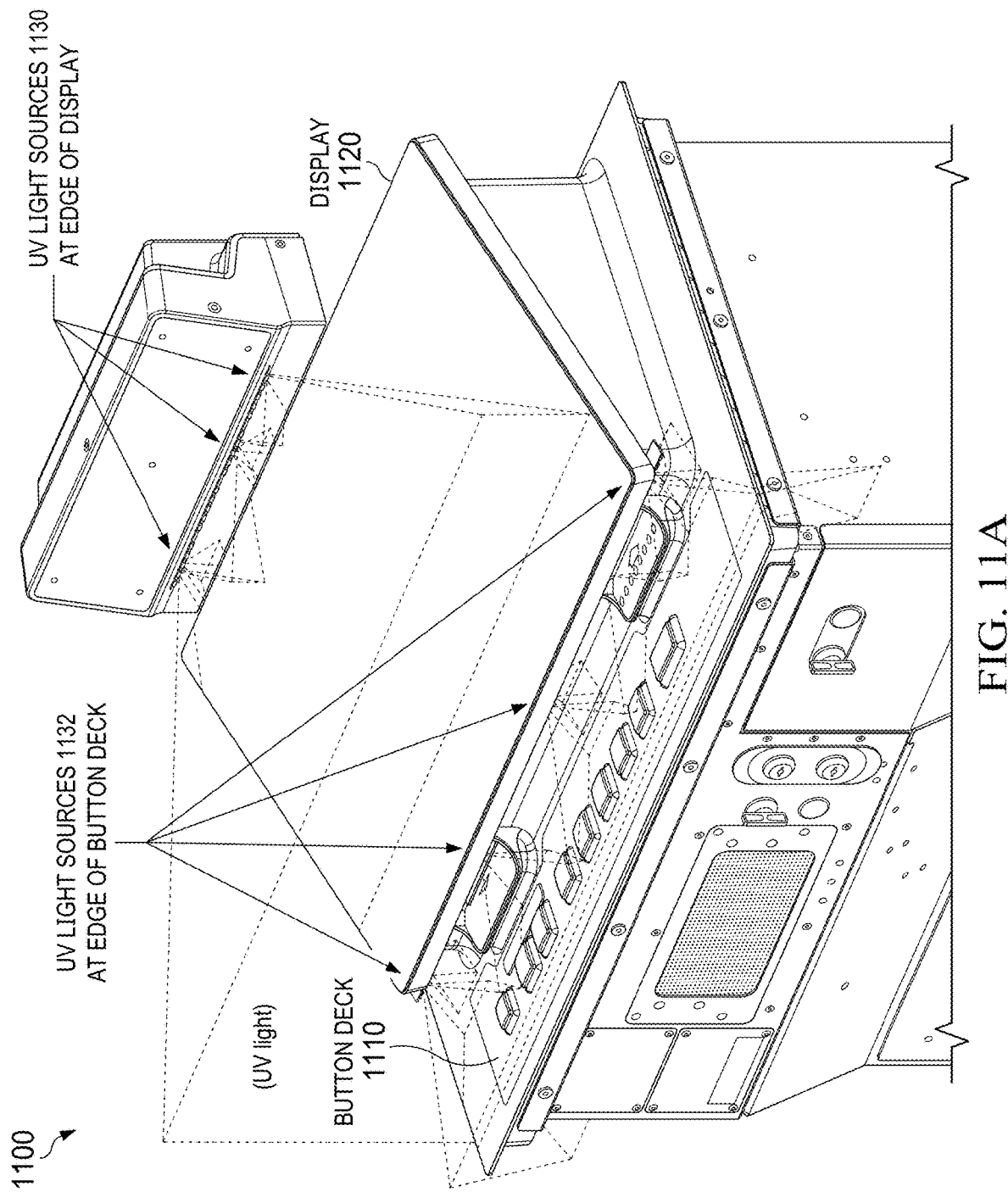
FIGS. 11A and 11B illustrate features of an example bar-top electronic gaming device having integrated UV light sources adjacent a display and adjacent a button deck.
Figure 11B:
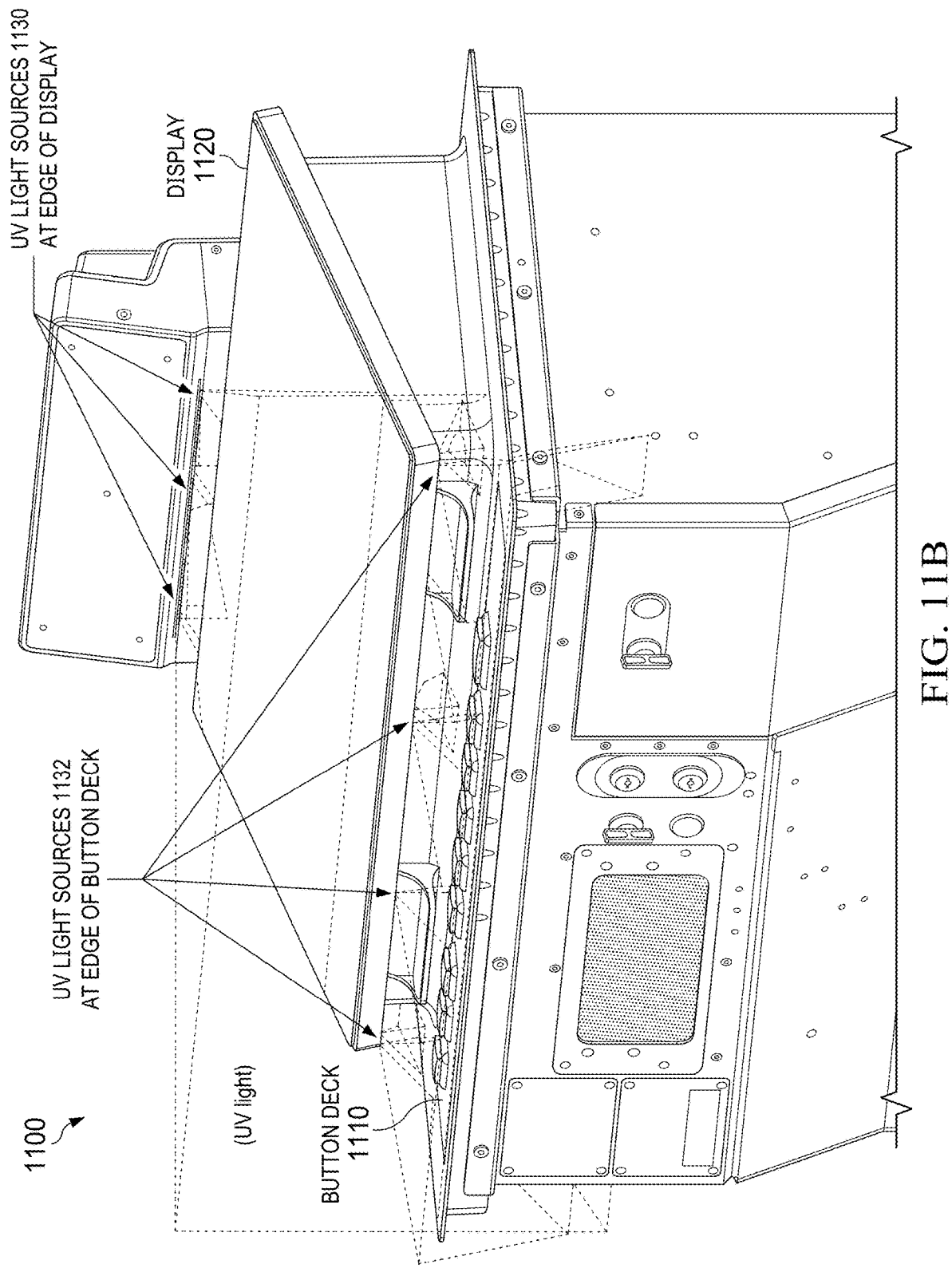

FIGS. 11A and 11B illustrate features of an example bar-top electronic gaming device 1100 having integrated UV light sources adjacent a display and adjacent a button deck. The electronic gaming device 1100 includes a button deck 1110 and a display 1120, which can be implemented as described in earlier sections. UV light sources 1130 at the edge of the display 1120 are configured to, when activated, emit UV light in a downward and outward direction to disinfect the display 1120. UV light sources 1132 at the edge of the button deck 1110 are configured to, when activated, emit UV light in a downward and outward direction over the button deck 1110, disinfecting the button deck 1110. The UV light sources 1130, 1132 can be implemented and controlled using any of the approaches described in sections III and IV.

VIII. Example Electronic Gaming Devices with Multiple UV Disinfection Modes.

This section describes example electronic gaming devices that can use any of multiple available UV disinfection modes. The different UV disinfection modes can be calibrated for different scenarios, such as deeper UV disinfection at night when money is withdrawn from an electronic gaming device or when the electronic gaming device is off-line and people are not around, or lighter UV disinfection when the electronic gaming device is idle between gaming sessions or in response to a user demand.

Different UV disinfection modes reflect different decisions to balance factors such as germicidal effectiveness, safety to humans, energy use, cost of implementation, and downtime for an electronic gaming device. In general, germicidal effectiveness is increased, up to a point of diminishing returns, by using UV light in the UV-C range, at a higher intensity and/or closer distance to touch points, over a longer duration, and over all of the surfaces of an electronic gaming device. Increasing germicidal effectiveness by using high-intensity UV light and performing UV disinfection over a longer duration and/or over more surfaces tends to increase energy use and increase downtime for an electronic gaming device, assuming it cannot be played during such UV disinfection. Also, if safety precautions are not taken, increasing germicidal effectiveness by using UV light in the UV-C range, using high-intensity UV light, and/or performing UV disinfection over a longer duration can also increase safety risks to humans.

An example electronic gaming device includes a cabinet, a display, a button deck, and one or more UV light sources. The electronic gaming device can also include a processor, memory, and other components described with reference to FIG. 1. Depending on implementation, the electronic gaming device can include components described in section X for UV disinfection. The UV light source(s) are arranged so as to, when activated, emit UV light across at least part of the electronic gaming device. The UV light source(s) can be implemented and controlled using approaches described in sections III and IV.

In general, the electronic gaming device is configured to select a UV disinfection mode from among multiple available UV disinfection modes. The multiple available UV disinfection modes can differ from each other in terms of duration, scope of coverage over the electronic gaming device, intensity of the UV light, and/or another factor.

For example, the multiple available UV disinfection modes include two or more UV disinfection modes. A first UV disinfection mode has a first duration, a first scope of coverage, and a first intensity of the UV light. A second UV disinfection mode has a second duration, a second scope of coverage, and a second intensity of the UV light. The second UV disinfection mode differs from the first UV disinfection mode in some way. For example, the second duration is longer than the first duration, the second scope of coverage is wider than the first scope of coverage, and/or the second intensity of the UV light is higher than the first intensity of the UV light. A third UV disinfection mode can have a third duration, a third scope of coverage, and a third intensity of the UV light, with the third UV disinfection mode differing from the first UV disinfection mode and the second UV disinfection mode in some way.

In some example implementations, the multiple available UV disinfection modes include (1) a user-initiated UV disinfection mode triggered in response to user input, (2) an idle-time disinfection mode triggered in response to inactivity at the electronic gaming device, and (3) an offline UV disinfection mode triggered in response to deactivation/disabling of the electronic gaming device or user input during deactivation/disabling of the electronic gaming device. Alternatively, the multiple available UV disinfection modes include other and/or additional UV disinfection modes.

The UV light source(s) can be arranged along edge(s) of a button deck (as described in section V), along edge(s) of a display (as described in section VI), or arranged at other locations (e.g., as described in section VII). Alternatively, the UV light source(s) can be arranged along a movable part of the electronic gaming device (as described in section IX).

IX. Example Electronic Gaming Devices with Movable Parts for UV Disinfection.

This section describes example electronic gaming devices that include one or more UV light sources on a movable part, which moves into position for UV disinfection but returns to a less obtrusive or even hidden position when not in use for UV disinfection. The movable part can be added to an electronic gaming device to retrofit the electronic gaming device for UV disinfection, or the movable part can be included as part of an original electronic gaming device.

An example electronic gaming device includes a cabinet, a display, a button deck, and one or more UV light sources. The electronic gaming device can also include a processor, memory, and other components described with reference to FIG. 1. Depending on implementation, the electronic gaming device can include components described in section X for UV disinfection. The UV light source(s) are arranged along a movable part of the electronic gaming device so as to, when activated, emit UV light across at least part of the electronic gaming device. The UV light source(s) can be implemented and controlled using approaches described in sections III and IV.

The electronic gaming device and movable part (with UV light source(s)) can be configured so that the movable part fits, in a nesting manner, into the electronic gaming device during normal use of the electronic gaming device. For example, the movable part fits into one or more recessed portions of the cabinet of the electronic gaming device (e.g., at the top of the cabinet, or at a side of the cabinet, or on the front of the cabinet). Or, the movable part fits into one or more recessed portions of a monitor assembly. Alternatively, the electronic gaming device and movable part (with UV light source(s)) can be configured so that the movable part swings to a position behind the electronic gaming device or on the side of the electronic gaming device when not in use. The movable part can be physically connected to the electronic gaming device with various types of hinges and pivots, as described below.

In some example implementations, the movable part is an arm assembly adapted to swing, from one or more pivot points at an edge of the display, outward over at least part of the electronic gaming device. The UV light source(s) are attached to the arm assembly. The arm assembly can be electrically connected to the electronic gaming device within a physical connector to the electronic gaming device. A reflective shield such as a visor around the UV light source(s) can reflect UV light towards the electronic gaming device.

Figure 12A:
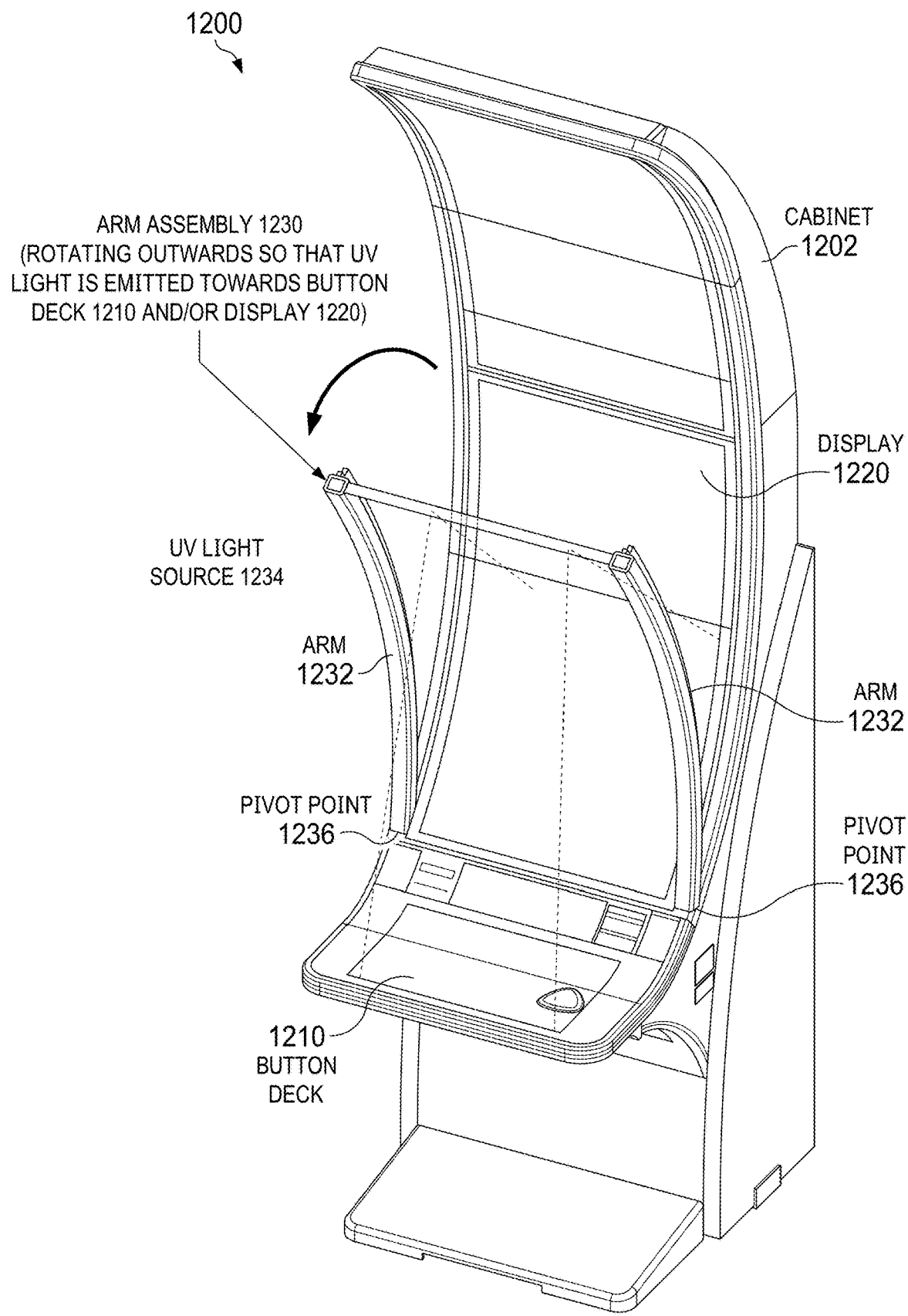
FIGS. 12A and 12B illustrate features of an example arm assembly, including UV light sources, which is adapted to fit within an example standalone electronic gaming device when not in use.
Figure 12B:
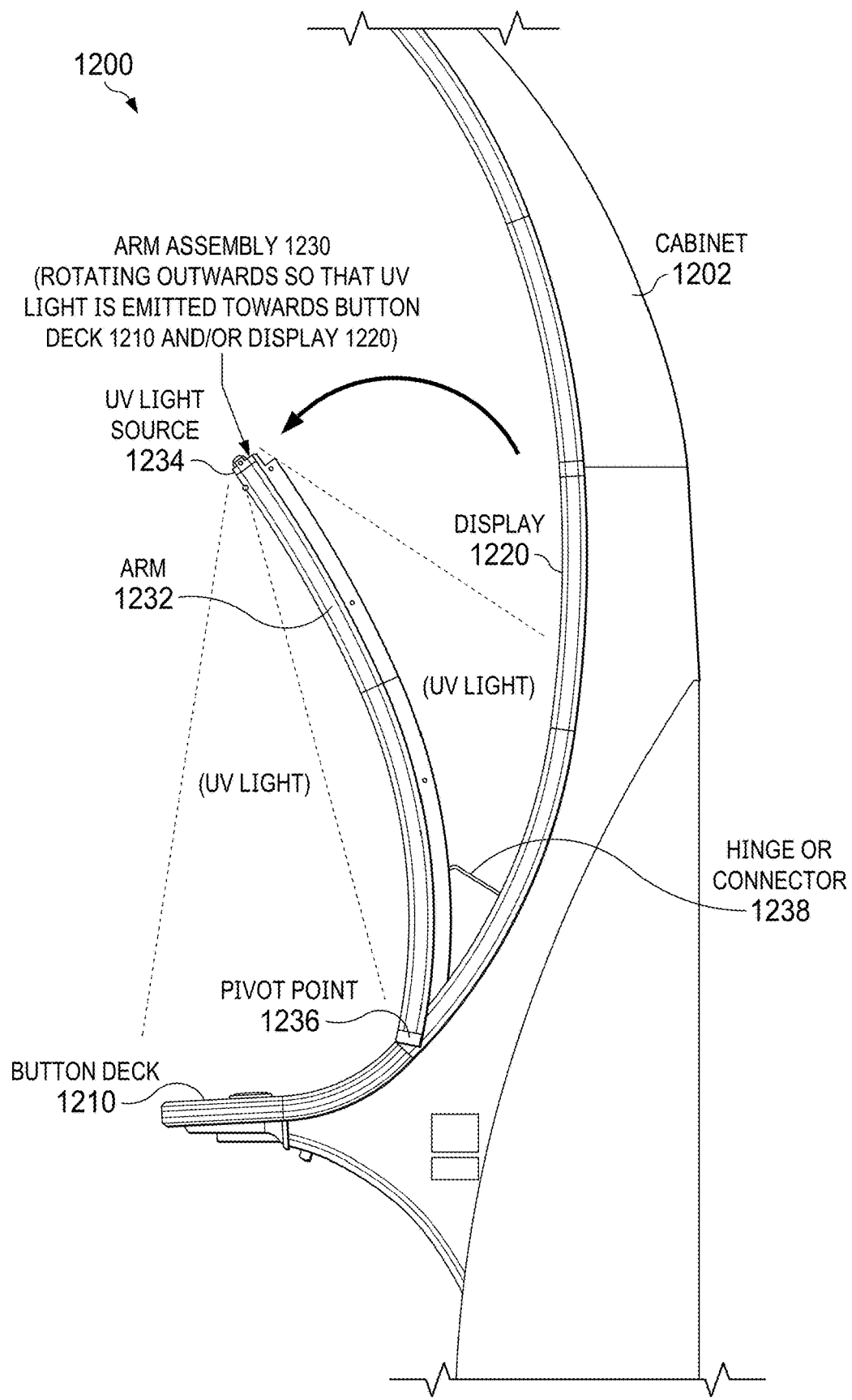

FIGS. 12A and 12B show features of an example arm assembly 1230 of an electronic gaming device 1200. The electronic gaming device 1200 includes a cabinet 1202, button deck 1210, display 1220, and arm assembly 1230. The arm assembly 1230 includes a UV light source 1234 attached to two arms 1232. The two arms 1232 are attached to the electronic gaming device 1200 at pivot points 1236 at the edge of the display 1220. In operation, the arm assembly 1230 rotates outward so that UV light is emitted towards the button deck 1210 and at least part of the display 1220. When not in use, the arms 1232 of the arm assembly 1230 are adapted to fit within recessed portions along the edges of the electronic gaming device 1200, and the UV light source 1234 is adapted to fit within a recessed portion above the display 1220. A hinge or other connector 1238 can limit the extent of the arms 1232 swinging away from the electronic gaming device 1200. A reflective shield (not shown) around the UV light source 1234 can reflect UV light towards the electronic gaming device 1200.

In other example implementations, the movable part is an arm assembly adapted to swing, from one or more pivot points, over at least part of the electronic gaming device. The UV light source(s) are attached to the arm assembly. For example, the arm assembly can swing from a pivot point at the top of the electronic gaming device or on a side of the electronic gaming device. The arm assembly can be electrically connected to the electronic gaming device within a physical connector to the electronic gaming device.

In still other example implementations, the movable part is a bar assembly adapted to roll, along tracks, over at least part of an electronic gaming device. The UV light source(s) are attached to the bar assembly. A reflective shield around the UV light source(s) can reflect UV light towards the electronic gaming device. For example, the tracks run along the front, side edges of the electronic gaming device. The bar assembly can be electrically connected to the electronic gaming device within a physical connector to the electronic gaming device.

Figure 13A:
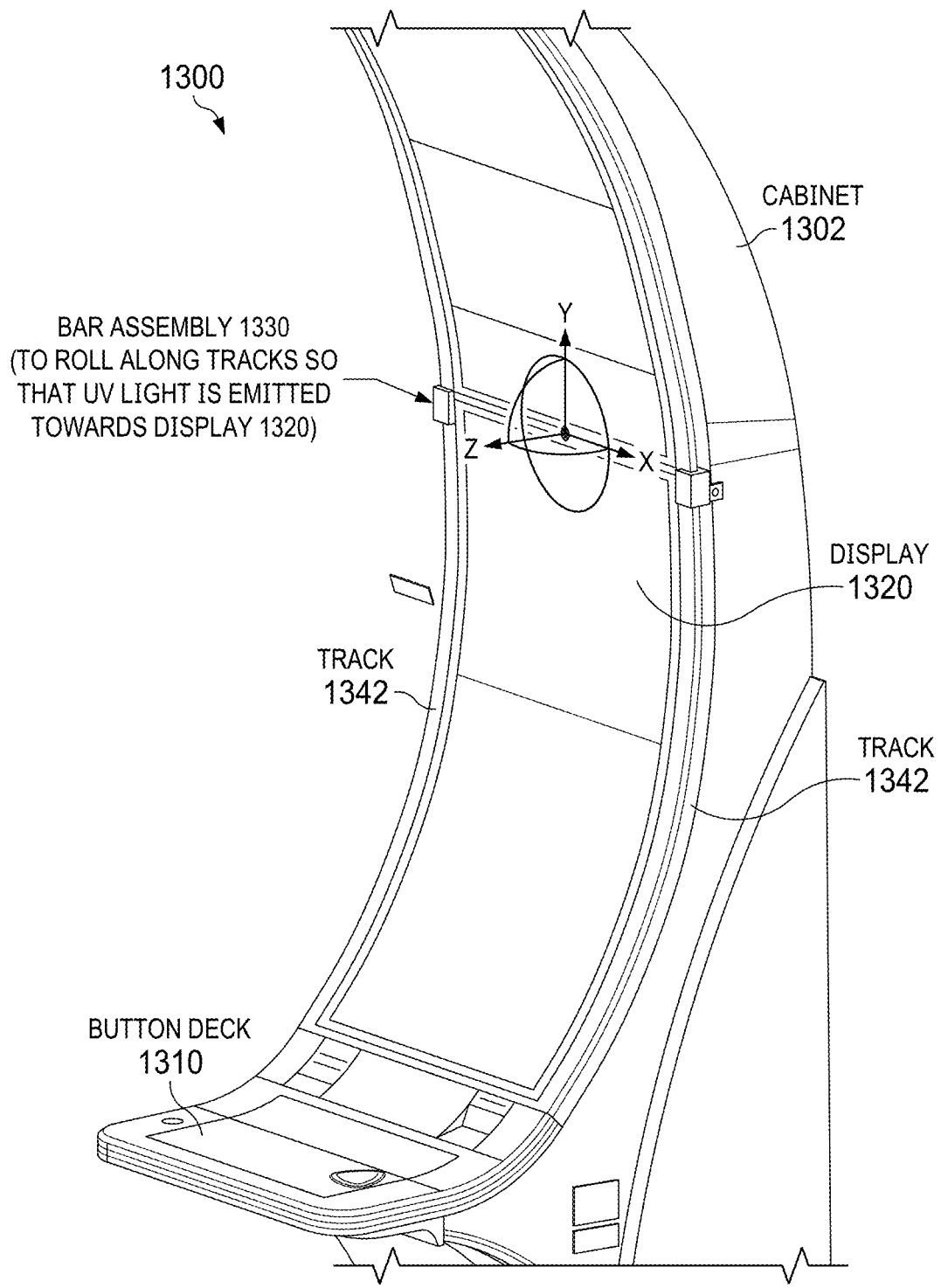
FIGS. 13A-13C illustrate features of an example bar assembly, including UV light sources, which is adapted to roll along tracks on an example standalone electronic gaming device.
Figure 13B:
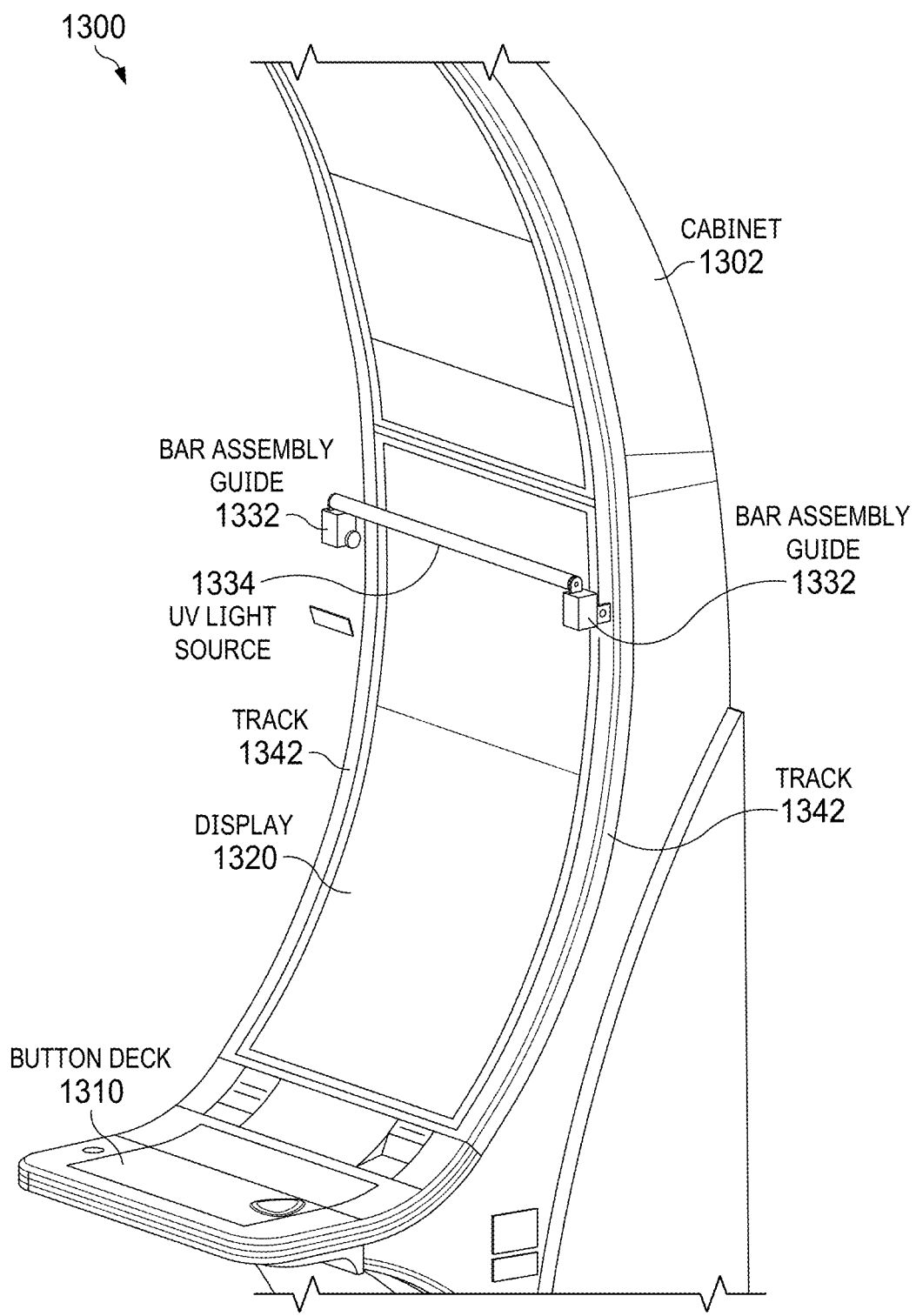
Figure 13C:
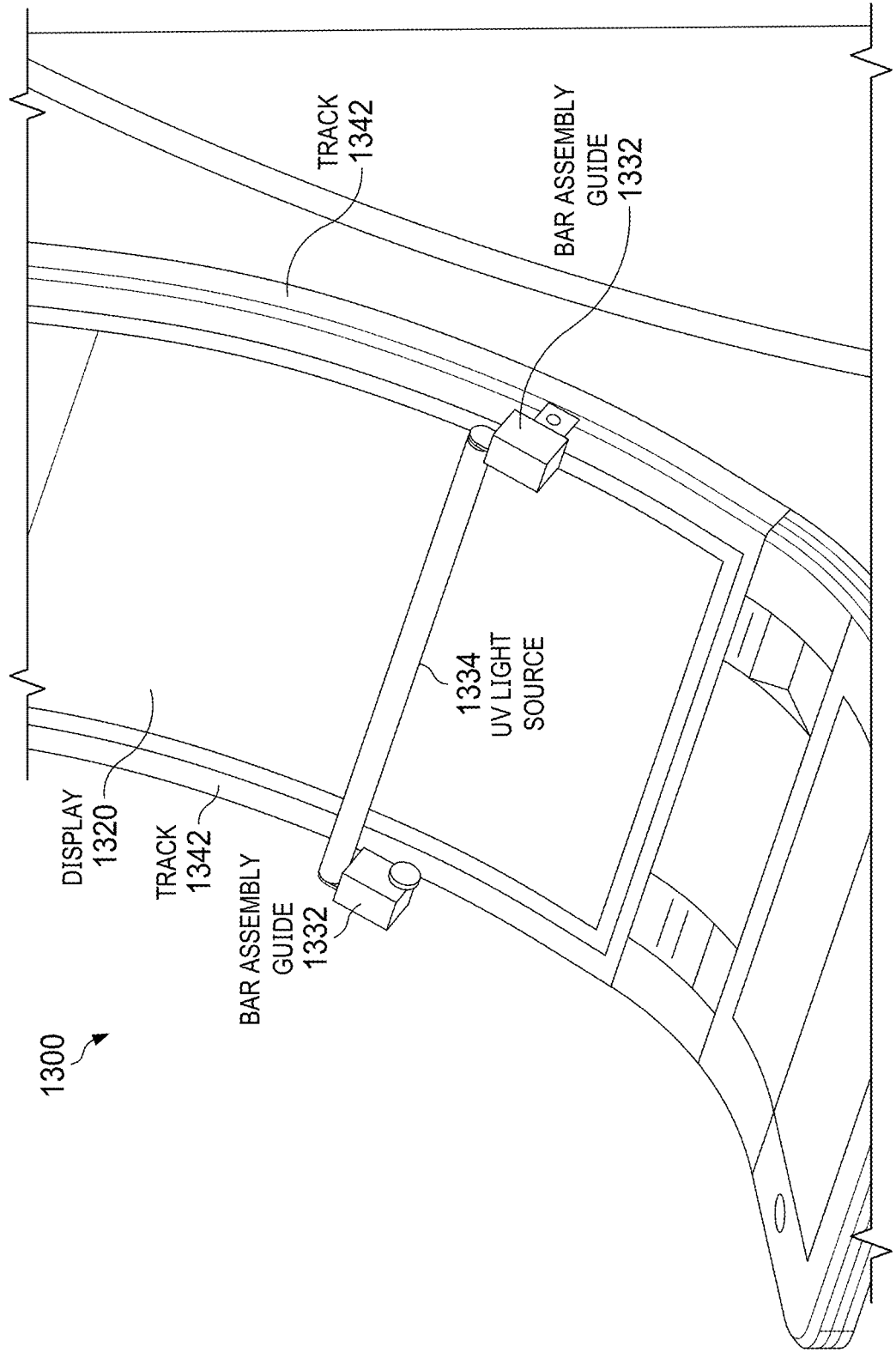

FIGS. 13A-13C show features of an example bar assembly 1330, which is adapted to roll along tracks 1342 on an electronic gaming device 1300. The electronic gaming device 1300 includes a cabinet 1302, button deck 1310, display 1320, and bar assembly 1330. The tracks 1342 follow edges of the electronic gaming device 1300 along the display 1320. The bar assembly 1330 includes a UV light source 1334, which is attached to two bar assembly guides 1332. The two bar assembly guides 1332 roll along the tracks 1342 as the UV light source 1334 passes over the display 1320, emitting UV light towards the display 1320. A reflective shield (not shown) around the UV light source 1334 can reflect UV light towards the electronic gaming device 1300.

In still other example implementations, the movable part is a cover assembly adapted to swing, at a hinge at the top of an electronic gaming device, over at least part of the electronic gaming device. The cover assembly can include a housing such as a rigid shell, with the UV light source(s) attached to the underside of the housing. The underside of the housing can be made of, or be coated with, material to reflect UV light back to the electronic gaming device. Alternatively, the cover assembly can include multiple panels, which are flexibly connected, with the UV light source(s) attached to the undersides of the respective panels. The undersides of the respective panels can be made of or have a reflective coating. The cover assembly can be electrically connected to the electronic gaming device through a wired or wireless charging connection, e.g., through or near a player tracking system interface, or within a physical connector to the electronic gaming device.

X. Variations for Example Electronic Gaming Devices with UV Light Sources.

This section describes variations of the preceding electronic gaming devices with UV light sources, with additional hardware and/or software features.

An electronic gaming device with UV light sources typically includes a cabinet, a button deck, and a display. At least part of the cabinet can be made of or coated with material adapted to absorb UV light, so as to reduce reflection of UV light away from the electronic gaming device. The electronic gaming device also typically includes a processor and memory. An electronic gaming device with UV light sources can include other components, as described with reference to FIG. 1, for example, a player tracking system interface, a network connection, a speaker, an additional display, a ticket-out printer, a bill validator or other ticket-in reader, and/or a card reader. The electronic gaming device can also include a wireless charging pad (to charge a user's mobile device) and/or a disinfection assembly (to disinfect a user's mobile device).

In general, an electronic gaming device with UV light source(s) can have any of the form factors described in section I for an electronic gaming device. For example, the electronic gaming device can be adapted for use as a bar counter, for use as a standalone device, or for use as part of a bank of electronic gaming devices.

In some example implementations, an electronic gaming device with UV light sources includes one or more cameras. For example, the electronic gaming device can include a camera oriented towards a user position as well as logic, implemented with software and/or hardware, configured to detect a warning condition of a user at the user position. The camera can be a hyperspectral camera or other camera. The camera can be integrated into the cabinet of the electronic gaming device (e.g., in a recessed portion). Or, the camera can fit into a bracket of the electronic gaming device (e.g., as part of a player tracking system interface assembly). A player tracking system interface is typically within arm's reach of a user, which makes the orientation and distance to the user suitable for viewing the user. In some example implementations, a player tracking system interface includes a port or bracket into which the camera can be installed, so that the camera fits next to the player tracking system interface. Or, the camera can be installed into an existing player tracking system as an after-market component. Or, the camera can be integrated into a player tracking system. Or, the camera can be installed behind a display or as part of a display assembly. Alternatively, the camera can be integrated into or attached to the electronic gaming device in some other way.

Using feedback from the camera, the logic can detect a high temperature of the user at the user position (i.e., a temperature higher than a threshold temperature) or detect some other type of warning condition. The logic can be further configured to, in response to detection of a warning condition, (1) send a notification of the warning condition to a monitoring service, alerting staff, and/or (2) trigger a UV disinfection cycle (e.g., at the next idle time). In this way, feedback from the camera can be used to decide whether or not to activate UV light source(s) for UV disinfection. Feedback from the camera can also be used to select a UV disinfection mode or otherwise control UV disinfection.

As another example, an electronic gaming device with UV light sources can include a camera oriented towards a button deck or display as well as logic, implemented with software and/or hardware, configured to detect pathogens, heat spots, or some other condition. The camera can be a hyperspectral camera or other camera. A hyperspectral camera can collect data from many different frequencies across the electromagnetic spectrum. Collected data can be analyzed using artificial intelligence to help identify pathogens. For sensitive measurements, the camera can be used when the electronic gaming device is offline, to reduce interference from heat or light from the display or other components of the electronic gaming device. The camera can be integrated into the cabinet of the electronic gaming device (e.g., in a recessed portion) or attached to a bracket. Alternatively, the camera can be integrated into or attached to the electronic gaming device in some other way.

Using feedback from the camera, the logic can detect heat spots, detect pathogens, or detect some other condition. The logic can be further configured to, in response to detection of pathogen or warning condition, (1) send a notification to a monitoring service, alerting staff, and/or (2) trigger a UV disinfection cycle (e.g., at the next idle time). The logic can be further configured to, in response to detection of heat spots, trigger a UV disinfection cycle (e.g., at the next idle time) focusing on the heat spots/touch points. In this way, feedback from the camera can be used to decide whether or not to activate UV light source(s) for UV disinfection. Feedback from the camera can also be used to select a UV disinfection mode. More generally, based at least in part on feedback from the camera, the logic can decide where to focus UV disinfection (scope of coverage), adjust the intensity of the UV light, adjust the wavelength of the UV light, and/or adjust the duration of UV disinfection.

XI. Example UV Disinfection Shield Assemblies.

This section describes examples of UV disinfection shield assemblies configured for placement over an electronic gaming device. A UV disinfection shield assembly includes one or more UV light sources, which are arranged so as to, when activated, emit UV light towards at least part of an electronic gaming device. An electronic gaming device without integrated UV light source(s) can be retrofitted with a UV disinfection shield assembly, or can be selectively covered with a UV disinfection shield assembly, to enable UV disinfection. UV disinfection shield assemblies can be adapted for different form factors of electronic gaming devices. The UV light source(s) can be implemented as described in section III.

An example UV disinfection shield assembly includes multiple panels. Each of the panels includes an array of UV light sources arranged on a side of the panel so as to, when activated in place over at least part of an electronic gaming device, emit UV light towards the at least part of the electronic gaming device. Each of the panels has dimensions and a shape that at least generally follows contours of a corresponding part of the electronic gaming device. A panel can be rigid (e.g., made of inflexible plastic) or flexible (e.g., made of cloth or flexible plastic)

The UV disinfection shield assembly also includes a cover that flexibly connects the multiple panels. In this way, even if the panels are themselves inflexible, the panels can move or fold relative to each other to make storage and placement of the UV disinfection shield assembly easier. The undersides of the panels and the cover can be made of or coated with a material adapted to reflect UV light. The edges of the cover can include folds or extensions that fit over the electronic gaming device, helping to block the escape of UV light.

The UV disinfection shield assembly can also include, for a panel, a reflective shield such as a visor that encloses at least part of the panel. The shield is arranged so as to, when the UV light sources are activated in place over the at least part of an electronic gaming device, reflect the UV light towards the at least part of the electronic gaming device and block escape of the UV light away from the at least part of the electronic gaming device.

The UV disinfection shield assembly can also include a power supply. The power supply is configured to supply electrical current to arrays of UV light sources when connected by a wired or wireless charging connection to the electronic gaming device, or to another power source.

The UV disinfection shield assembly can include one or more anchors, which are configured to attach the UV disinfection shield assembly to an anchor position on the electronic gaming device. For example, an anchor is a hook or latch shaped to attach to an anchor position (e.g., metal bar in a recessed portion of the cabinet of an electronic gaming device). Or, an anchor is a magnetic pad placed to attach to a metallic pad on the electronic gaming device.

Figure 14A:
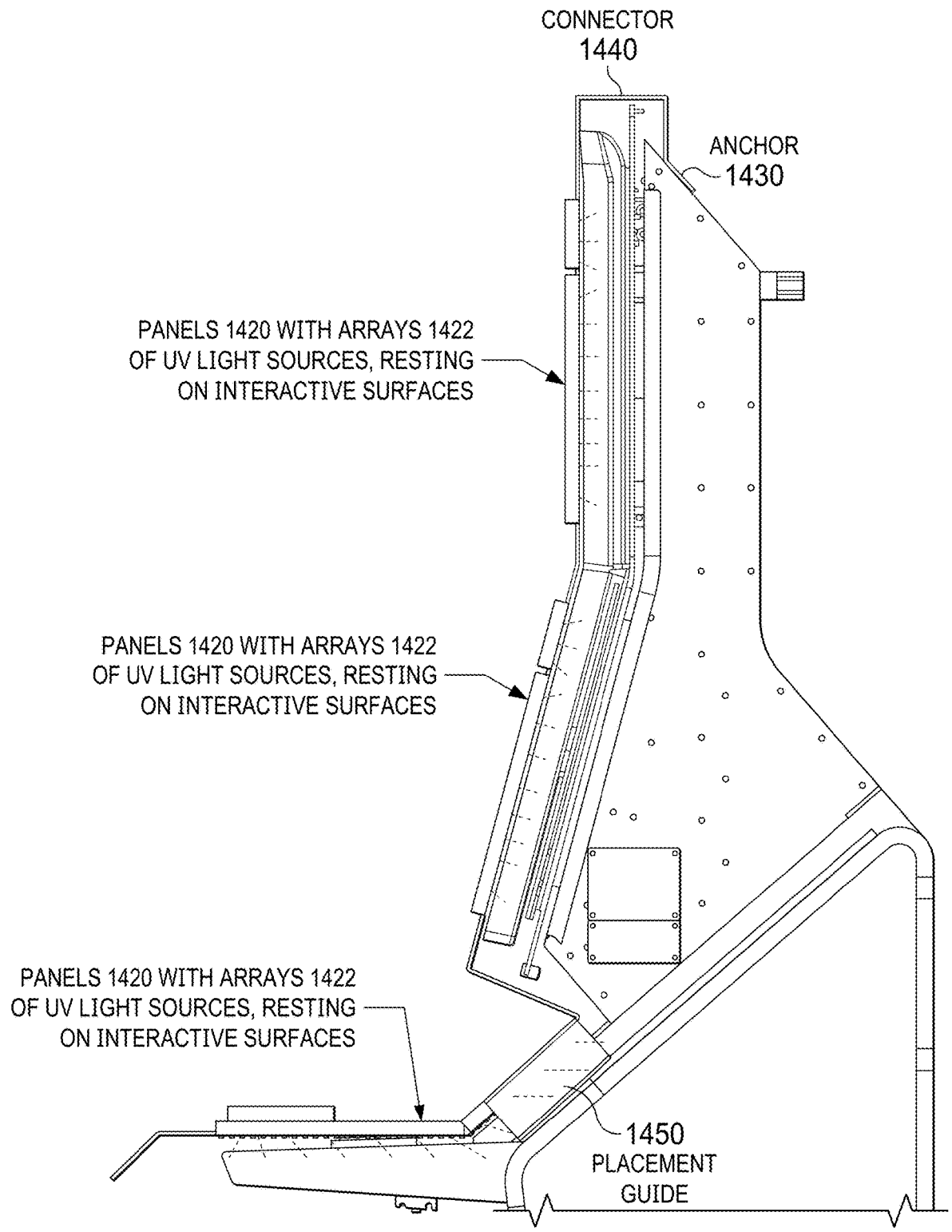
FIGS. 14A-14D illustrate features of an example UV disinfection shield assembly, including UV light sources, which is adapted to fit over an example standalone electronic gaming device.

FIGS. 14A-14D show features of an example UV disinfection shield assembly 1405, including UV light sources, which is adapted to fit over an example electronic gaming device. The UV disinfection shield assembly 1405 includes multiple panels 1420, which include arrays 1422 of UV light sources. In FIG. 14A, the panels 1420 are resting on interactive surfaces (e.g., button deck, displays) of the electronic gaming device.

Figure 14B:
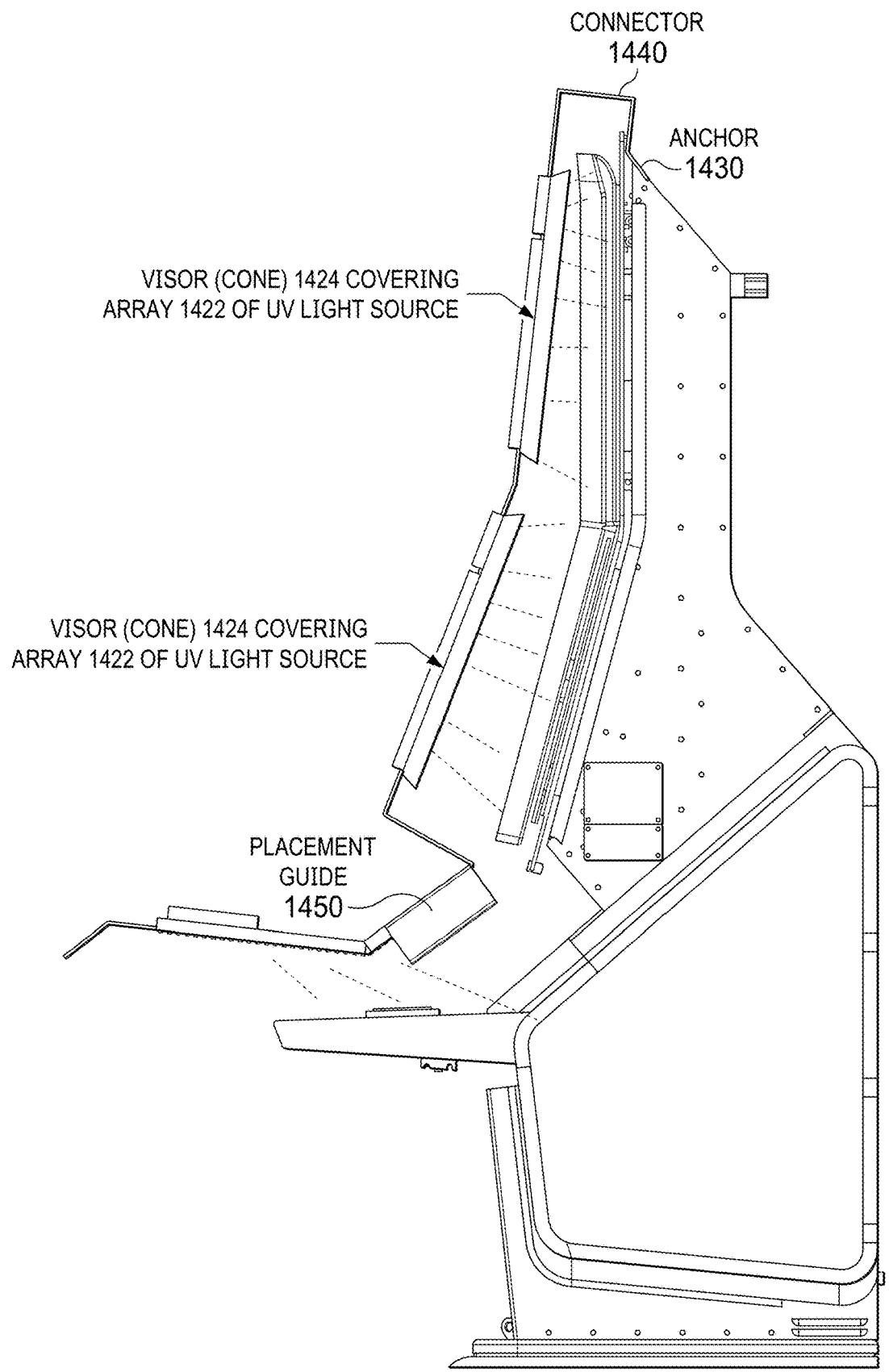
Figure 14C:
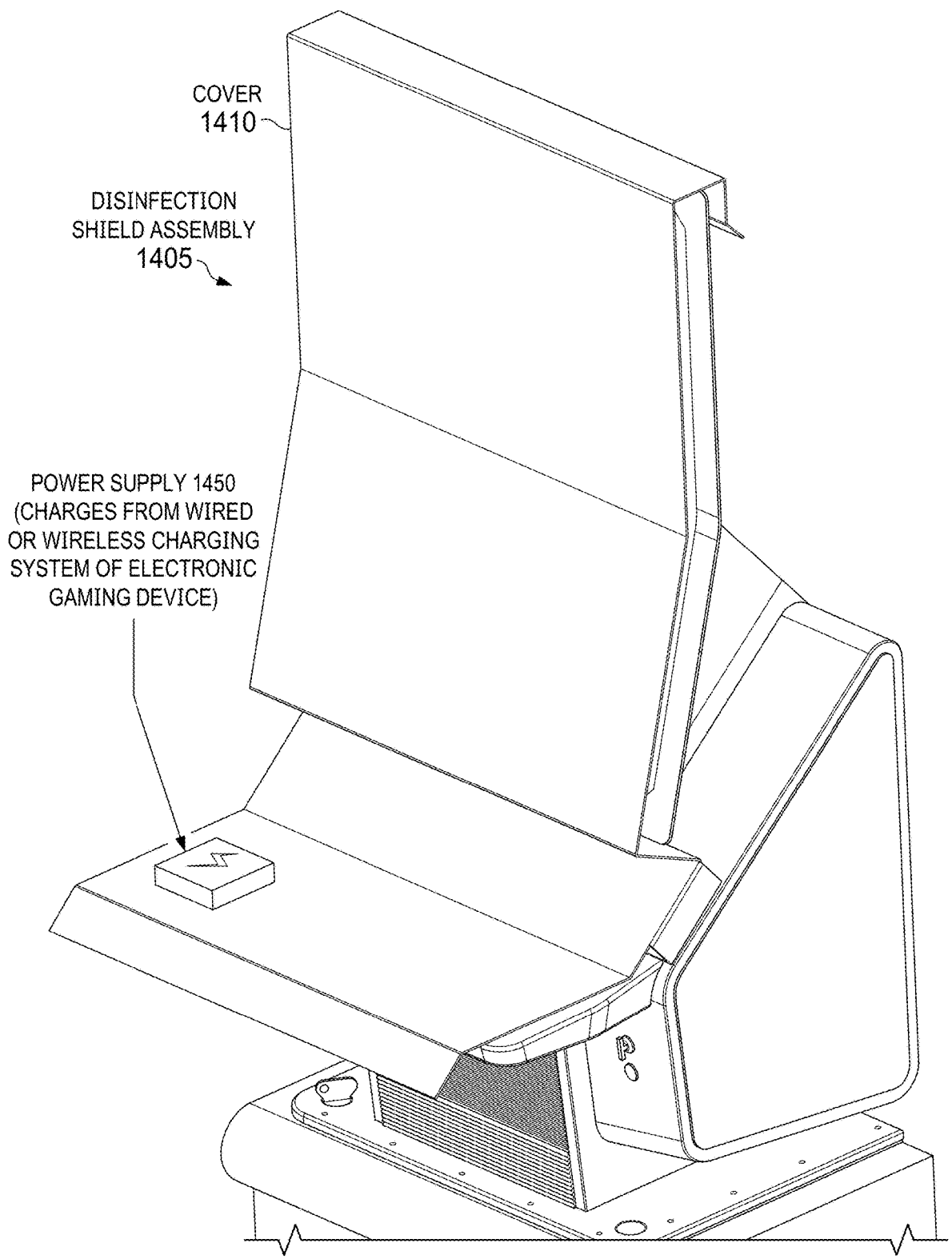
Figure 14D:
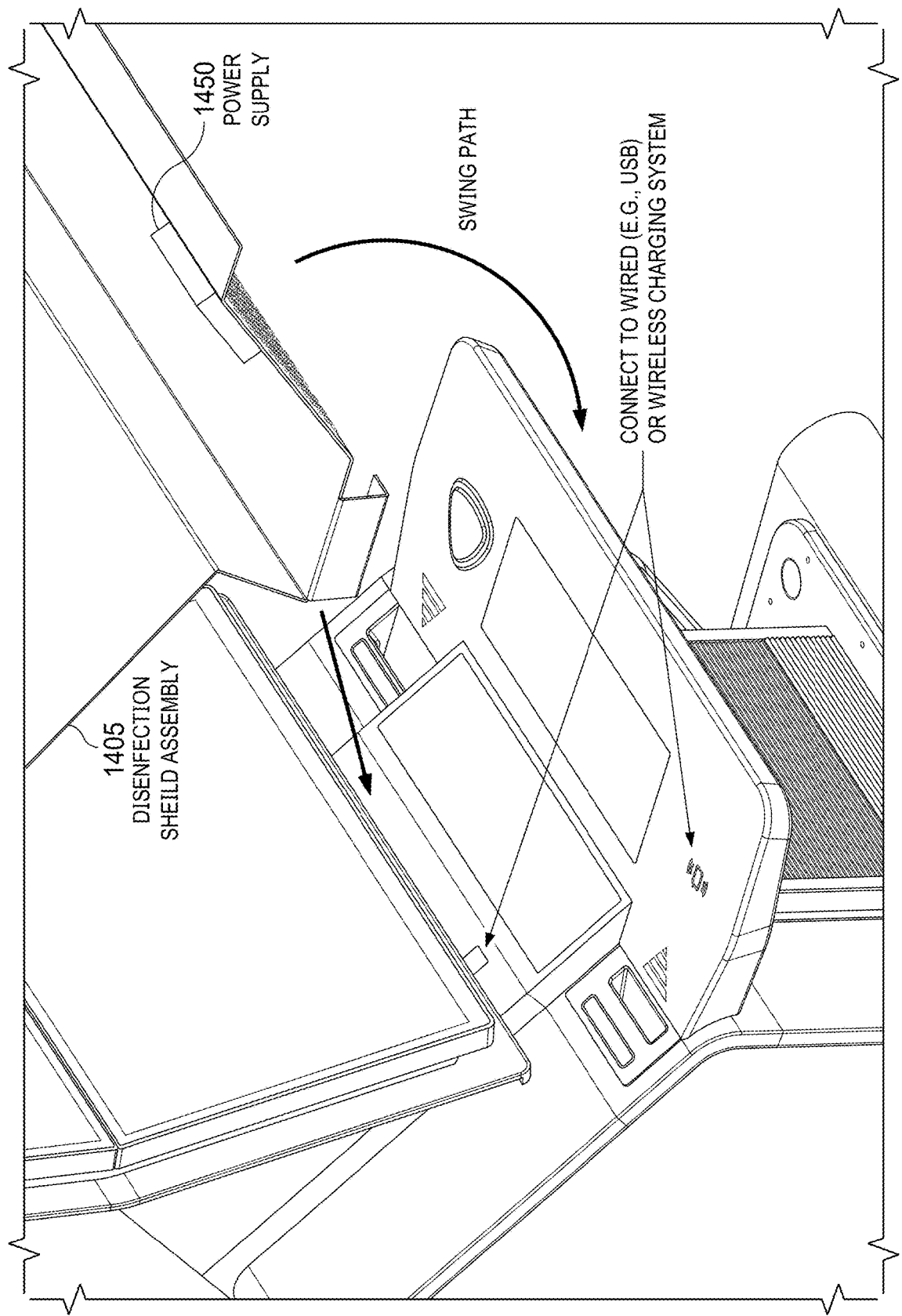

The UV disinfection shield assembly 1405 also includes an anchor 1430, which is configured to attach to an anchor position of the electronic gaming device, and a connector 1440. The connector 1440 connects the UV disinfection shield assembly 1405 to the electronic gaming device. A placement guide 1450 of the UV disinfection shield assembly 1405 assists in positioning of the UV disinfection shield assembly 1405 on the electronic gaming device. As shown in FIG. 14B, around a panel 1420, a visor (cone) 1424 can cover the array 1422 of UV light sources. The visor 1424 reflects UV light towards the electronic gaming device and helps block the UV light from escaping from underneath the panel 1420.

The UV disinfection shield assembly 1405 includes a cover 1410. The cover 1410 can be made of a flexible material such as cloth or a flexible plastic. The underside of the cover 1410 can be made of or coated with a material adapted to reflect UV light towards the electronic gaming device.

The UV disinfection shield assembly 1405 includes a power supply 1450, which is configured to supply electrical current to the UV disinfection shield assembly 1405 when connected to a wired or wireless charging system of the electronic gaming device. When attached to the electronic gaming device at the anchor position, the UV disinfection shield assembly 1405 can swing downward as panels 1420 unfold. When positioned, the power supply 1450 can connect to the charging system of the electronic gaming device.

XII. Example Chip Trays and Covers.

This section describes examples of chip trays, chip tray enclosures, and other UV disinfection enclosures with UV light sources for UV disinfection. A chip tray can include one or more integrated UV light sources. Or, a chip tray without integrated UV light source(s) can be retrofitted with UV light sources or can be selectively covered with a UV disinfection enclosure, to enable UV disinfection. UV disinfection enclosures can be adapted for different form factors of chip trays or other gaming equipment. UV light source(s) can be implemented as described in section III.

An example chip tray includes multiple sections shaped to hold gaming chips and one or more UV light sources. The UV light source(s) can be arranged along at least one edge of the apparatus so as to, when activated, emit UV light across at least part of the multiple sections. The UV light source(s) can be embedded in the chip tray along the edge(s) or otherwise attached to the chip tray.

In some example implementations, the UV light source(s) are in a UV LED strip arranged along an edge of the chip tray that is closest to a user position. The UV LED strip is arranged so as to, when activated, emit UV light away from the user position. More generally, the UV light source(s) can be arranged along one edge of the chip tray, two opposite edges of the chip tray, all but one edge of the chip tray, or all edges of the chip tray.

Figure 15:
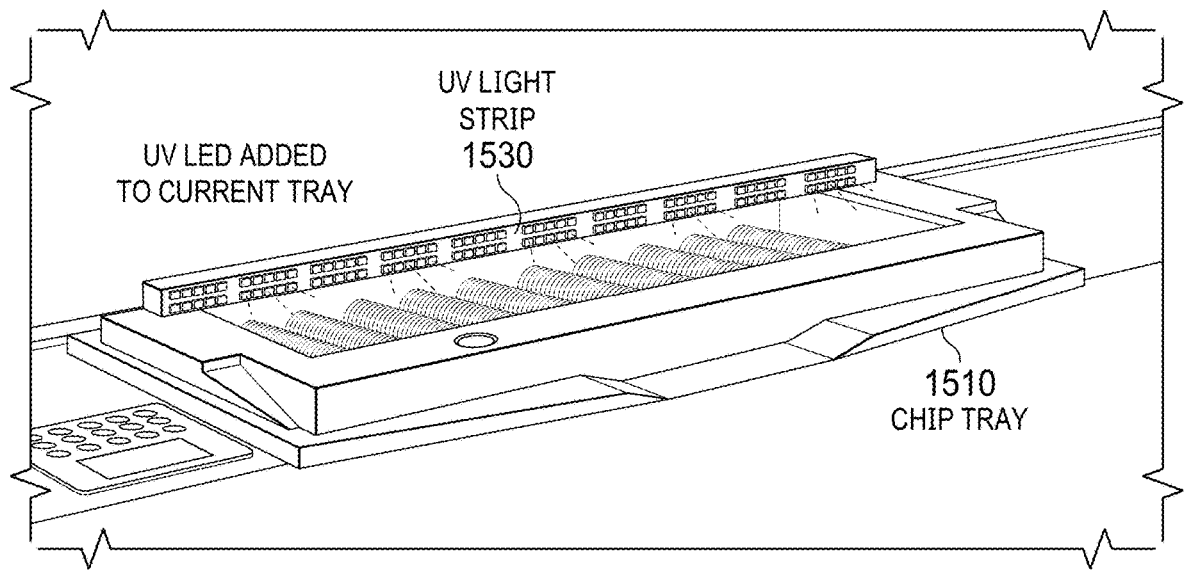
FIGS. 15 and 16 illustrate example chip trays including UV light sources.
Figure 16:
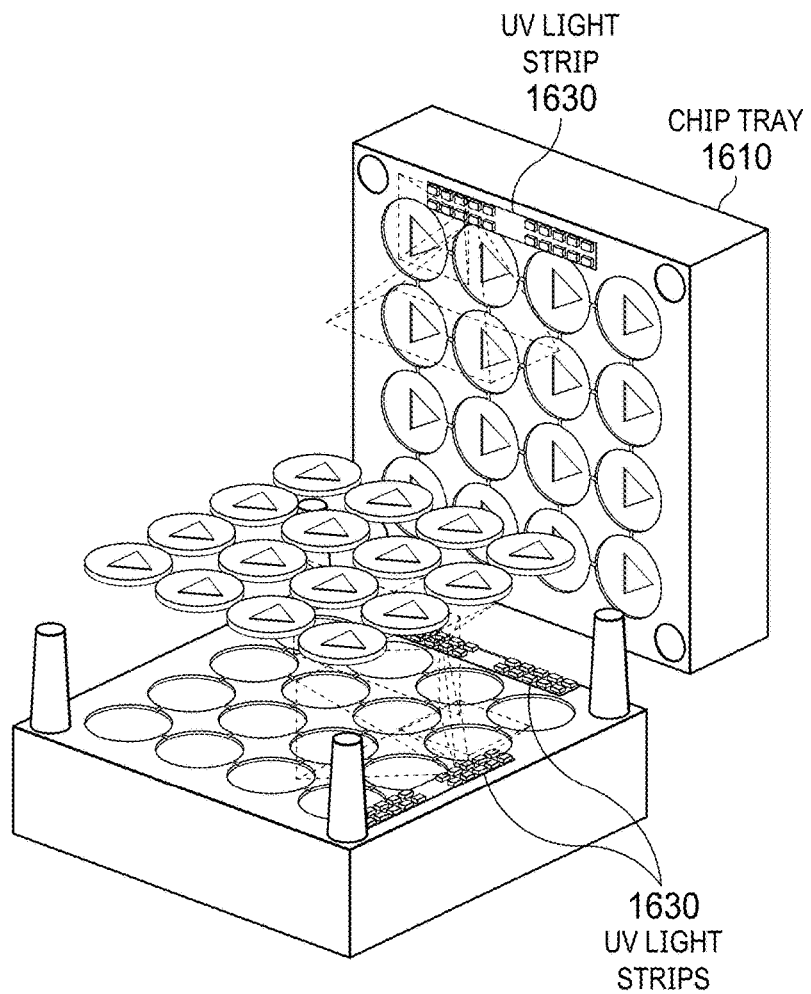

FIGS. 15 and 16 show example chip trays including UV light sources. In FIG. 15, a UV LED strip 1530 is attached to a chip tray 1510. The UV LED strip 1530 can be embedded in a recessed portion of the chip tray 1510 or otherwise affixed to the chip tray 1510. In this way, existing chip trays can be retrofitted to include UV light sources. In FIG. 16, multiple UV LED strips 1630 are attached to a chip tray 1610.

A chip tray enclosure or other UV disinfection enclosure can be placed over a chip tray, over part of an electronic gaming device (e.g., over a button deck), or over other gaming equipment for UV disinfection of surfaces exposed to UV light. UV disinfection enclosures can be contoured to fit over different form factors of chip trays, electronic gaming devices, or other gaming equipment. In this way, UV disinfection can be provided for gaming equipment that lacks integrated UV light sources.

In a chip tray, the surfaces of chips exposed to UV light can be disinfected. To increase the number of chips with surfaces exposed to UV light, spacers can be used to create gaps between chips, or a section that holds chips can be shaped to cause chips to rest with some amount of space between the chips, exposing more surfaces of the chips to UV light.

An example enclosure includes a housing and one or more UV light sources. The housing is shaped to fit over a least part of an electronic gaming device, chip tray, or other gaming equipment. The inside of the housing can be made of or coated with a material adapted to reflect UV light. The UV light source(s) are arranged inside the housing so as to, when activated, emit UV light towards the at least part of the electronic gaming device, chip tray, or other gaming equipment that is enclosed.

The housing of the UV disinfection enclosure can be a hood that is shaped to fit over at least part of an electronic gaming device, chip tray, or other gaming equipment. Or, the housing of the UV disinfection enclosure can be a panel having arranged, on one side of the panel, an array of the UV light sources, in which case the UV disinfection enclosure also includes a cover over the panel. Or, the housing can be a rigid shell with a concave recess that at least approximately follows contours of the least part of an electronic gaming device, chip tray, or other gaming equipment.

The UV disinfection enclosure can include a power supply, which is configured to supply electrical current to the UV light source(s) when connected by a wired or wireless charging connection to the gaming equipment or to another power source. The UV disinfection enclosure can include an anchor configured to attach the UV disinfection enclosure to an anchor position on the electronic gaming device, chip tray, or other gaming equipment.

XIII. Example Techniques for UV Disinfection.

This section describes various examples techniques for UV disinfection. The example techniques can be performed by an electronic gaming device (as described above), a system server, a chip tray (as described above), or other gaming equipment configured to perform operations for the respective techniques.

FIG. 17 shows an example technique (1700) for managing UV disinfection of an electronic gaming device, chip tray, or other gaming equipment, including automatic activation and deactivation of UV light source(s).

To start (stage 1710), an activation condition is detected. For example, the activation condition is: (1) inactivity of a user, as indicated by expiration of an activity timer, (2) empty space in a threshold region around the electronic gaming device, chip tray, or other gaming equipment, as indicated by feedback from a camera, (3) actuation of a button on the electronic gaming device, chip tray, or other gaming equipment, (4) a defined start time for a UV disinfection cycle, (5) a UV-disinfection-start prompt, from a system server, for a UV disinfection cycle, (6) closing of a lid or cover, (7) detection of a warning condition for a user, (8) detection of a pathogen, and/or (9) some other condition.

At stage 1720, a UV disinfection mode is selected from among multiple available UV disinfection modes. Example UV disinfection modes are described in section VIII. The UV disinfection mode can be selected based at least in part on the activation condition and/or based on other criteria. In alternative implementations, stage 1720 is omitted, and a single UV disinfection mode is used.

At stage 1730, based at least in part on the detected activation condition, one or more UV light sources are activated. The UV light source(s) are arranged so as to emit UV light across at least part of the electronic gaming device or chip tray. At stage 1740, after completion of the UV disinfection, the UV light source(s) are deactivated.

At stage 1750, a message is sent that indicates status of UV disinfection of the electronic gaming device, chip tray, or other gaming equipment. The message can be sent to an administrative service, a user account, a cleaning staff account, and/or another recipient. For example, the status of UV disinfection is that a UV disinfection cycle has been completed for the electronic gaming device, chip tray, or other gaming equipment. Alternatively, stage 1750 can be omitted.

At different times during the technique 1700, a screen can be rendered on a display that indicates the status of UV disinfection of the electronic gaming device, chip tray, or other gaming equipment. FIG. 17 shows examples of status information that can be displayed. For example, before the activation condition is detected, a screen can show that a UV disinfection cycle is ready to start (e.g., "Start UV disinfection?" or "# hours since last UV disinfection"). After the activation condition is detected, a screen can show that a disinfection cycle has started for the electronic gaming device, chip tray, or other gaming equipment (e.g., "Starting UV disinfection"). Alternatively, if UV light source(s) are not automatically activated and deactivated, the screen can show that a manual disinfection cycle has been requested for the electronic gaming device, chip tray, or other gaming equipment. After a UV disinfection mode has been selected, a screen can show the selected mode (e.g., "UV disinfection mode X selected"). During UV disinfection, a screen can show the time remaining (e.g., "UV disinfection in process—4:59 remaining" . . . "UV disinfection in process—0:01 remaining") or otherwise show progress (e.g., with a bar graphic showing percentage towards completion). After the UV disinfection has completed, a screen can show that a disinfection cycle has completed for the electronic gaming device, chip tray, or other gaming equipment (e.g., "UV disinfection completed").

Alternatively, an electronic gaming device (as described above), a system server, a chip tray (as described above), or other gaming equipment can be configured to manage UV disinfection by controlling one or more screens that indicate status of UV disinfection. To start, an activation condition is detected (e.g., one of the activation conditions described above). Based at least in part on the detected activation condition, a screen is rendered that indicates the status of UV disinfection of the electronic gaming device, chip tray, or other gaming equipment. For example, the status of UV disinfection is that a UV disinfection cycle has started (in which case UV light source(s) can be activated) or that a UV disinfection cycle has been requested (in which case a message can be sent, indicating the status of UV disinfection to an administrative service, a cleaning staff account, etc.).

Alternatively, an electronic gaming device (as described above), a system server, a chip tray (as described above), or other gaming equipment can be configured to manage UV disinfection by sending messages that indicate status of UV disinfection. To start, an activation condition is detected (e.g., one of the activation conditions described above). Based at least in part on the detected activation condition, a message is sent that indicates status of UV disinfection of the electronic gaming device, chip tray, or other gaming equipment (e.g., that a UV disinfection cycle has started, has been requested, or has completed). The message can be sent to an administrative service, a cleaning staff account, and/or another recipient. If the activation condition relates to a warning condition for a user, the message can request that staff check on the user (e.g., to offer assistance).

XIV. Example External Cleaning Systems

Figure 18A:
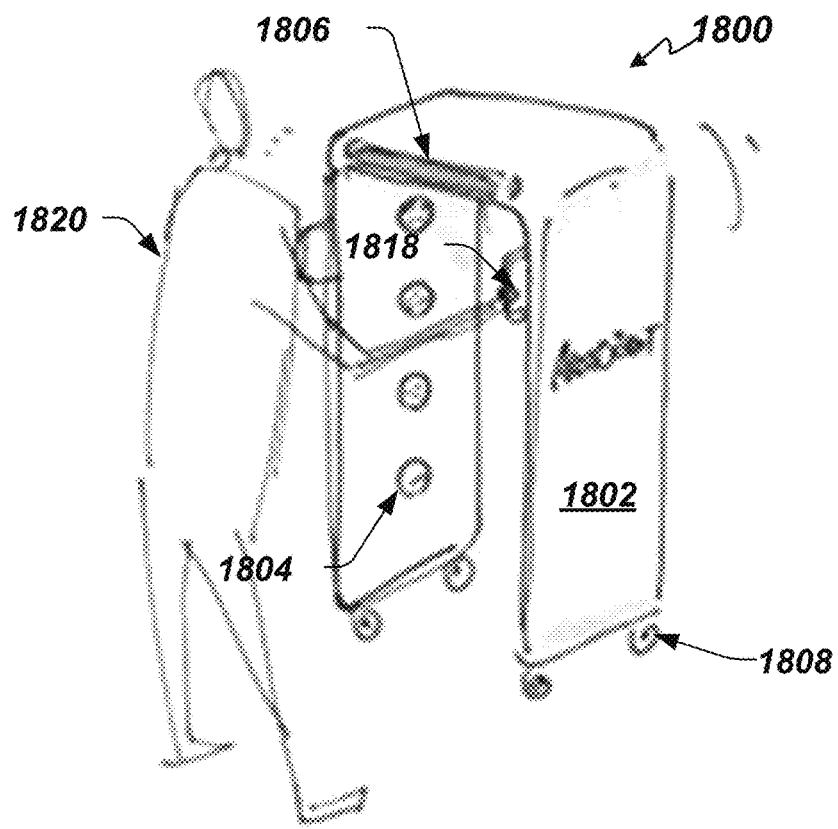
FIGS. 18A-18F are exemplary systems for external cleaning of a gaming environment according to some aspects of the present disclosure.

FIGS. 18A-18F illustrate exemplary systems for external cleaning of a gaming environment according to some aspects of the present disclosure. As shown in the example of FIG. 18A, a mobile sanitization system 1800 includes one or more sanitization accessories 1804. The one or more sanitization accessories 1804 are secured to a housing 1802, such as by removable fastener, adhesive, welding, or other techniques. One or more user interfaces 1806 may be included, to receive inputs from the operator 1820 and/or to provide information to the operator 1820. For instance, the user interface 1806 may accept commands (e.g., to activate or end a cleaning operation) and/or provide an indication of system operations (e.g., cleaning status, disinfectant level, energy storage level, etc.).

One or more wheels and/or casters 1808 may support the housing 1802 such that an operator 1820 may freely move the system 1800, such as by one or more handles or grips 1818. In some examples, the system 1800 includes a drive system to turn the wheels to move the system 1800, either by direction of an operator 1820 (e.g., by a user interface providing input to control circuitry of the system 1800), by remote control (e.g., via a networked remote control system), and/or by application of one or more artificial intelligence programs.

Figure 18B:
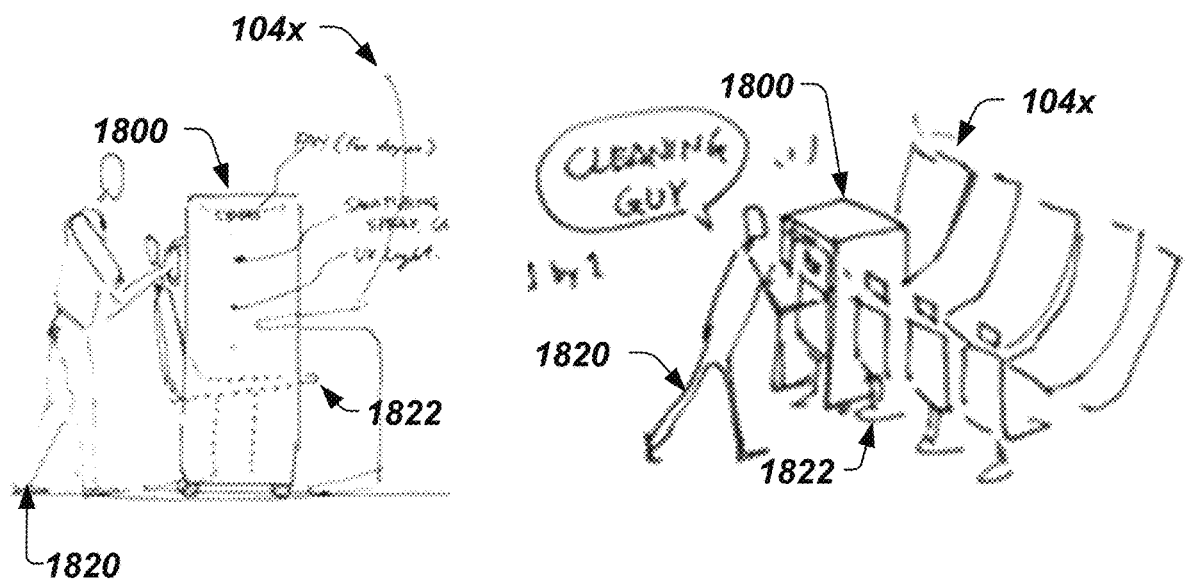
Figure 18C:
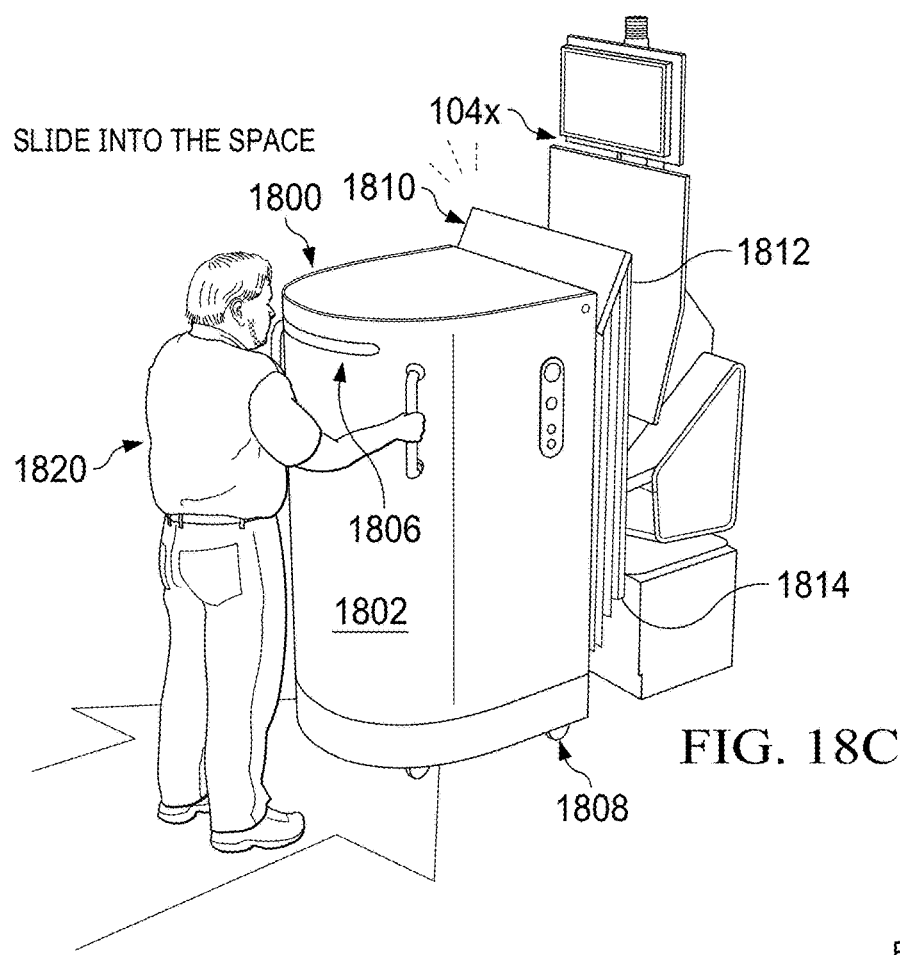

During a sanitization operation, as shown in FIGS. 18B and 18C, the system 1800 can be wheeled or otherwise moved to a gaming environment, for example one or more EGMs 104x and/or one or more seats 1822. As shown, the system 1800 is configured to at least partially enclose one or more components of the EGM 104x, such as the EGM cabinet, an associated display, a button deck or play surface, or a seat 1822, as several non-limiting examples. During the sanitization operation, the arrangement of the sanitization accessories 1804 directs the output toward the one or more components. For example, the one or more sanitization accessories 1804 can include a liquid application tool (e.g., to discharge a disinfecting liquid such as ozone mist), a UV light source, and/or an electrostatic tool.

In some examples, the sanitization accessories 1804 can hold various positions or orientations depending on the gaming environment and/or the type of accessory. In some examples, the position or orientation can be changed manually or by a motor or other actuator. For instance, a sanitization accessory in a first orientation can sanitize a first component (e.g., the display) and sanitize a second component (e.g., a button deck) in a second orientation. Each sanitization accessory 1804 can be activated and/or oriented independently of another sanitization accessory.

For autonomous operation, the system 1800 may include one or more sensors (e.g., infrared (IR) sensors, acoustic sensors, vision sensors, tactile sensors, radar, Light Detection and Ranging (LIDAR) sensors) configured to identify objects and inform the control circuitry to avoid and/or focus on an object for sanitization.

In some examples, the system 1800 can be configured to move in a direction along the line of the bank of chairs, as opposed to moving the system 1800 to insert the seat 1822 and/or EGM 140x into the housing 1802. Thus, the interior of the housing 1802 may be shaped to conform to the contours of the gaming environment to be cleaned. Further, one or more curtains, shields, or other type of protective cover can be employed to limit dispersion of liquid and/or UV light during a sanitization operation. In other embodiments, the system 1800 may be deployed from a ceiling location above the EGMs and lowered in place for to conduct the sanitizing operation. In yet other embodiments, the system 1800 may be deployed from a chamber area below the floor supporting the EGMs to conduct the sanitizing operation. Also, the system 1800 may be controlled at remote office location.

Figure 18D:
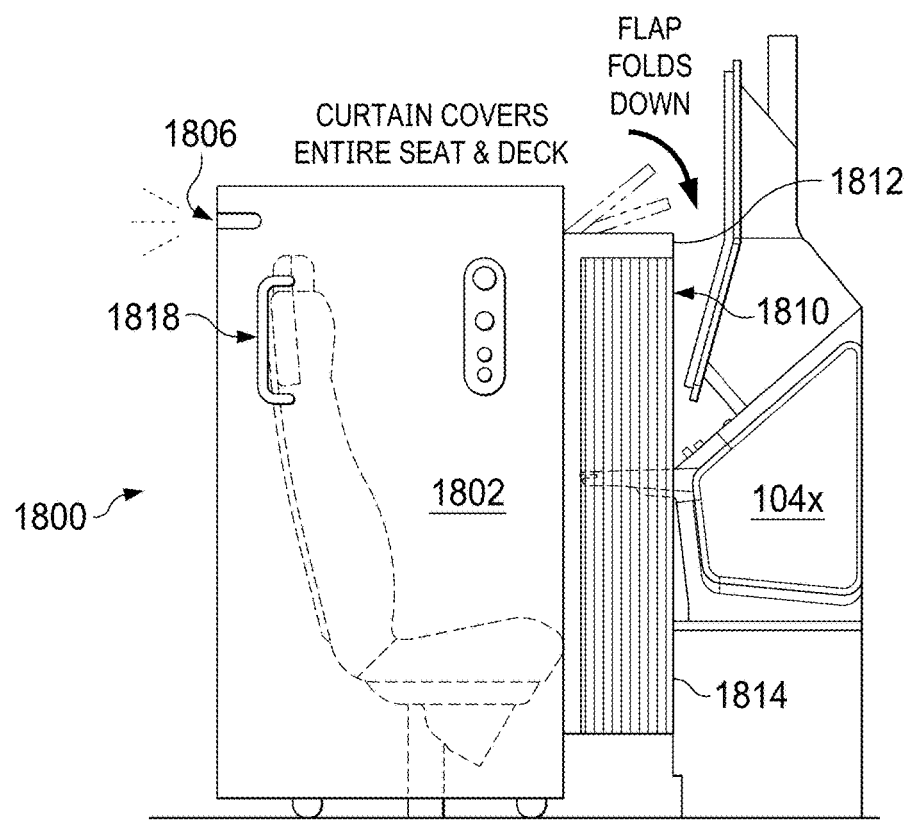

FIGS. 18C and 18D illustrate another example system 1800. As shown, a portion of the system 1800 provides a single opening to the interior of the housing 1802 for enveloping the EGM 104x and/or seat 1822 to be cleaned. At the opening of the housing 1802 is an extension attachment 1810 configured to extend from an end of the housing 1802 facing the gaming environment and at least partially cover one or more components. The system 1800 may include onboard power sources to operate.

The extension attachment 1810 provides a protective cover to at least partially prevent disinfectant and/or UV light from escaping the gaming environment during a cleansing or sanitizing operation. For example, a lid or flap 1812 can be activated to pivot downward or extend from within the housing 1802 (e g, manually and/or by activating one or more actuators), which causes one or more shields 1814 of the extension attachment 1810 to extend from the housing to form the protective cover.

Figure 18E:
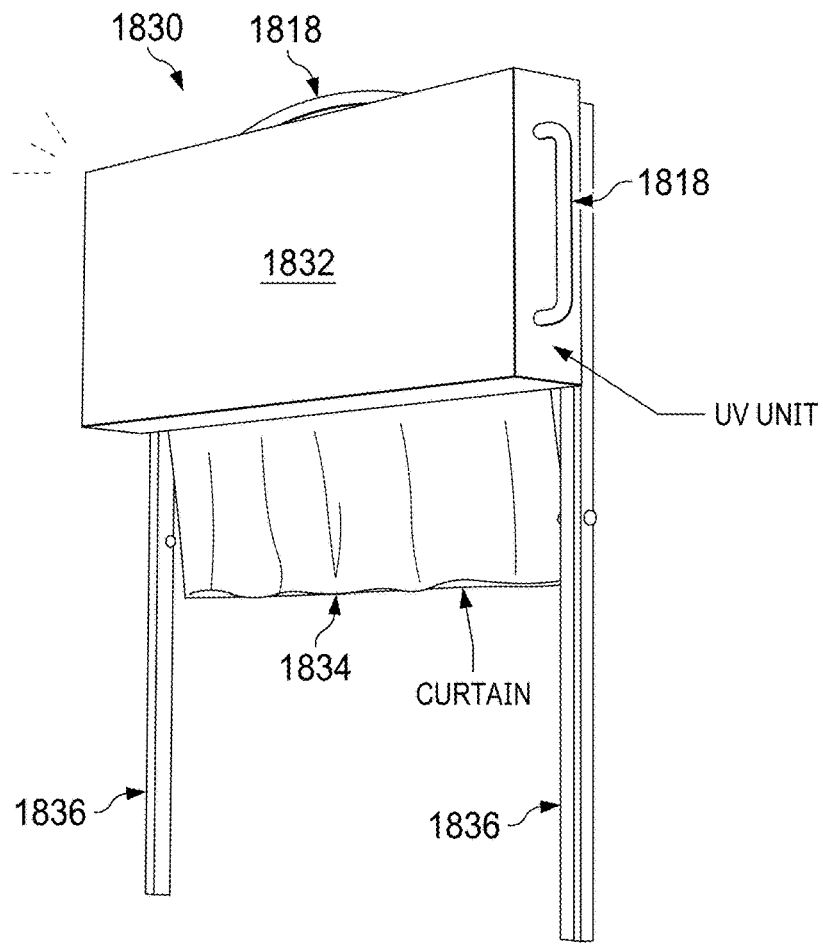
Figure 18F:
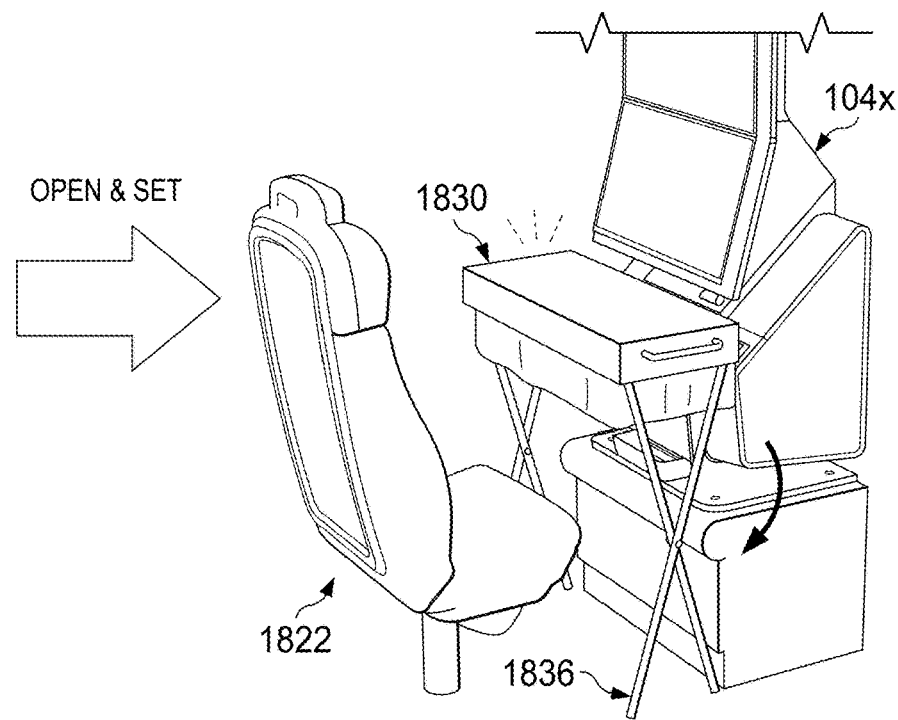

FIGS. 18E and 18F illustrate another example mobile sanitization system 1830. The system 1830 includes a frame 1836 configured to support a housing 1832 of the system 1830 during a sanitization operation. For example, the frame 1836 is configured to deploy from a storage mode, shown in FIG. 18E, to an operational mode, shown in FIG. 18F, in response to a user command A curtain or shield 1834 is secured to a frame of the housing 1832 to provide a cover during a sanitization operation to ensure disinfectant and/or UV light does not escape the gaming environment during a cleansing or sanitizing operation.

XV. Example No-Contact Systems

Figure 19:
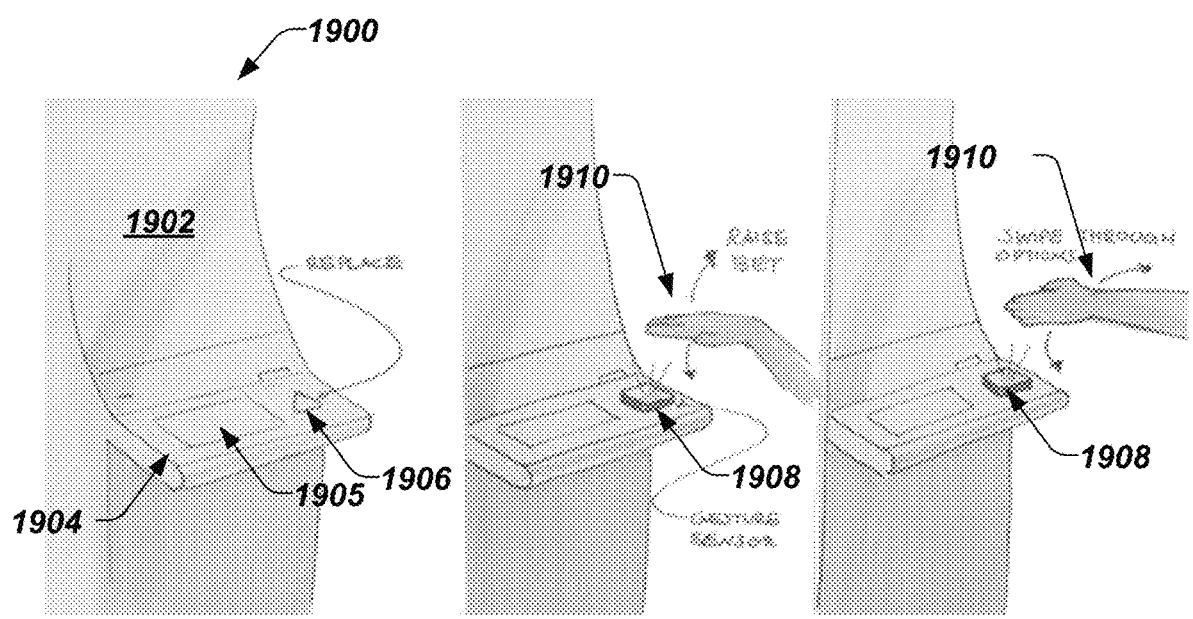
FIG. 19 is an exemplary system for non-contact control of an electronic gaming device according to some aspects of the present disclosure.

FIG. 19 shows an exemplary system for non-contact control of an EGM or other electronic gaming device according to some aspects of the present disclosure. As shown, an exemplary EGM 1900 includes a display 1902, a surface 1904 which includes a keyboard and/or button panel 1905, and/or a control interface 1906. In some examples, the control interface 1906 is configured to receive commands from a player 1910 by making contact with the interface.

A non-contact or contactless user interface 1908 can be included with the EGM 1900 to allow the player 1910 to avoid interacting with the EGM 1900 by contact. In some examples, the interface 1906 can be removed and replaced with the contactless interface 1908. For instance, one or more wires or other contacts used to connect the interface 1906 can be reworked to install the contactless interface 1908.

The contactless interface 1908 may include one or more sensors (e.g., IR sensors, acoustic sensors, vision sensors, radar, LIDAR sensors) configured to measure one or more gesture inputs from the player 1910. The contactless interface 1908 and/or the sensors may be connected to a control circuitry to control operation of the EGM 1900 by the one or more gesture inputs. For example, the control circuitry receives sensor data corresponding to the one or more gesture inputs, compares the sensor data to a list associating sensor data to gesture commands, and determines a gesture command based on the comparison.

In some examples, the contactless interface 1908 can include a wireless communication circuit (e.g., transceiver, network interface, etc.) to at least partially communicate sensor data with the control circuitry via one or more wireless protocols (e.g., wireless fidelity, BLUETOOTH, etc.). In some examples, a mobile device such as a player's smartphone, can be wirelessly connected with the EGM 1900. The mobile device may use a mobile application to present a user interface through which commands can be inputted and then transmitted to the control circuitry to provide contactless control of the EGM 1900.

In additional or alternative examples, the contactless interface is configured to project light onto a surface (e.g., a fixed or moveable surface) to replicate one or more user interfaces (e.g., a keyboard, button, etc.). The player 1910 may interact with the replicated user interface, the resulting gestures being captured by one or more cameras. The captured data would then be transmitted to the control circuitry to analyze and determine which command corresponds to a particular captured gesture. In some examples, the light is projected onto a moveable surface that need not be shared between players (e.g., a tablet, a tray). In some examples, the surface is the player's knee, lap, etc., such that the player need not contact any surface during gameplay. The projected light could originate from the underside of the button deck, above the EGM or other location that would still facilitate contactless play of the EGM.

Figure 20:
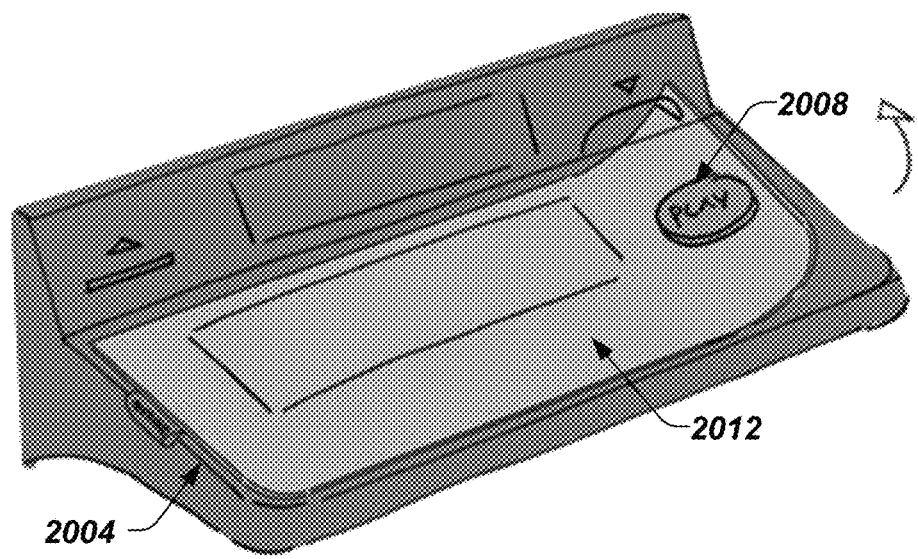
FIG. 20 is an exemplary system for protecting one or more surfaces of an electronic gaming device according to some aspects of the present disclosure.

FIG. 20 shows an exemplary system for protecting one or more surfaces of an EGM according to some aspects of the present disclosure. A protective cover 2012 is configured to follow contours of one or more physical user interfaces of an electronic gaming device. For example, the protective cover 2012 may be formed to be removably secured to one or more surfaces 2004 of the one or more physical user interfaces 2008 (e.g., a button deck, a button housing). However, in some examples the button deck includes one or more touchscreen buttons which may be manipulated through the protective cover 2012.

In some examples, the protective cover or sheet 2012 is made of a material with a composition (e.g., copper, silver, silicon) engineered to reject and/or destroy particles (e.g., germs, viruses, etc.). Additionally or alternatively, the protective cover or sheet 2012 may be treated with a disinfectant prior to, during use and/or after use. The protective cover sheet 2012 could deployed from cylindrical rolls and could be deployed in combination with UV light. A location within the EGM could house the detachable protective cover or sheet 2012.

Once positioned, the protective cover or sheet 2012 may be repositionable or disinfected after use and re-used. In other embodiments, a roller or blade may pass over the plastic cover or sheet 2012 to clean the protective cover or sheet 2012 prior to, during and/or after use.

Various fastening devices may detachably secure the protective cover or sheet 2012 to the EGM. In some examples, the protective cover or sheet 2012 may be secured to the surface by one or more techniques and/or methods, including close-fitting contours, electrostatic adhesion, fasteners, as a number of non-limiting examples. Further, adhesives may be used to secure the protective sheet in place, which may also contain disinfectants.

In some examples, the material is transparent or semi-transparent in the visual spectrum to allow a player to view indications (e.g., text, characters, light, etc.) of buttons below the sheet.

Figure 21:
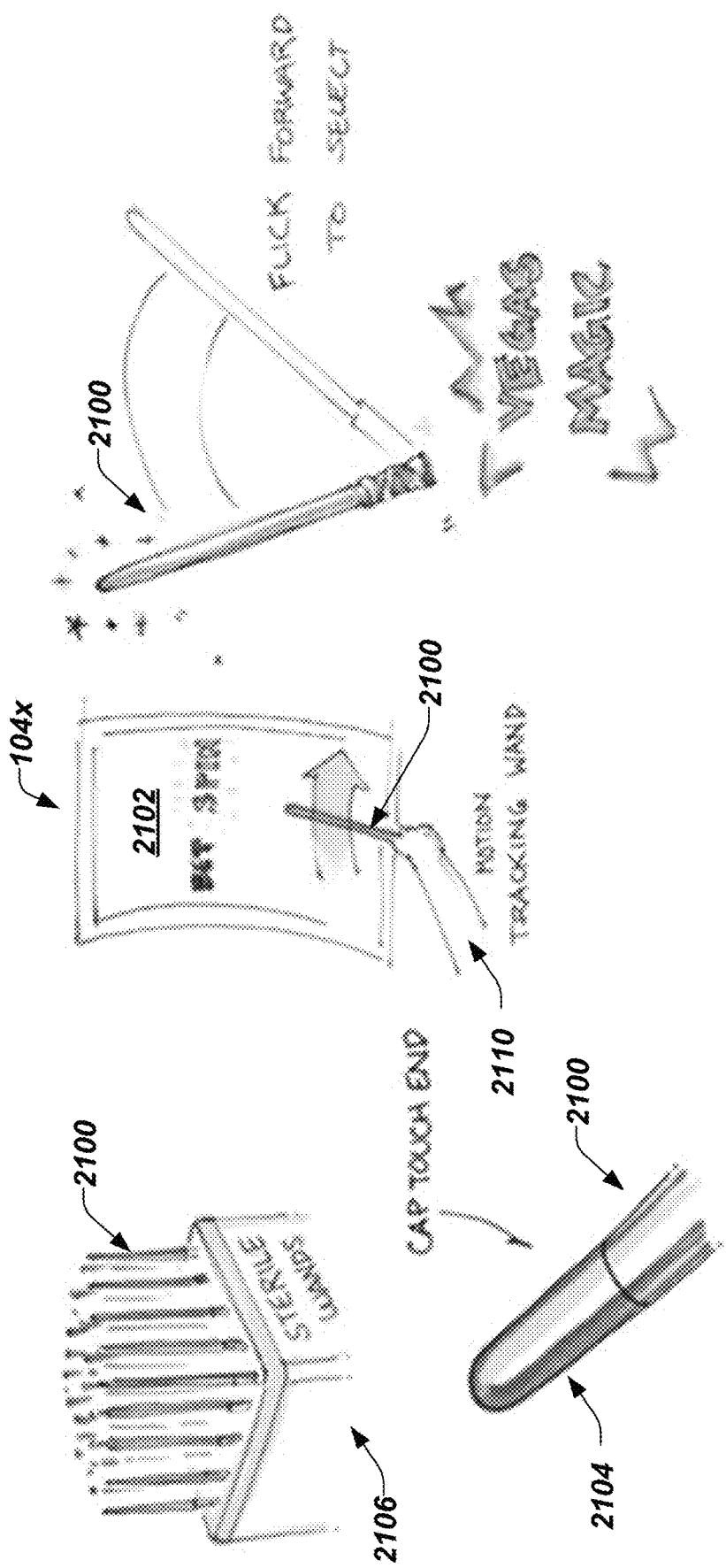
FIG. 21 is an exemplary system or device for control of an electronic gaming device according to some aspects of the present disclosure.

FIG. 21 shows an exemplary system or device (e.g., stylus) 2100 for control of an EGM 104x or other electronic gaming device according to some aspects of the present disclosure. For example, the system includes a stylus or device 2100 configured to provide commands via one or more of a contact input or a contactless input from a player 2110. For example, a user interface includes one or more sensors (e.g., IR sensors, acoustic sensors, vision sensors, radar, contact sensors, capacitive touch sensors, LIDAR sensors, magnetic sensors, etc.) to receive the inputs from a user 2110. The user interface may be presented as a dedicated device (such as contact sensor 2106, contactless sensor 2108, a sensor embedded in the EGM 104x cabinet or display 2102, etc.). Sensor data from the one or more sensors corresponding to the inputs is transmitted to the control circuitry (e.g., via one or more transceivers or wireless network interfaces). At the control circuitry, the sensor data is compared to a list associating sensor data to a plurality of commands to determine a desired command of the plurality of commands based on the comparison.

In some examples, the stylus comprises an active stylus portion 2104 to provide increased sensitivity during the contact input between the stylus and a contact enabled sensor of the one or more sensors. For example, the active stylus portion 2104 may transmit a signal, generate a magnetic field, have an electrical charge, or other characteristic which can be recognized by the EGM.

For use, the stylus 2100 may be provided in bulk such that each has the same functionality, can be drawn from a bulk package 2106, and may be disposable. The bulk package 2106 may be configured to provide sterilization of each stylus 2100 housed in the bulk package 2106, which may allow reuse of the stylus 2100.

The stylus 2100 may also include circuitry which includes a stylus identification code, such that the EGM can identify a particular stylus, and/or user identification circuitry which includes a user identification code, such that the player is identified. In some examples, the stylus 2100 is paired with a particular EGM and/or a particular player 2110.

Figure 22:
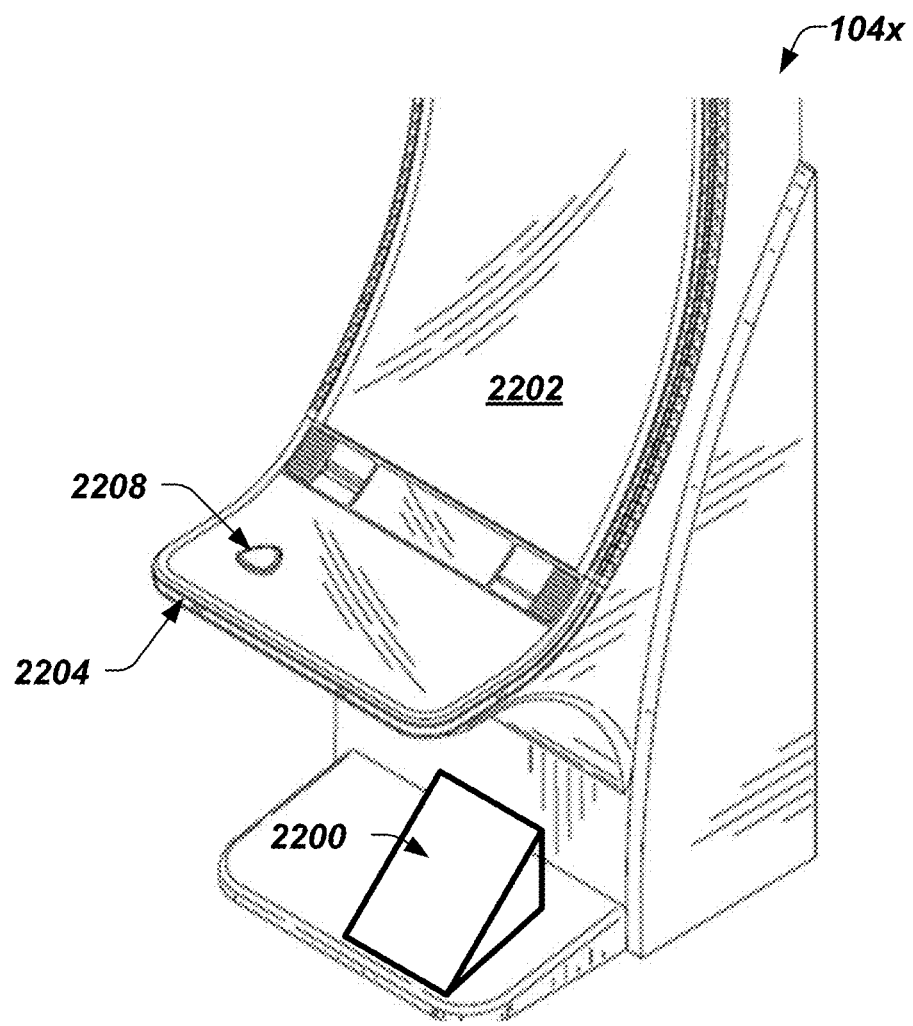
FIG. 22 is an exemplary foot-activated system for control of an electronic gaming device according to some aspects of the present disclosure.

FIG. 22 shows an exemplary foot-activated system for control of an EGM or other electronic gaming device according to some aspects of the present disclosure. In the example of FIG. 22, EGM 104x includes a foot-activated user interface 2200 and a surface 2204, which includes a keyboard and/or button panel 2208. The foot-activated user interface 2200 includes one or more sensors (e.g., contact, light activated, magnetic, accelerometer, etc.) to measure one or more gesture inputs from a user's foot. Sensor data corresponding to the one or more gesture inputs is transmitted to control circuitry, which compares the sensor data to a list associating sensor data to gesture commands, in order to determine a gesture command based on the comparison.

Although illustrated as a single interface 2200, two or more such foot-activated user interfaces may be used. The placement of each interface may correspond to different commands, or may be used in concert to generate various commands, for example. Likewise, the EGM 104x could be configured to be responsive to the accelerometer or utilizing a portable device (e.g., a mobile phone) that would allow the player to validate, synchronize, and operate the game. In this way, the player is enabled to bring his/her own button to operate the game machine in a manner not requiring contact with the EGM 104x.

XVI. Example System with Sanitizing Enclosure

Figure 23:
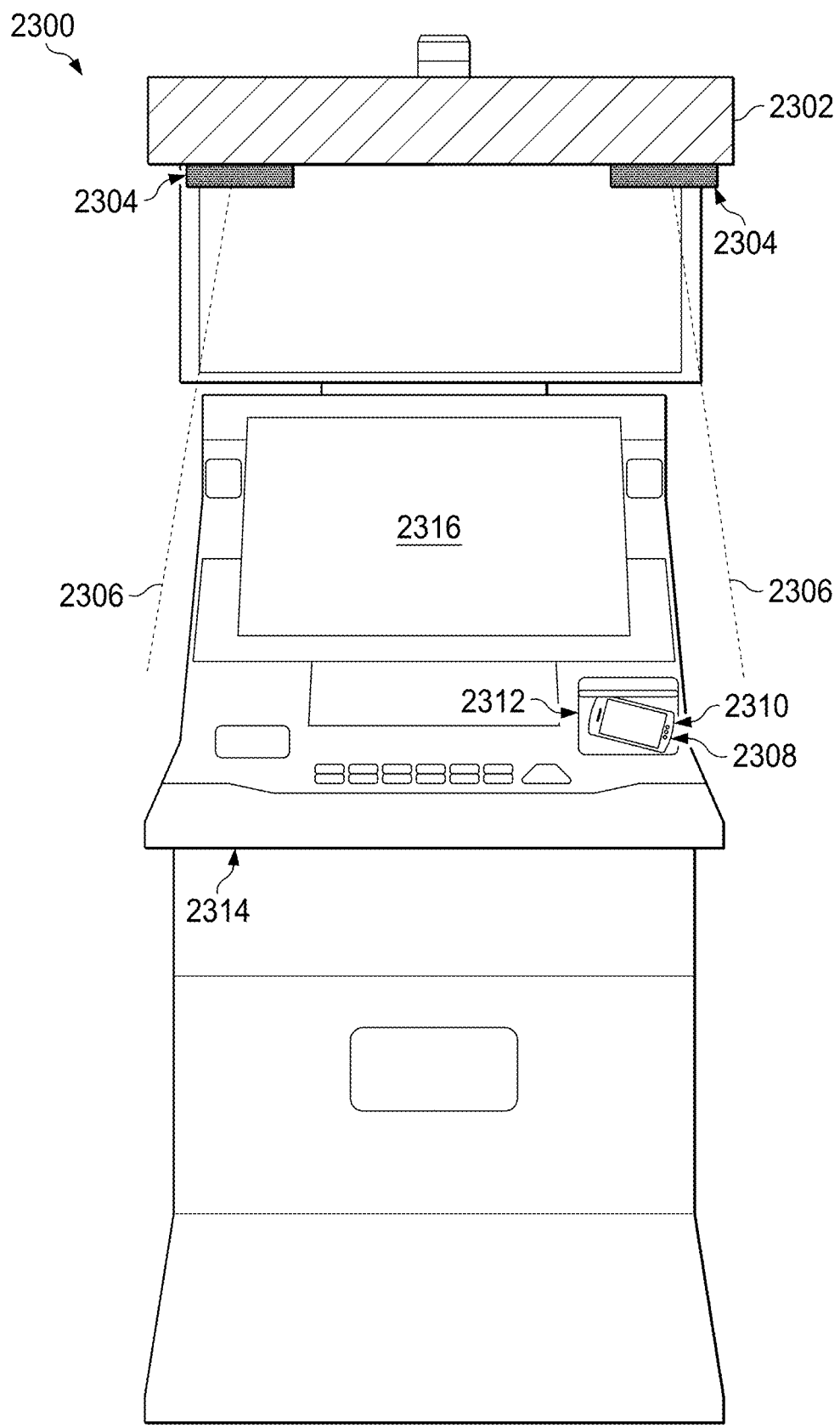
FIG. 23 is an exemplary system for sanitization of one or more gaming surfaces and/or devices according to some aspects of the present disclosure.

FIG. 23 shows an exemplary EGM system 2300 with a system 2302 for cleansing or sanitization of one or more gaming surfaces and/or devices according to some aspects of the present disclosure. The illustrated cleansing or sanitization system 2302 provides a sanitization platform with one or more UV light sources 2304 for cleansing or sanitizing one or more personal effects of the player (e.g., a mobile phone 2312) and/or one or more components of the EGM 2300 (e.g., a button deck 2314, a display 2316, etc.). For example, the one or more UV light sources 2304 are arranged at a top or upper portion of the EGM 2300 (e.g., above the main display 2316), one or more one or more UV light sources are arranged in proximity to the button panel, and/or one or more UV light sources are arranged to provide sanitizing UV light 2306 to a Slot Machine Interface Board (SMIB).

In some examples, the one or more UV light sources 2304 are embedded or otherwise integrated with a housing or other fixed structure associated with the EGM 2300. In some examples, the one or more UV light sources 2304 are provided as separate devices and/or enclosures (e.g., a sanitization platform), which may be configured to automatically change position relative to the one or more components of the EGM 2300 to perform a cleansing or sanitizing operation (e.g., move or rotate to expose the one or more UV light sources to the components). In some examples, a single UV light source 2304 may be configured to move multiple times during an operation to clean or sanitize multiple components or surfaces of the EGM 2300. In some examples, the sanitization platform system 2302 is removably secured to the EGM 2300.

In some examples, the cleansing or sanitizing operation is automatically initiated in response to a sensor input (e.g., a player leaves the gaming environment), a timer (e.g., at closing time), or based on a user input (e.g., a player or staff member can provide a contact or contactless input to initiate the cleansing or sanitizing operation).

Additionally or alternatively, an enclosure 2308 may be attached to or otherwise associated with the EGM 2300 to provide individualized cleansing or sanitization. For example, a door or cover 2310 of the enclosure 2308 can be opened (e.g., via a contact or contactless input) for deposit of one or more objects (e.g., a mobile phone 2312, a playing card, chips, keys, etc.) Once the objects are in place, a second input (e.g., closing and sealing the enclosure, selecting a virtual or physical start button) activates a cleansing or sanitizing operation, which may employ one or more UV light sources, a liquid sanitizer, or an electrostatic process, as examples of non-limiting possibilities.

XVII. Example Partitions.

This section describes examples of partitions configured for placement between electronic gaming devices. A partition includes one or more UV light sources, which are arranged so as to, when activated, emit UV light towards at least part of the electronic gaming devices. Electronic gaming devices without integrated UV light source(s) can be retrofitted with partitions to enable UV disinfection.

An example apparatus includes a pane or other partition and one or more UV light sources. The partition is shaped to fit between two or more electronic gaming devices in a bank of electronic gaming devices. The UV light source(s) are arranged along the partition so as to, when activated, emit UV light towards at least part of the electronic gaming devices separated by the partition.

The partition can be made of Plexiglas, glass, or another material. The shape of the partition depends on implementation. Generally, the partition is contoured to rest between electronic gaming devices. The partition can include brackets for attachment to the electronic gaming devices. Or, the electronic gaming devices can include brackets to secure the partition.

In some example implementations, the partition is a single pane shaped to fit between a pair of the electronic gaming devices. Alternatively, the partition consists of n panes joined at a central rigid element, with the n panes being shaped to fit between n electronic gaming devices among the electronic gaming devices. For example, n is 3 or 4, with the panes connecting at the central rigid element.

The apparatus can further include a power supply configured to supply electrical current to the UV light source(s) when connected by a wired or wireless charging connection to one of the electronic gaming devices, or to another power source.

Figure 24C:
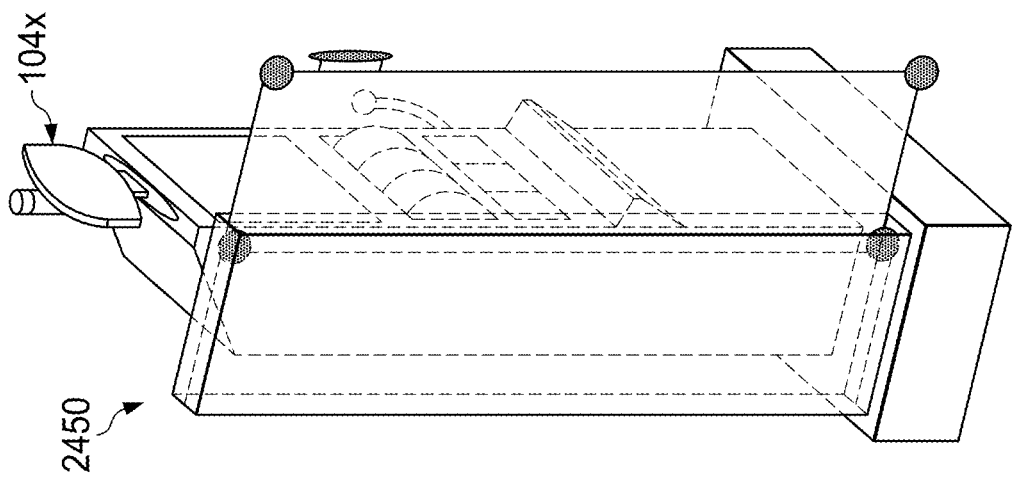
FIGS. 24A-24C is an exemplary partition sanitization system for an electronic gaming device according to some aspects of the present disclosure.
Figure 24B:
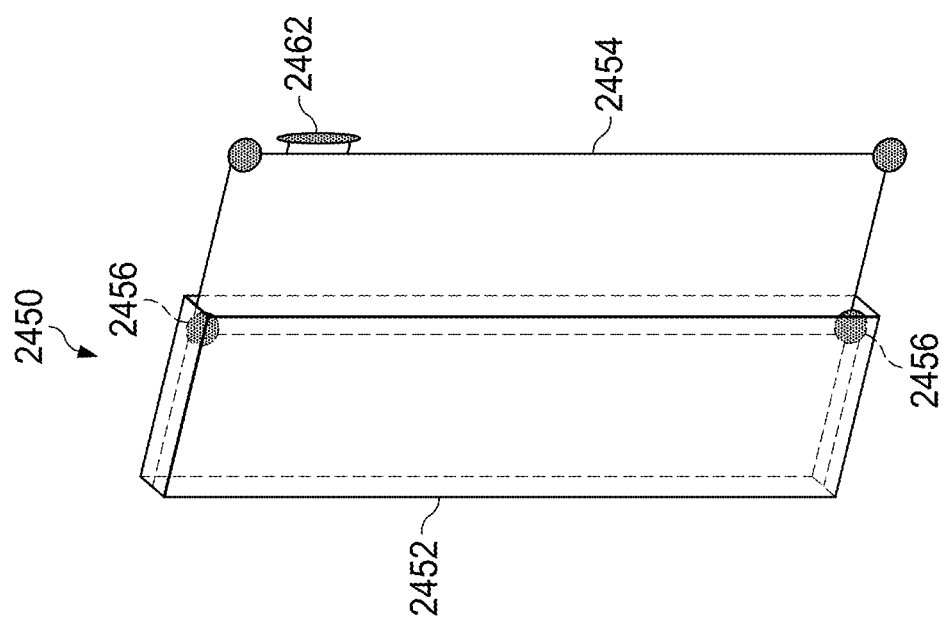
Figure 24A:
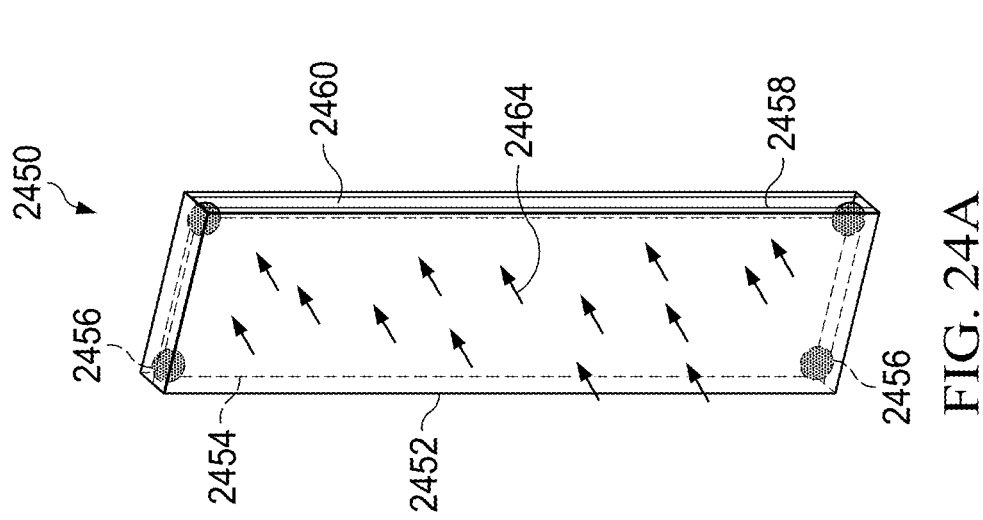

FIGS. 24A-24C show an exemplary partition sanitization system 2450 for an EGM 104x or other electronic gaming device according to some aspects of the present disclosure. An enclosure 2452 is arranged proximate to the EGM 104x. The enclosure 2452 includes one or more light sources to provide UV light 964. A partition 2454 is configured to be at least partially inserted into the enclosure 2452 in a storage configuration (shown in FIG. 24A) and to be at least partially extending from the enclosure in a deployed configuration (shown in FIG. 24B). In some examples, the one or more UV light sources are configured to perform a sanitization operation on the partition 2454 in the storage configuration.

In some examples, one or more rails 2456 or wheels, a track, or a low-friction material facilitate movement of the partition 2454 into and out of the enclosure 2452. In some examples, one or more actuators control movement of the partition 2454 in response to a command from control circuitry.

One or more flexible elements 2458 (e.g., a rubber blade, a series of brushes, a fabric, or a polymer) may be arranged at an opening 2460 of the enclosure 2452. The one or more flexible elements 2458 are configured to at least partially contact the partition 2454 as it moves into or out from the enclosure 2452. This partial contact can form at least a partial screen at the opening 2460 in the storage configuration to at least partially block UV light 2464 from escaping the enclosure 2452 during the sanitization operation. Further, this partial contact can wipe particles and/or fluid from the partition 2462 as it moves into or out from the enclosure 2452. The flexible elements 2458 may be coupled to UV devices to operate as the partition 2454 moves into our out of the enclosure 2452.

In some examples, a fluid disinfectant may also be applied to the partition 2454. A handle 2462 can be attached to the partition 2454 to enable manual movement of the partition 2454.

XVIII. Alternatives and Variations.

Numerous embodiments are described in this disclosure, and are presented for illustrative purposes only. The described embodiments are not, and are not intended to be, limiting in any sense. The present disclosure is widely applicable to numerous embodiments, as is readily apparent from the disclosure. One of ordinary skill in the art will recognize that the innovations described herein may be practiced with various modifications and alterations, such as structural, logical, software, and electrical modifications. Although particular features of the innovations described herein may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the innovations described herein that must be present in all embodiments.

The Title (set forth at the beginning of the first page of this disclosure) is not to be taken as limiting in any way as the scope of the disclosed embodiments. Headings of sections provided in this disclosure are for convenience only, and are not to be taken as limiting the disclosure in any way.

When an ordinal number (such as "first," "second," "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget." Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When introducing elements of aspects of the present disclosure or embodiments thereof, the articles "a," "an," "the," and "said" are intended to mean that there are one or more of the elements. The terms "comprising," "including," and "having" are intended to be inclusive and mean that there may be additional elements other than the listed elements.

When a single device, component, structure, or article is described herein, more than one device, component, structure or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component, structure, or article is described herein (whether or not they cooperate), a single device, component, structure, or article may alternatively be used in place of the more than one device, component, structure, or article that is described. For example, a plurality of computer-based devices may be substituted with a single computer-based device. Accordingly, the various functionality that is described as being possessed by more than one device, component, structure, or article may alternatively be possessed by a single device, component, structure, or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Further, the systems and methods described herein are not limited to the specific embodiments described herein but, rather, operations of the methods and/or components of the system and/or apparatus may be utilized independently and separately from other operations and/or components described herein. Further, the described operations and/or components may also be defined in, or used in combination with, other systems, methods, and/or apparatus, and are not limited to practice with only the systems, methods, and storage media as described herein.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the innovations described herein. Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the innovations described herein, and does not imply that the illustrated process is preferred.

Although a process may be described as including a plurality of steps, that does not indicate that all or even any of the steps are essential or required. Various other embodiments within the scope of the present disclosure include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the present disclosure include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise.

For the sake of presentation, the detailed description uses terms like "determine" and "select" to describe computer operations in a computer system. These terms denote operations performed by a computer, and should not be confused with acts performed by a human being. The actual computer operations corresponding to these terms vary depending on implementation. For example, "determining" something can be performed in a variety of manners, and therefore the term "determining" (and like terms) can indicate calculating, computing, deriving, looking up (e.g., in a table, database or data structure), ascertaining, recognizing, and the like.

As used herein, the term "send" denotes any way of conveying information from one component to another component, and the term "receive" denotes any way of getting information at one component from another component. The two components can be part of the same computer system or different computer systems. The information can be passed by value (e.g., as a parameter of a message or function call) or passed by reference (e.g., in a buffer). Depending on context, the information can be communicated directly between the two components or be conveyed through one or more intermediate components. As used herein, the term "connected" denotes an operable communication link between two components, which can be part of the same computer system or different computer systems. The operable communication link can be a wired or wireless network connection, which can be direct or pass through one or more intermediate components (e.g., of a network). Communication among computers and devices may be encrypted to insure privacy and prevent fraud in any of a variety of ways well known in the art.

It will be readily apparent that the various methods and algorithms described herein may be implemented by, e.g., appropriately programmed general-purpose computers and computing devices. Typically, a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium for performing the process. The apparatus that performs the process can include components and devices (e.g., a processor, input and output devices) appropriate to perform the process. A computer-readable medium can store program elements appropriate to perform the method.

The term "computer-readable medium" refers to any non-transitory storage or memory that may store computer-executable instructions or other data in a computer system and be read by a processor in the computer system. A computer-readable medium may take many forms, including but not limited to non-volatile storage or memory (such as optical or magnetic disk media, a solid-state drive, a flash drive, PROM, EPROM, and other persistent memory) and volatile memory (such as DRAM). The term "computer-readable media" excludes signals, waves, and wave forms or other intangible or transitory media that may nevertheless be readable by a computer.

The present disclosure provides, to one of ordinary skill in the art, an enabling description of several embodiments and/or innovations. Some of these embodiments and/or innovations may not be claimed in the present application, but may nevertheless be claimed in one or more continuing applications that claim the benefit of priority of the present application. Applicants may file additional applications to pursue patents for subject matter that has been disclosed and enabled but not claimed in the present application.

The foregoing description discloses only exemplary embodiments of the present disclosure. Modifications of the above disclosed apparatus and methods which fall within the scope of the present disclosure will be readily apparent to those of ordinary skill in the art. For example, although the examples discussed above are illustrated for a gaming market, embodiments of the present disclosure can be implemented for other markets. The gaming system environment of the examples is not intended to suggest any limitation as to the scope of use or functionality of any aspect of the disclosure.

XIX. Innovative Features.

Innovative features of the present disclosure include, but are not limited to, the following features.

|     | Feature |
| --- | --- |
| A1  | An electronic gaming device comprising a cabinet, a display, a button deck, a processor, memory, and one or more ultraviolet ("UV") light sources, wherein the one or more UV light sources are arranged along at least one edge of the button deck so as to, when activated, emit UV light across at least part of the button deck. |
| A2  | The electronic gaming device of A1, wherein the one or more UV light sources are arranged along an edge of the button deck that is closest to a user position, and wherein the one or more UV light sources are arranged so as to, when activated, emit UV light away from the user position. |
| A3  | The electronic gaming device of A1, wherein the one or more UV light sources are arranged along an edge of the button deck that is farthest from a user position, and wherein the one or more UV light sources are arranged so as to, when activated, emit UV light towards the user position. |
| A4  | The electronic gaming device of A1, wherein the one or more UV light sources are embedded in the cabinet along the at least one edge of the button deck. |
| A5  | The electronic gaming device of A1, further comprising a visor or armrest positioned to block at least some of the UV light emitted by the one or more UV light sources, when activated. |
| A6  | The electronic gaming device of A1, wherein the button deck includes one or more physical buttons, each of the one or more physical buttons including a button housing, a spring, and a switch. |
| A7  | The electronic gaming device of A1, wherein the button deck includes one or more touchscreen buttons. |
| A8  | The electronic gaming device of A1, wherein the one or more UV light sources are arranged along: one edge of the button deck; two opposite edges of the button deck; all but one edge of the button deck; or all edges of the button deck. |
| A9  | The electronic gaming device of A1, further comprising one or more additional UV light sources arranged along at least one edge of the display so as to, when activated, emit UV light across at least part of the electronic gaming device. |
| A10 | The electronic gaming device of A9, wherein the one or more UV light sources arranged along the at least one edge of the button deck and the one or more additional UV light sources are arranged along opposite edges. |
| B1  | An electronic gaming device comprising a cabinet, a display, a button deck, a processor, memory, and one or more ultraviolet ("UV") light sources, wherein the one or more UV light sources are arranged along at least one edge of the display so as to, when activated, emit UV light across at least part of the display. |
| B2  | The electronic gaming device of B1, wherein the one or more UV light sources are arranged along an edge of the display that is closest to a user position, and wherein the one or more UV light sources are arranged so as to, when activated, emit UV light away from the user position. |
| B3  | The electronic gaming device of B1, wherein the one or more UV light sources are arranged along an edge of the display that is farthest from a user position, and wherein the one or more UV light sources are arranged so as to, when activated, emit UV light towards the user position. |
| B4  | The electronic gaming device of B1, wherein the one or more UV light sources are embedded in the cabinet along the at least one edge of the display. |
| B5  | The electronic gaming device of B1, wherein the one or more UV light sources are embedded in the display along the at least one edge of the display. |
| B6  | The electronic gaming device of B1, further comprising a reflective shield positioned to block at least some of the UV light emitted by the one or more UV light sources, when activated. |
| B7  | The electronic gaming device of B1, wherein the display is a touchscreen display. |
| B8  | The electronic gaming device of B1, wherein the display is a video display. |
| B9  | The electronic gaming device of B8, wherein the video display is a main video display or a secondary video display. |
| B10 | The electronic gaming device of B8, wherein the video display is a curved display. |
| B11 | The electronic gaming device of B1, wherein the display includes one or more mechanical reels. |
| B12 | The electronic gaming device of B1, wherein the one or more UV light sources are arranged along: one edge of the display; two opposite edges of the display; all but one edge of the display; or all edges of the display. |

| | Feature |
|---|---|
| C1 | An electronic gaming device comprising a cabinet, a display, a button deck, a processor, memory, and one or more ultraviolet ("UV") light sources, wherein the one or more UV light sources are arranged along a movable part of the electronic gaming device so as to, when activated, emit UV light across at least part of the electronic gaming device. |
| C2 | The electronic gaming device of C1, wherein the movable part of the electronic gaming device is configured to fit, in a nesting manner, into the electronic gaming device during normal use of the electronic gaming device. |
| C3 | The electronic gaming device of C1, wherein the movable part is a cover assembly adapted to swing, at a hinge at the top of the electronic gaming device, over at least part of the electronic gaming device. |
| C4 | The electronic gaming device of C3, wherein the cover assembly includes a housing, the housing having a reflective coating on an underside of the housing, the one of more UV light sources being attached to the underside of the housing. |
| C5 | The electronic gaming device of C3, wherein the cover assembly includes multiple panels, each of the multiple panels having a reflective coating on an underside of the panel, some of the one of more UV light sources being attached to the underside of the panel. |
| C6 | The electronic gaming device of C1, wherein the movable part is a bar assembly adapted to roll, along tracks, over at least part of the electronic gaming device, the one or more UV light sources being attached to the bar assembly. |
| C7 | The electronic gaming device of C6, wherein the tracks run along the front, side edges of the electronic gaming device. |
| C8 | The electronic gaming device of C1, wherein the movable part is an arm assembly adapted to swing, from one or more pivot points, over at least part of the electronic gaming device, the one or more UV light sources being attached to the arm assembly. |
| C9 | The electronic gaming device of C1, wherein the movable part is an arm assembly adapted to swing, from one or more pivot points at an edge of the display, outward over at least part of the electronic gaming device, the one or more UV light sources being attached to the arm assembly. |
| D1 | An electronic gaming device comprising a cabinet, a display, a button deck, a processor, memory, and one or more ultraviolet ("UV") light sources, wherein the one or more UV light sources are arranged so as to, when activated, emit UV light across at least part of the electronic gaming device, and wherein the electronic gaming device is configured to select a UV disinfection mode from among multiple available UV disinfection modes. |
| D2 | The electronic gaming device of D1, wherein the multiple available UV disinfection modes include: a first UV disinfection mode having a first duration, a first scope of coverage, and a first intensity of the UV light; and a second UV disinfection mode having a second duration, a second scope of coverage, and a second intensity of the UV light, wherein the second duration is longer than the first duration, the second scope of coverage is wider than the first scope of coverage, and/or the second intensity of the UV light is higher than the first intensity of the UV light. |
| D3 | The electronic gaming device of D2, wherein the multiple available UV disinfection modes further include: a third UV disinfection mode having a third duration, a third scope of coverage, and a third intensity of the UV light, wherein the third duration is longer than the second duration, the third scope of coverage is wider than the second scope of coverage, and/or the third intensity of the UV light is higher than the second intensity of the UV light. |
| D4 | The electronic gaming device of D2, wherein: the first UV disinfection mode is a user-initiated UV disinfection mode triggered in response to user input, and the second UV disinfection mode is an idle-time disinfection mode triggered in response to inactivity at the electronic gaming device; the first UV disinfection mode is the user-initiated UV disinfection mode, and the second UV disinfection mode is an offline UV disinfection mode triggered in response to deactivation of the electronic gaming device or user input during deactivation of the electronic gaming device; or the first UV disinfection mode is the idle-time UV disinfection mode, and the second UV disinfection mode is the offline UV disinfection mode. |
| D5 | The electronic gaming device of D1, wherein the multiple available UV disinfection modes differ in terms of: duration; scope of coverage over the electronic gaming device; and/or intensity of the UV light. |
| D6 | The electronic gaming device of D1, wherein the one or more UV light sources are: arranged along at least one edge of the display so as to, when activated, emit UV light across at least part of the display; and/or arranged along at least one edge of the button deck so as to, when activated, emit UV light across at least part of the button deck. |
| D7 | The electronic gaming device of D1, wherein the one or more UV light sources are arranged along a movable part of the electronic gaming device so as to, when activated, emit UV light across at least part of the electronic gaming device. |
| AD1 | The electronic gaming device of any one of A1-A10, B1-B12, C1-C9, and D1-D7, wherein the electronic gaming device is adapted for use as a bar counter, adapted for use as a standalone device, or adapted for use as part of a bank of electronic gaming devices. |
| AD2 | The electronic gaming device of any one of A1-A10, B1-B12, C1-C9, and D1-D7, wherein at least part of the cabinet is coated with material adapted to absorb UV light. |

-continued

| | Feature |
|---|---|
| AD3 | The electronic gaming device of any one of A1-A10, B1-B12, C1-C9, and D1-D7, further comprising one or more of: a player tracking system interface; a network connection; a speaker; an additional display; a ticket-out printer; a bill validator or other ticket-in reader; and a card reader. |
| AD4 | The electronic gaming device of any one of A1-A10, B1-B12, C1-C9, and D1-D7, further comprising: a camera oriented towards a user position; and logic, implemented with software and/or hardware, configured to detect a warning condition of a user at the user position. |
| AD5 | The electronic gaming device of AD4, wherein the camera is a hyperspectral camera. |
| AD6 | The electronic gaming device of AD4, wherein the warning condition is a high temperature of the user at the user position, the high temperature being higher than a threshold temperature. |
| AD7 | The electronic gaming device of AD4, wherein the camera is integrated into the cabinet. |
| AD8 | The electronic gaming device of AD4, wherein the camera is fit into a bracket of the electronic gaming device. |
| AD9 | The electronic gaming device of AD4, wherein the camera is fit into a bracket of the electronic gaming device, as part of a player tracking system interface assembly. |
| AD10 | The electronic gaming device of AD4, wherein the logic is further configured to send a notification of the warning condition to a monitoring service. |
| AD11 | The electronic gaming device of AD4, wherein the logic is further configured to trigger a UV disinfection cycle. |
| AD12 | The electronic gaming device of any one of A1-A10, B1-B12, C1-C9, and D1-D7, further comprising: a hyperspectral camera oriented towards the button deck or the display; and logic, implemented with software and/or hardware, configured to detect pathogens or heat spots. |
| AD13 | The electronic gaming device of AD12, wherein the camera is integrated into the cabinet. |
| AD14 | The electronic gaming device of AD12, wherein the camera is fit into a bracket of the electronic gaming device. |
| AD15 | The electronic gaming device of AD12, wherein the logic is configured to, based at least in part on feedback from the hyperspectral camera: decide whether or not to emit the UV light; decide where to focus the UV light; adjust intensity of the UV light; and/or adjust wavelength of the UV light. |
| AD16 | AD15. The electronic gaming device of any one of A1-A10, B1-B12, C1-C9, and D1-D7, further comprising: a charging pad configured to charge a mobile device; and/or a disinfection assembly configured to disinfect a mobile device. |
| E1 | An apparatus comprising a housing and one or more ultraviolet ("UV") light sources, the housing being shaped to fit over a least part of an electronic gaming device or chip tray, and the one or more UV light sources being arranged inside the housing so as to, when activated, emit UV light towards the at least part of the electronic gaming device or chip tray. |
| E2 | The apparatus of E1, wherein the apparatus is a hood shaped to fit over the at least part of the electronic gaming device or chip tray. |
| E3 | The apparatus of E1, wherein the housing is a panel having arranged, on one side of the panel, an array of at least some of the one or more UV light sources, the apparatus further comprising a cover over the panel. |
| E4 | The apparatus of E1, wherein the inside of the housing is coated with material adapted to reflect UV light. |
| E5 | The apparatus of E1, wherein the housing has a concave recess that at least approximately follows contours of the least part of an electronic gaming device or chip tray. |
| E6 | The apparatus of E1, further comprising: a power supply configured to, when connected by a wired or wireless charging connection to the electronic gaming device or chip tray, supply electrical current to the one or more UV light sources. |
| E7 | The apparatus of E1, further comprising: an anchor configured to attach the apparatus to an anchor position on the electronic gaming device or chip tray. |
| F1 | An apparatus comprising a partition and one or more ultraviolet ("UV") light sources, the partition being shaped to fit between two or more electronic gaming devices in a bank of electronic gaming devices, the one or more UV light sources being arranged along the partition so as to, when activated, emit UV light towards at least part of the two or more electronic gaming devices. |
| F2 | The apparatus of F1, wherein the partition is a single pane shaped to fit between a pair of the electronic gaming devices. |
| F3 | The apparatus of F1, wherein the partition consists of n panes joined at a central rigid element, the n panes being shaped to fit between n electronic gaming devices among the electronic gaming devices. |
| F4 | The apparatus of E1, further comprising: a power supply configured to, when connected by a wired or wireless charging connection to one of the electronic gaming devices, supply electrical current to the one or more UV light sources. |
| G1 | An apparatus comprising multiple sections shaped to hold gaming chips and one or more ultraviolet ("UV") light sources, wherein the one or more UV light sources are arranged along at least one edge of the apparatus so as to, when activated, emit UV light across at least part of the multiple sections. |

| Feature | |
|---|---|
| G2 | The apparatus of G1, wherein the one or more UV light sources are arranged along an edge of the apparatus that is closest to a user position, and wherein the one or more UV light sources are arranged so as to, when activated, emit UV light away from the user position. |
| G3 | The apparatus of G1, wherein the one or more UV light sources are embedded in the apparatus along the at least one edge of the apparatus. |
| G4 | The apparatus of G1, wherein the one or more UV light sources are arranged along: one edge of the apparatus; two opposite edges of the apparatus; all but one edge of the apparatus; or all edges of the apparatus. |
| H1 | An apparatus comprising a housing, adapted to fit into a receptacle of an electronic gaming device, and one or more ultraviolet ("UV") light sources, wherein the one or more UV light sources are arranged along at least one edge of the housing so as to, when activated, emit UV light across at least part of the electronic gaming device. |
| H2 | The apparatus of H1, wherein the one or more UV light sources are embedded in the housing along the at least one edge of the housing. |
| H3 | The apparatus of H1, wherein the one or more UV light sources are arranged along: one edge of the housing; two opposite edges of the housing; all but one edge of the housing; or all edges of the housing. |
| H4 | The apparatus of H1, further comprising a display, within the housing, for the electronic gaming device. |
| H5 | The apparatus of H1, further comprising a player tracking system, within the housing, for the electronic gaming device. |
| I1 | An apparatus comprising: multiple panels, each of the multiple panels including an array of ultraviolet ("UV") light sources arranged on a side of the panel so as to, when activated in place over at least part of an electronic gaming device, emit UV light towards the at least part of the electronic gaming device; and a cover flexibly connecting the multiple panels. |
| I2 | The apparatus of I1, further comprising, for at least one of the multiple panels: a reflective shield enclosing at least at least part of the panel, the shield being arranged so as to, when the UV light sources are activated in place over the at least part of an electronic gaming device, reflect the UV light towards the at least part of the electronic gaming device and block escape of the UV light away from the at least part of the electronic gaming device. |
| I3 | The apparatus of I1, further comprising: a power supply configured to, when connected by a wired or wireless charging connection to the electronic gaming device, supply electrical current to the arrays of UV light sources. |
| I4 | The apparatus of I1, further comprising: an anchor configured to attach the apparatus to an anchor position on the electronic gaming device. |
| I5 | The apparatus of I1, wherein each of the multiple panels has dimensions and a shape that at least generally follows contours of a corresponding part of the electronic gaming device. |
| I6 | The apparatus of I1, wherein at least one of the multiple panels is rigid. |
| I7 | The apparatus of I1, wherein at least one of the multiple panels is flexible. |
| AI1 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources are one or more UV light-emitting diodes. |
| AI2 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources are one or more UV lamps. |
| AI3 | The electronic gaming device or apparatus of AI2, wherein the one or more UV lamps are Xenon flash lamps or mercury vapor lamps. |
| AI4 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources, when activated, predominately emit: UV-A light within a range of approximately 315 nanometers to approximately 400 nanometers; UV-B light within a range of approximately 280 nanometers to approximately 315 nanometers; or UV-C light within a range of approximately 100 nanometers to approximately 280 nanometers. |
| AI5 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources, when activated, predominately emit UV-C light, within a range of approximately 240 nanometers to approximately 280 nanometers. |
| AI6 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources are arranged in one or more light strips, each of the one or more light strips including multiple UV light sources of the one or more UV light sources. |
| AI7 | The electronic gaming device or apparatus of A16, wherein each of the one or more light strips is embedded in a recessed cavity adapted to fit the light strip. |
| AI8 | The electronic gaming device or apparatus of any one of A1-A10, B1-B12, C1-C9, D1-D7, AD1-AD16, E1-E7, F1-F4, G1-G4, H1-H5, and I1-I7, wherein each of the one or more UV light sources is in a socket. |
| AI9 | The electronic gaming device or apparatus of AI8, wherein the socket is embedded a recessed cavity adapted to fit the socket. |
| AI10 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources are stationary. |

| | Feature |
|---|---|
| AI11 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources are active, being configured to move along at least one dimension when activated. |
| AI12 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources, when activated, emit the UV light at an intensity that is at least roughly constant. |
| AI13 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources, when activated, emit the UV light at an intensity that is variable. |
| AI14 | The electronic gaming device or apparatus of AI13, wherein the intensity of the UV light varies depending on: UV disinfection mode; orientation away from a user position, the intensity of the UV light being highest at an orientation directly away from the user position and decreasing at orientations closer to the user position; and/or orientation towards one or more touch points, the intensity of the UV light being highest at an orientation directly towards the one or more touch points and decreasing at orientations further from the one or more touch points. |
| AI15 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources, when activated, emit the UV light at a wavelength that is at least roughly constant. |
| AI16 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources, when activated, emit the UV light at a wavelength that is variable. |
| AI17 | The electronic gaming device or apparatus of AI16, wherein the wavelength of the UV light varies depending on: target pathogen; and/or UV disinfection mode. |
| AI18 | The electronic gaming device or apparatus of any one of A1-A10, B1-B12, C1-C9, D1-D7, AD1-AD16, E1-E7, F1-F4, G1-G4, H1-H5, and I1-I7, wherein the one or more UV light sources are configured to be activated in response to an activation condition. |
| AI19 | The electronic gaming device or apparatus of AI18, wherein the activation condition is: inactivity of a user, as indicated by expiration of an activity timer; empty space in a threshold region, as indicated by feedback from a camera; actuation of a button on the electronic gaming device or apparatus; a defined start time for a UV disinfection cycle; a UV-disinfection-start prompt, from a system server, for a UV disinfection cycle; closing of a lid or cover; detection of a warning condition for a user; or detection of a pathogen. |
| P1 | A method of managing ultraviolet ("UV") disinfection of an electronic gaming device or chip tray, the method comprising: detecting an activation condition; and based at least in part on the detecting the activation condition, activating one or more UV light sources, the one or more UV light sources being arranged so as to emit UV light across at least part of the electronic gaming device or chip tray. |
| P2 | The method of P1, further comprising: selecting a UV disinfection mode from among multiple available UV disinfection modes. |
| P3 | The method of P1, further comprising: deactivating the one or more UV light sources; and rendering a screen that indicates status of UV disinfection of the electronic gaming device or chip tray. |
| P4 | The method of P1, further comprising: deactivating the one or more UV light sources; and sending a message that indicates status of UV disinfection of the electronic gaming device or chip tray, the message being sent to one or more of an administrative service, a user account, and a cleaning staff account. |
| P5 | The method of P3 or P4, wherein the status of UV disinfection is that: a UV disinfection cycle has completed for the electronic gaming device or chip tray. |
| Q1 | A method of managing UV disinfection of an electronic gaming device or chip tray, the method comprising: detecting an activation condition; and based at least in part on the detecting the activation condition, rendering a screen that indicates status of UV disinfection of the electronic gaming device or chip tray. |
| Q2 | The method of Q1, wherein the status of UV disinfection is that a UV disinfection cycle has started for the electronic gaming device or chip tray, the method further comprising: activating one or more ultraviolet ("UV") light sources, the one or more UV light sources being arranged so as to emit UV light across at least part of the electronic gaming device or chip tray. |
| Q3 | The method of Q1, wherein the status of UV disinfection is that a UV disinfection cycle has been requested for the electronic gaming device or chip tray, the method further comprising: sending a message that indicates the status of UV disinfection of the electronic gaming device or chip tray, the message being sent to one or more of an administrative service and a cleaning staff account. |
| Q4 | The method of Q1, wherein the status of UV disinfection is that: a UV disinfection cycle has started for the electronic gaming device or chip tray; a UV disinfection cycle has been requested for the electronic gaming device or chip tray; or a UV disinfection cycle has completed for the electronic gaming device or chip tray. |
| R1 | A method of managing UV disinfection of an electronic gaming device or chip tray, the method comprising: detecting an activation condition; and based at least in part on the detecting the activation condition, sending a message that indicates status of |

| | Feature |
|---|---|
| | UV disinfection of the electronic gaming device or chip tray, the message being sent to one or more of an administrative service and a cleaning staff account. |
| R2 | The method of R1, wherein the status of UV disinfection is that: a UV disinfection cycle has started for the electronic gaming device or chip tray; a UV disinfection cycle has been requested for the electronic gaming device or chip tray; or a UV disinfection cycle has completed for the electronic gaming device or chip tray. |
| PR1 | The method of any one of P1-P5, Q1-Q4, and R1-R2, wherein the activation condition is: inactivity of a user, as indicated by expiration of an activity timer; empty space in a threshold region, as indicated by feedback from a camera; actuation of a button on the electronic gaming device or chip tray; a defined start time for a UV disinfection cycle; a UV-disinfection-start prompt, from a system server, for a UV disinfection cycle; closing of a lid or cover; detection of a warning condition for a user; and/or detection of a pathogen. |
| PR2 | An electronic gaming device configured to perform operations for the method of any one of P1-P5, Q1-Q4, and R1-R2. |
| PR3 | The electronic gaming device of PR2, wherein the electronic gaming device includes one or more buttons configured to request a UV disinfection cycle and/or indicate disinfection status of the electronic gaming device. |
| PR4 | A chip tray configured to perform operations for the method of any one of P1-P5, Q1-Q4, and R1-R2. |
| PR5 | A system server configured to perform operations for the method of any one of P1-P5, Q1-Q4, and R1-R2. |
| PR6 | One or more non-transitory computer-readable media having stored thereon computer-executable instructions for causing one or more processors, when programmed thereby, to perform operations for the method of any one of P1-P5, Q1-Q4, and R1-R2. |
| T1 | A mobile sanitization system for a gaming environment, the system comprising: one or more sanitization accessories; a housing configured to at least partially enclose one or more components of an electronic gaming machine (EGM), and to direct the one or more sanitization accessories toward the one or more components; and a control system to activate the one or more sanitization accessories to perform a sanitization operation based on an activation command. |
| T2 | The mobile sanitization system of T1, wherein the one or more sanitization accessories include a liquid application tool or an ultraviolet (UV) light source. |
| T3 | The mobile sanitization system of T2, wherein the UV light source is arranged to direct UV light onto a surface of one or more of the components of the EGM. |
| T4 | The mobile sanitization system of T2, wherein the liquid application tool is arranged to apply a disinfecting liquid onto a surface of one or more of the components of the EGM. |
| T5 | The mobile sanitization system of T1, wherein the housing comprises one or more fasteners configured to secure the one or more sanitization accessories. |
| T6 | The mobile sanitization system of T5, wherein the one or more fasteners are configured to secure the one or more sanitization accessories in a first orientation to sanitize a first component of the one or more components and in a second orientation to sanitize a second component. |
| T7 | The mobile sanitization system of T5, wherein the one or more sanitization accessories are removable. |
| T8 | The mobile sanitization system of T1, wherein each sanitization accessory of the one or more sanitization accessories can be activated independently of another sanitization accessory. |
| T9 | The mobile sanitization system of T1, further comprising one or more wheels to support the housing. |
| T10 | The mobile sanitization system of T9, wherein the one or more wheels are supported by one or more casters to allow rotation of the one or more wheels. |
| T11 | The mobile sanitization system of T9, further comprising a drive system to turn the wheels to move the system. |
| T12 | The mobile sanitization system of T1, further comprising one or more sensors to identify objects. |
| T13 | The mobile sanitization system of T12, wherein the sensors include one or more of infrared (IR) sensors, acoustic sensors, vision sensors, tactile sensors, radar, Light Detection and Ranging (LIDAR) sensors. |
| T14 | The mobile sanitization system of T1, further comprising an extension attachment configured to extend from an end of the housing facing the gaming environment to be cleaned and at least partially cover the one or more components. |
| T15 | The mobile sanitization system of T14, wherein the extension attachment provides a protective cover to at least partially prevent liquid or light from escaping the gaming environment during a cleansing or sanitizing operation. |
| T16 | The mobile sanitization system of T15, further comprising one or more actuators to control one or more shields of the extension attachment to extend from the housing to form the protective cover. |
| T17 | The mobile sanitization system of T1, further comprising one or more displays to provide an indication of a cleaning operation. |
| T18 | The mobile sanitization system of T1, further comprising one or more of a user interface configured to receive commands from an operator, or a network interface configured to receive commands from a remote computing platform. |

| | Feature |
|---|---|
| T19 | The mobile sanitization system of T1, wherein the control system is configured to execute one or more artificial intelligence or machine learning algorithms to autonomously control sanitization of the gaming environment. |
| T20 | The mobile sanitization system of T1, further comprising a frame configured to support the system during a sanitization operation, the frame configured to deploy from a storage mode to an operational mode in response to a user command. |
| U1 | A system for sanitizing an electronic gaming machine (EGM) comprising: one or more ultraviolet (UV) light sources; a sanitization platform to secure a UV light source of the one or more UV light sources to the EGM, wherein the sanitization platform is oriented to direct UV light from the UV light source toward a component of the EGM and away from a user; and control circuitry configured to receive one or more user inputs to control operation of the sanitization platform. |
| U2 | The system of U1, wherein the sanitization platform comprises an enclosure to contain an object therein, wherein an interior of the enclosure provides one or more UV lighting sources to perform a cleansing or sanitization operation. |
| U3 | The system of U2, wherein the enclosure is configured to open to deposit one or more objects in response to a first input, close and seal the enclosure in response to a second input, and activate a cleansing or sanitizing operation upon feedback indicating the enclosure is closed and sealed. |
| U4 | The system of U2, wherein the interior of the enclosure further comprises one or more liquid dispensing devices to perform a liquid cleansing or sanitization operation. |
| U5 | The system of U1, wherein the sanitization platform is removably secured to the EGM. |
| U6 | The system of U1, wherein the sanitization platform is arranged at a top portion of the EGM or in proximity to a button panel, and oriented to direct light from the one or more UV light sources to a respective surface of the EGM. |
| U7 | The system of U6, wherein the sanitization platform is configured to: move to a first position relative to the EGM to perform a first cleansing or sanitizing operation; and move to a second position relative to the EGM to perform a second cleansing or sanitizing operation. |
| U8 | The system of U6, further comprising control circuitry to receive a command to initiate a cleansing or sanitizing operation in response to a sensor input, a timer, or based on a user input. |
| U9 | The system of U6, wherein the user is to provide commands via a contact input or a contactless input. |
| V1 | An electronic gaming machine (EGM) comprising: a contactless user interface comprising one or more sensors to measure one or more gesture inputs from a user; and control circuitry configured to: receive sensor data corresponding to the one or more gesture inputs; compare the sensor data to a list associating sensor data to gesture commands; and determining a gesture command based on the comparison. |
| V2 | The electronic gaming machine of V1, further comprising one or more physical user interfaces to receive an input to control one or more operations of the EGM, wherein the one or more physical user interfaces is configured to be removed and replaced with the contactless user interface. |
| W1 | A system for controlling an electronic gaming machine (EGM) comprising: a stylus configured to provide commands via a contact input or a contactless input; a user interface comprising one or more sensors to receive the inputs from a user; and control circuitry configured to: receive sensor data from the one or more sensors corresponding to the inputs; compare the sensor data to a list associating sensor data to a plurality of commands; and determining a desired command of the plurality of commands based on the comparison. |
| W2 | The system of W1, wherein the stylus comprises a transceiver to transmit or receive signals from a contactless sensor of the one or more sensors. |
| W3 | The system of W1, wherein the stylus comprises an active stylus to provide increased sensitivity during the contact input between the stylus and a contact enabled sensor of the one or more sensors. |
| W4 | The system of W1, wherein the stylus comprises circuitry which includes a stylus identification code. |
| W5 | The system of W1, wherein the stylus comprises circuitry which includes a user identification code. |
| X1 | A protective cover configured to follow contours of one or more physical user interfaces of an electronic gaming device, the protective cover comprising a material or an adhesive to removably secure the protective cover to one or more surfaces of the one or more physical user interfaces. |
| X2 | The protective cover of X1, wherein the one or more physical user interfaces includes a button deck with one or more physical buttons, the one or more physical buttons including a button housing, a spring, or a switch. |
| X3 | The protective cover of X2, wherein the button deck includes one or more touchscreen buttons. |
| Y1 | An electronic gaming machine (EGM) comprising: a foot activated user interface comprising one or more sensors to measure one or more gesture inputs from a user's foot; and control circuitry configured to: receive sensor data corresponding to the one or more gesture inputs; compare the sensor data to a list associating sensor data to gesture commands; and determining a gesture command based on the comparison. |
| Z1 | A system for sanitizing a partition for an electronic gaming machine (EGM) comprising: an enclosure arranged proximate to the EGM, the enclosure including |

| Feature | |
|---|---|
| | one or more ultraviolet (UV) light sources; and a partition configured to be at least partially inserted into the enclosure in a storage configuration and to be at least partially extending from the enclosure in a deployed configuration, wherein the one or more UV light sources are configured to perform a sanitization operation on the partition in the storage configuration. |
| Z2 | The system of Z1, further comprising one or more of rails, wheels, a track, or a low-friction material to facilitate movement of the partition into and out of the enclosure. |
| Z3 | The system of Z1, further comprising one or more actuators to control movement of the partition in response to a command from control circuitry. |
| Z4 | The system of Z1, further comprising one or more flexible elements at an opening of the enclosure, the one or more flexible elements configured to at least partially contact the partition as it moves into or out from the enclosure. |
| Z5 | The system of Z4, wherein the one or more flexible elements forms at least a partial screen at the opening in the storage configuration to at least partially block UV light from escaping the enclosure during the sanitization operation. |
| Z6 | The system of Z4, wherein the one or more flexible elements comprises one or more of a rubber blade, a series of brushes, a fabric, or a polymer. |
| Z7 | The system of Z1, further comprising a handle to enable manual movement of the partition. |

While the invention has been described with respect to the figures, it will be appreciated that many modifications and changes may be made by those skilled in the art without departing from the spirit of the invention. Any variation and derivation from the above description and figures are included in the scope of the present invention as defined by the claims. In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A sanitization system comprising:
an electronic gaming device comprising a cabinet, a display, a button deck, a processor, and a memory; and
one or more ultraviolet ("UV") light sources, wherein the one or more UV light sources are arranged so as to, when activated, emit UV light across at least part of the electronic gaming device,
wherein the sanitization system is configured to select a UV disinfection mode from among at least a first UV disinfection mode and a second UV disinfection mode,
wherein the first UV disinfection mode has a first duration, a first scope of coverage, and a first intensity of the UV light,
wherein the second UV disinfection mode has a second duration, a second scope of coverage, and a second intensity of the UV light, and
wherein at least one of the following conditions (a)-(c) is met: (a) the second duration is longer than the first duration, (b) the second scope of coverage is wider than the first scope of coverage, (c) the second intensity of the UV light is higher than the first intensity of the UV light, or combinations thereof.

2. The sanitization system of claim 1, wherein the one or more UV light sources are arranged so as to, when activated, emit UV light across at least the button deck.

3. The sanitization system of claim 1, wherein the one or more UV light sources are embedded in the cabinet along at least one edge of the button deck.

4. The sanitization system of claim 1, wherein at least one of the one or more UV light sources is embedded in the cabinet along at least one edge of the display.

5. The sanitization system of claim 1, wherein the electronic gaming device further comprises a reflective shield positioned to block at least some of the UV light emitted by the one or more UV light sources, when activated.

6. The sanitization system of claim 1, wherein the one or more UV light sources are arranged along:
one edge of the button deck;
two opposite edges of the button deck;
all but one edge of the button deck; or
all edges of the button deck.

7. The sanitization system of claim 1, wherein the one or more UV light sources are arranged so as to, when activated, emit UV light across at least the display.

8. The sanitization system of claim 1, further comprising one or more additional UV light sources arranged along a movable part of the electronic gaming device so as to, when activated, emit UV light across at least part of the electronic gaming device.

9. The sanitization system of claim 8, wherein the movable part comprises a bar assembly arranged to roll along tracks.

10. The sanitization system of claim 1, further comprising a detachable protective sheet arranged so as to cover the button deck.

11. The sanitization system of claim 1, wherein the button deck further comprises one or more sensors arranged in a contactless interface to determine one or more gesture commands of a user of the electronic gaming device.

12. The sanitization system of claim 1, wherein the sanitization system is configured to select the first UV disinfection mode and the second UV disinfection mode from among multiple available UV disinfection modes.

13. The sanitization system of claim 1, wherein the sanitization system is further configured to present, via the display of the electronic gaming device, a user notification indicating the first or second duration, respectively.

14. The sanitization system of claim 1, further comprising:
one or more sensors oriented toward a user position; and
logic, implemented with software and/or hardware, configured to detect a warning condition of a user at the user position.

15. The sanitization system of claim 14, wherein the logic is further configured to, in response to detecting the warning condition, disable the one or more UV light sources.

\* \* \* \* \*